(12) United States Patent
Mansky et al.

(10) Patent No.: US 6,535,822 B2
(45) Date of Patent: Mar. 18, 2003

(54) SENSOR ARRAY FOR RAPID MATERIALS CHARACTERIZATION

(76) Inventors: Paul Mansky, 3732 23$^{rd}$ St., #3, San Francisco, CA (US) 94114; James Bennett, 652 Robin Dr., Santa Clara, CA (US) 95050

( * ) Notice: Subject to any disclaimer, the term of this patent is extended or adjusted under 35 U.S.C. 154(b) by 0 days.

(21) Appl. No.: 09/863,532

(22) Filed: May 23, 2001

(65) Prior Publication Data

US 2002/0032531 A1 Mar. 14, 2002

Related U.S. Application Data

(63) Continuation of application No. 09/210,428, filed on Dec. 11, 1998.

(51) Int. Cl.$^7$ .............................................. G01N 27/26
(52) U.S. Cl. ........................... 702/21; 702/22; 702/27; 702/30; 702/32; 422/68.1
(58) Field of Search ............................. 702/19, 21–24, 702/136, 27, 28, 30–32, 57, 64, 65, 113–119, 124, 126, 130, 132–134, 183, 184, 189, FOR 105–FOR 106, FOR 115–FOR 119, FOR 134, FOR 135, FOR 142, FOR 143, FOR 170, FOR 171; 700/266, 268, 269, 299, 300; 422/70, 89, 68.1, 88, 98, 30, 83, 90, 82.01, 82.12, 82.13, 82.05, 82.02, 82.03, 82.06, 61, 66, 67, 69, 81, 82.04, 76, 77, 82.11, 51; 436/149–151, 806, 157, 43; 435/287.1, 287.9, 288.7; 374/43, 50, 36, 142, 32, 31, 117; 73/863, 863.01–863.03, 863.11, 863.12; 204/400, 401, 416, 406–410, 298.11; 205/775, 776.5, 787, 782.5

(56) References Cited

U.S. PATENT DOCUMENTS

| | | | |
|---|---|---|---|
| 3,266,307 A | 8/1966 | DeWinter | 73/190 |
| 3,789,662 A | 2/1974 | Zettler et al. | 73/190 |
| 4,350,446 A | 9/1982 | Johnson | 374/13 |
| 4,423,371 A | 12/1983 | Senturia et al. | 324/663 |
| 4,448,943 A | 5/1984 | Golba et al. | 526/59 |
| 4,571,543 A | 2/1986 | Raymond et al. | 324/425 |
| 4,596,697 A | 6/1986 | Ballato | 422/98 |
| 4,675,674 A | 6/1987 | Hope | 340/870.13 |

(List continued on next page.)

FOREIGN PATENT DOCUMENTS

| | | |
|---|---|---|
| DE | 198 05 719 | 12/1998 |
| WO | PCT/US98/07799 | 4/1998 |

OTHER PUBLICATIONS

Sullivan, P.F. and G. Seidel "Steady–state, AC–temperature calorimetry" Physical Review vol. 73 No. 3; Sep. 15, 1968; p. 679–685.

(List continued on next page.)

Primary Examiner—Hal Wachsman

(57) ABSTRACT

A sensor-array based materials characterization apparatus includes a sensor array disposed on a substrate; electronic test circuitry for sending and receiving electrical signals; electronic circuitry for routing signals between selected sensors and the electronic test circuitry; and a computer or processor. Preferably, all or part of the electronic test and signal routing circuitry is contained on the same substrate as the sensor array. Additional circuitry and a processor or computer may be physically separate from the substrate carrying the sensor array, and may be connected to the sensor array substrate. During use, multiple samples are applied to the multiple sensors in the array, and signals are sent to and received from selected sensors. Integration of the electronic test and signal routing circuitry onto the same substrate as the sensor array allows for a high density of sensors on a single substrate, permitting rapid analysis of combinatorial libraries.

17 Claims, 25 Drawing Sheets

U.S. PATENT DOCUMENTS

| | | | |
|---|---|---|---|
| 4,710,550 A | 12/1987 | Kranbuehl | 526/60 |
| 4,723,908 A | 2/1988 | Kranbuehl | 432/37 |
| 4,743,954 A | 5/1988 | Brown | 257/253 |
| 4,767,719 A | 8/1988 | Finlan | 436/501 |
| 4,874,250 A | 10/1989 | Gonner | 374/43 |
| 4,891,591 A | 1/1990 | Johnston et al. | 324/234 |
| 4,950,608 A | 8/1990 | Kishimoto | 435/290 |
| 5,063,081 A | 11/1991 | Cozzette et al. | 435/4 |
| 5,095,278 A | 3/1992 | Hendrick | 324/687 |
| 5,098,196 A | 3/1992 | O'Neill | 374/11 |
| 5,164,319 A | 11/1992 | Hafeman et al. | 435/287.1 |
| 5,179,028 A | 1/1993 | Vali et al. | 436/524 |
| 5,224,775 A | 7/1993 | Reading et al. | 374/11 |
| 5,228,114 A | 7/1993 | Suzuki | 392/416 |
| 5,283,037 A | 2/1994 | Baer et al. | 422/82.01 |
| 5,296,374 A | 3/1994 | Culshaw et al. | 435/287.9 |
| 5,306,644 A | 4/1994 | Myerholtz et al. | 436/149 |
| 5,335,993 A | 8/1994 | Marcus et al. | 374/11 |
| 5,345,213 A | 9/1994 | Semancik et al. | 338/34 |
| 5,346,306 A | 9/1994 | Reading et al. | 374/10 |
| 5,356,756 A | 10/1994 | Cavicchi et al. | 430/315 |
| 5,439,291 A | 8/1995 | Reading | 374/11 |
| 5,445,008 A | 8/1995 | Wachter et al. | 73/24.06 |
| 5,464,966 A | 11/1995 | Gaiten et al. | 219/544 |
| 5,474,385 A | 12/1995 | Reading | 374/11 |
| 5,491,097 A | 2/1996 | Ribi et al. | 436/518 |
| 5,525,300 A | 6/1996 | Danssaert et al. | 422/99 |
| 5,532,128 A | 7/1996 | Eggers et al. | 435/6 |
| 5,533,393 A | 7/1996 | Bonne et a. | 73/335.02 |
| 5,534,111 A | 7/1996 | Hocker et al. | 216/15 |
| 5,557,972 A | 9/1996 | Jacobs et al. | 73/756 |
| 5,571,401 A | 11/1996 | Lewis et al. | 205/787 |
| 5,597,957 A | 1/1997 | Schieferdecker et al. | 73/755 |
| 5,599,104 A | 2/1997 | Nakamura et al. | 374/12 |
| 5,601,141 A | 2/1997 | Gordon et al. | 165/263 |
| 5,602,393 A | 2/1997 | Gerard | 250/338.4 |
| 5,622,633 A | 4/1997 | Ohtsuka et al. | 438/53 |
| 5,632,957 A | 5/1997 | Heller et al. | 422/68.1 |
| 5,634,718 A | 6/1997 | Martinis et al. | 374/32 |
| 5,635,845 A | 6/1997 | Strong et al. | 324/693 |
| 5,639,423 A | 6/1997 | Northup et al. | 422/50 |
| 5,641,391 A | 6/1997 | Hunter et al. | 205/89 |
| 5,641,634 A | 6/1997 | Mandecki | 435/6 |
| 5,653,939 A | 8/1997 | Hollis et al. | 422/50 |
| 5,659,127 A | 8/1997 | Shie et al. | 73/31.05 |
| 5,667,667 A | 9/1997 | Southern | 205/687 |
| 5,668,303 A | 9/1997 | Geisler et al. | 73/24.06 |
| 5,670,322 A | 9/1997 | Eggers et al. | 435/6 |
| 5,698,089 A | 12/1997 | Lewis et al. | 205/787 |
| 5,705,399 A | 1/1998 | Larue | 436/501 |
| 5,739,686 A | 4/1998 | Naughton et al. | 324/259 |
| 5,755,942 A | 5/1998 | Zanzucchi et al. | 204/454 |
| 5,759,493 A | 6/1998 | Raisanen | 422/88 |
| 5,766,934 A | 6/1998 | Guiseppi-Elie | 435/287.9 |
| 5,770,038 A | 6/1998 | Iwama et al. | 205/775 |
| 5,776,359 A | 7/1998 | Schultz et al. | 423/263 |
| 5,779,362 A | 7/1998 | Lightfoot | 374/33 |
| 5,779,981 A | 7/1998 | Danssaert et al. | 374/99 |
| 5,783,805 A | 7/1998 | Katzmann | 219/494 |
| 5,788,373 A | 8/1998 | Huetter et al. | 374/10 |
| 5,788,833 A * | 8/1998 | Lewis et al. | 204/406 |
| 5,806,979 A | 9/1998 | Gschneidner et al. | |
| 5,813,763 A | 9/1998 | Plotnikov et al. | 374/11 |
| 5,821,596 A | 10/1998 | Miu et al. | 257/419 |
| 5,832,411 A | 11/1998 | Schatzmann et al. | 702/23 |
| 5,876,118 A | 3/1999 | Vogel | 374/11 |
| 5,891,395 A | 4/1999 | Glaunsinger et al. | 422/53 |
| 5,923,421 A | 7/1999 | Rajic et al. | 356/328 |
| 5,939,312 A | 8/1999 | Baier et al. | 435/287.2 |
| 5,945,069 A | 8/1999 | Buehler | 422/90 |
| 6,017,144 A | 1/2000 | Guo et al. | 700/121 |
| 6,037,167 A | 3/2000 | Adelman et al. | 435/285.1 |
| 6,045,671 A | 4/2000 | Wu et al. | 204/298.11 |
| 6,079,873 A | 6/2000 | Cavicchi et al. | 374/10 |
| 6,093,302 A | 7/2000 | Montgomery | 205/122 |
| 6,111,520 A | 8/2000 | Allen et al. | 340/870.16 |
| 6,167,748 B1 | 1/2001 | Britton, Jr. et al. | 73/24.06 |
| 6,170,318 B1 * | 1/2001 | Lewis | 340/632 |
| 6,215,898 B1 | 4/2001 | Woodfill et al. | 382/154 |
| 6,290,911 B1 * | 9/2001 | Lewis et al. | 204/406 |
| 6,338,112 B1 | 1/2002 | Wipfel et al. | 710/269 |
| 6,350,369 B1 * | 2/2002 | Lewis et al. | 204/412 |
| 6,387,329 B1 * | 5/2002 | Lewis et al. | 422/83 |

OTHER PUBLICATIONS

"Micron Scale Differential Scanning Calorimeter," http://www.cstl.nist.gov/div836/836.04/SensorProj/Microcal.html, 3 pages. (No date).

"Sensor Platforms," http://www.cstl.nist.gov//div836/836.04/SensorProj/SensorPlatforms.html. 1 page (No date).

"Thermodynamic Measurements of Magnetic Ordering in Antiferromagnetic Superlattices," E.N. Abarra, K. Takano, F. Hellman, and A.E. Berkowitz, *Physical Review Letters*, vol. 77, No. 16, Oct., 14, 1996, pp. 3451–3454.

"The Anatomy of a Microcalorimeter," Kim Allen, http://physics,ucsd.edu/~kallen/Microcal/calorimeter,html, 14 pages (No date).

"Heat Capacity Measurements on Small Samples at Low Temperatures," R. Bachmann, F.J. DiSalvo, Jr., T.H. Geballe, R.L. Greene, R.E. Howard, C.N. King, H.C. Kirsch, K.N. Lee, R.E. Schwall, H.U. Thomas, and R.B. Zubeck, *The Review of Scientific Instruments*, vol. 43, No. 2, Feb. 1792, pp. 205–214.

"Micromechanical Thermogravimetry, " R. Berger, H.P. Lang, Ch. Gerber, J.K. Gimzewski, J.H. Fabian, L. Scandella, E. Meyer, H.J. Guntherodt, *Chemical Physics Letters*, vol. 294, Sep. 18, 1998, pp. 363–369.

"An Ultrahigh Vacuum Single Crystal Adsorption Microcalorimeter," C.E. Borroni–Bird and D.A. King, *Rev. Sci. Instrum.*, vol. 62, No. 9, Sep. 1991, pp. 2177–2185.

"Relaxation Phenomena in Dense, Glassy Membranes Prepared from a Polymer Solution, Monitored by Changes in Dielectric Properties," R.H.B. Bouma, Th. van den Boomgaard, C.A. Smolders, H. Strathmann, P.F. Mijnlieff, *Journal of Membrane Science*, vol. 113, 1996, pp. 205–221. (No month).

"A Class of Cobalt Oxide Magnetoresistance Materials Discovered with Combinatorial Synthesis," Gabriel Briceno, Hauyee Chang, Xiaodong Sun, Peter G. Schultz, X.D. Xiang, *Science*, vol. 270, Oct. 13, 1995, pp. 273–275.

"Thermal Conductivity Measurement from 30 to 750 K: the 3ω Method," David G. Cahill, *Rev. Sci. Instrum.*, vol. 61, No. 2, Feb. 1990, pp. 802–808.

"Thermal Conductivity of a–Si:H Thin Films," David G. Cahill, M. Katiyar, and J.R. Abelson, *The American Physical Society*, vol. 50, No. 9, Sep. 1, 1994, pp. 6077–6081.

"Pulsed Desorption Kinetics Using Micromachined Microhotplate Arrays," Richard E. Cavicchi, Gregory E. Poirier, John S. Suehle, Michael Gaitan, Steve Semancik, and Donald R. F. Burgess, *J. Vac. Sci. Technol.*, vol. 12, No. 4, Jul./Aug. 1994, pp. 2549–2553.

"A Combinational Chemistry Apprach to Oxidation Catalyst Discovery and Optimization," Peigun Cong, Dan Giaquinta, Shenhang Guan, Eric McFarland, Kyle Self, Howard Turner and W. Henry Weinburg, *Process Miniaturization: 2nd International Conference on Microreaction Technology Brochure*, pp. 118–123. (No date).

"Thin Film Microcalorimeter for Heat Capacity Measurements from 1.5 to 800 K," D.W. Denlinger, E.N. Abarra, Kimberly Allen, P.W. Rooney, M.T. Messer, S.K. Watson, and F. Hellman, *Rev. Sci. Instrum.*, vol. 65, No. 4, Apr. 1994, pp. 946–958.

"Plastification During Sorption of Polymeric Thin Films: A Quartz Resonator Study," Arno Domack and Diethelm Johannsmann, *J. Appl. Phys.*, vol. 80, No. 5, Sep. 1, 1996, pp. 2599–2604.

"A Silicon on Sapphire Thermometer for Small Sample Low Temperature Calorimetry," S. R. Early, F. Hellman, J. Marshall, and T. H. Geballe, *Physics*, vol. 107B, 1981, pp. 327–328.

"Nanocalorimeter for High Resolution Measurements of Low Temperature Heat Capacities of Thin Films and Single Crystals," Fernando Fominaya, Thierry Fournier, Philippe Gandit, and Jacques Chaussy, *Rev. Sci. Instrum.*, vol. 68, No. 11, Nov. 1997, pp. 4191–4195.

"Heat Capacity Cryostat and Novel Methods of Analysis for Small Specimens in the 1.5–10 K Range," E.M. Forgan and S. Nedjat, *Rev. Sci. Instrum.*, vol. 51, No. 4, Apr. 1980, pp. 411–417.

"Thermal Conductivity and Diffusivity Measurements in the sub–$\mu$s Scale on Centimeter Area Samples Using a Microthermocouple," R. Forster and E. Gmelin, *Rev. Sci. Instrum.*, vol. 67, No. 12, Dec. 1996, pp. 4246–4255.

"An AC Calorimeter for Measuring Heat Capacity of Free–Standing Liquid–Crystal Films," R. Geer, T. Stoebe, T. Pitchford, and C.C. Huang, *Rev. Sci. Instrum.*, vol. 62, No. 2, Feb. 1991, pp. 415–421.

Abstract, "Microcalorimetric Study of the Acidic Character of Modified Metal Oxide Surfaces. Influence of the Loading Amount on Alumina, Magnesia, and Silica," A. Gervasini, *Langmuier*, vol. 12, 1996, 1 page (No month).

"Modulated–bath Calorimetry," J.E. Graebner, *Rev. Sci. Instrum.*, vol. 60, No. 6, Jun. 1989, pp. 1123–1128.

"Specific Heat of Granular Aluminum Films," R.L. Greene, C.N. King, and R.B. Zubeck, *Physical Review B*, vol. 6, No. 9, Nov. 1, 1972, pp. 3297–3304.

Abstract, "Localized Thermal Analysis Using a Mechanical Resistive Probe," A. Hammiche, M. Reading, H.M. Pollock, and M. Song, *Rev. Sci. Instrum.*, vol. 67, No. 12, Dec. 1996, pp. 4268–4274.

"Nanocalorimeter for Explorations of Mesoscopic Heat Flow," E.A. Henriksen, K.C. Schwab, J.M. Worlock, M.L. Roukes, http://www.cmp.caltech.edu/~lifshitz/march98/abs98.h, 1 page (No date).

"Experimental Limitations in Impedance Spectroscopy of Materials Systems," G. Hsieh, D.D. Edwards, S.J. Ford, J.H. Hwang, J. Shane, E.J. Garboczi, and T.O. Mason, *Mat. Res. Soc. Symp. Proc.*, vol. 411, 1996, pp. 3–13. (No month).

"Visco–elastic Properties of Thin Films Probed with a Quartz Crystal Resonator," D. Johannsmann, F. Embs, C.G. Willson, G. Wegner, and W. Knoll, *Makromol. Chem., Macromol. Symp.*, vol. 46, 1991, pp. 247–251. (No month).

"Dielectric Monitoring of Polymerization and Cure," David E. Kranbuehl, *Dielectric Spectroscopy of Polymeric Materials*, pp. 303–328. (No date).

"Microcalorimeters May Provide a Solution to the Big Problem of Small Contaminants," Ray Ladbury, *Physics Today*, Jul. 1998, pp. 19–21.

"Heat Capacity Measurements of Sn Nanostructures Using a Thin–Film Differential Scanning Calorimeter with 0.2 nJ Sensitivity," S.L. Lai, G. Ramanath, L.H. Allen, and P. Infante, *Appl. Phys. Lett.*, vol. 70, No. 1, Jan. 6, 1997, pp. 43–45.

"High–Speed ($10^{4}$°C/s) Scanning Microcalorimetry with Monolayer Sensitivity ($J/m^2$)," S.L. Lai, G. Ramanath, and L.H. Allen, *Appl. Phys. Lett.*, vol. 67, No. 9, Aug. 28, 1995, pp. 1229–1231.

"Size–Dependent Melting Properties of Small Tin Particles: Nanocalorimetric Measurements," S.L. Lai, J.Y. Guo, V. Petrova, G. Ramanath, and L.H. Allen, *Physical Review Letters*, vol. 77, No. 1, Jul. 1, 1996, pp. 99–102.

"Determination of Complex Shear Modulus with Thickness Shear Mode Resonators," Ralph Lucklum, Carsten Behling, Richard W. Cernosek, and Stephen J. Martin, *IOP Publishing*, Sep. 1996, pp. 346–356.

"Materials Test Equipment—Materials Measurement Systems," *1998 Hewlett–Packard Test and Measurement Catalog*, pp. 349–351. (No month).

"$\mu$TA 2990 Micro–Thermal Analyzer—Characterizing the Nano–World," *TA Instruments Thermal Analysis & Rheology Brochure*. (No date).

"A 3–350 K Fast Automatic Small Calorimeter," V.K. Pecharsky, J.O. Moorman, and K.A. Gschneider, Jr., *Rev. Sci. Instrum.*, vol. 68, No. 11, Nov. 1997, pp. 4196–4207.

"The Broad Sweep of Integrated Microsystems," S. Tom Picraux and Paul J. McWhorter, *IEEE Spectrum*, Dec. 1998, pp. 24–33.

"A Very Sensitive Microcalorimetry Technique for Measuring Specific Heat of $\mu$g Single Crystals," O. Riou, P. Gandit, M. Charalambous, and J. Chaussy, *Rev. Sci. Instrum.*, vol. 68, No. 3, Mar. 1997, pp. 1501–1509.

"Measurement of Low–Temperature Specific Heat," G.R. Stewart, *Rev. Sci. Instrum.*, vol. 54, No. 1, Jan. 1983, pp. 1–11.

"A Study of Los–Cost Sensors for Measuring Low Relative Humidity," P.R. Story, D.W. Galipeau, R.D. Mileham, *Sensors and Actuators B*, vol. 24–25, 1995, pp. 681–685. (No month).

"Microcalorimetric Study of Ethylene on Pt{110}—(1 x 2)," A. Struck, C.E. Wartnaby, Y.Y. Yeo, and D.A. King, *Physical Review Letters*, vol. 74, No. 4, Jan. 23, 1995, pp. 578–581.

"Steady–State, ac–Temperature Calorimetry," Paul F. Sullivan and G. Seidel, *Physical Review*, vol. 173, No. 3, Sep. 15, 1968, pp. 679–685.

"AC Temperature Calorimetry for Thin Films at Low Temperatures," Takao Suzuki, Takefumi Tsuboi, and Hideo Takaki, *Japanese Journal of Applied Physics*, vol. 21, No. 2, Feb. 1982, pp. 368–372.

Abstract, "An Apparatus for Measuring the Thermal Conductivity and Viscosity of Polymers Under Shearing Strain," I.H. Tavman, *Meas. Sci. Technol.*, vol. 8, 1997, 1 page. (No month).

"In–Plane Permittivity of Spin–Cast Polymer Films," Shari A. Weinberg and Sue Ann Bidstrup–Allen, *Mat. Res. Socc. Symp. Proc.*, vol. 411, 1996, pp. 229–234. (No month).

"Specific Heat Measurements by Non–Contact Calorimetry," R.K. Wunderlich and H.J. Fecht, *Journal of Non–Crystalline Solids*, vol. 156–158, 1993, pp. 421–424. (No month).

"A Combinatorial Approach to Materials Discovery," X.D. Xiant, Xiaodong Sun, Gabriel Briceno, Yulin Lou, Kai–An Wang, Hauyee Chang, William G. Wallace–Freedman, Sung–Wei Chen, and Peter G. Schultz, *Science,* vol. 268, Jun. 23, 1995, pp. 1738–1740.

"A Capacitance Sensor for On–Line Monitoring of Ultrathing Polymeric Film Growth," Guo–Gang Zhou, Stephen T. Kowel, and M.P. Srinivasan, *IEEE Transactions on Components, Hybrids, and Manufacturing Technology,* vol. 11, No. 2, Jun. 1998, pp. 184–190.

Copending U.S. application Ser. No. 09/210,485; Filed Dec. 11, 1998.

Copending U.S. application Ser. No. 09/458,398; Filed Dec. 10, 1999.

Copending U.S. application Ser. No. 09/210,086; Filed Dec. 11, 1998.

Copending U.S. application Ser. No. 09/858,048; Filed May 15, 2001.

Copending PCT application Ser. No. US99/30008; Filed Dec. 10, 1999.

Semancik, Steve and Richard Cavicchi, "Kinetically Controlled Chemical Sensing Using Micromachined Structures," Accounts of Chemical Research, vol. 31 (No. 5), p. 279–287, (1998). (No month).

* cited by examiner

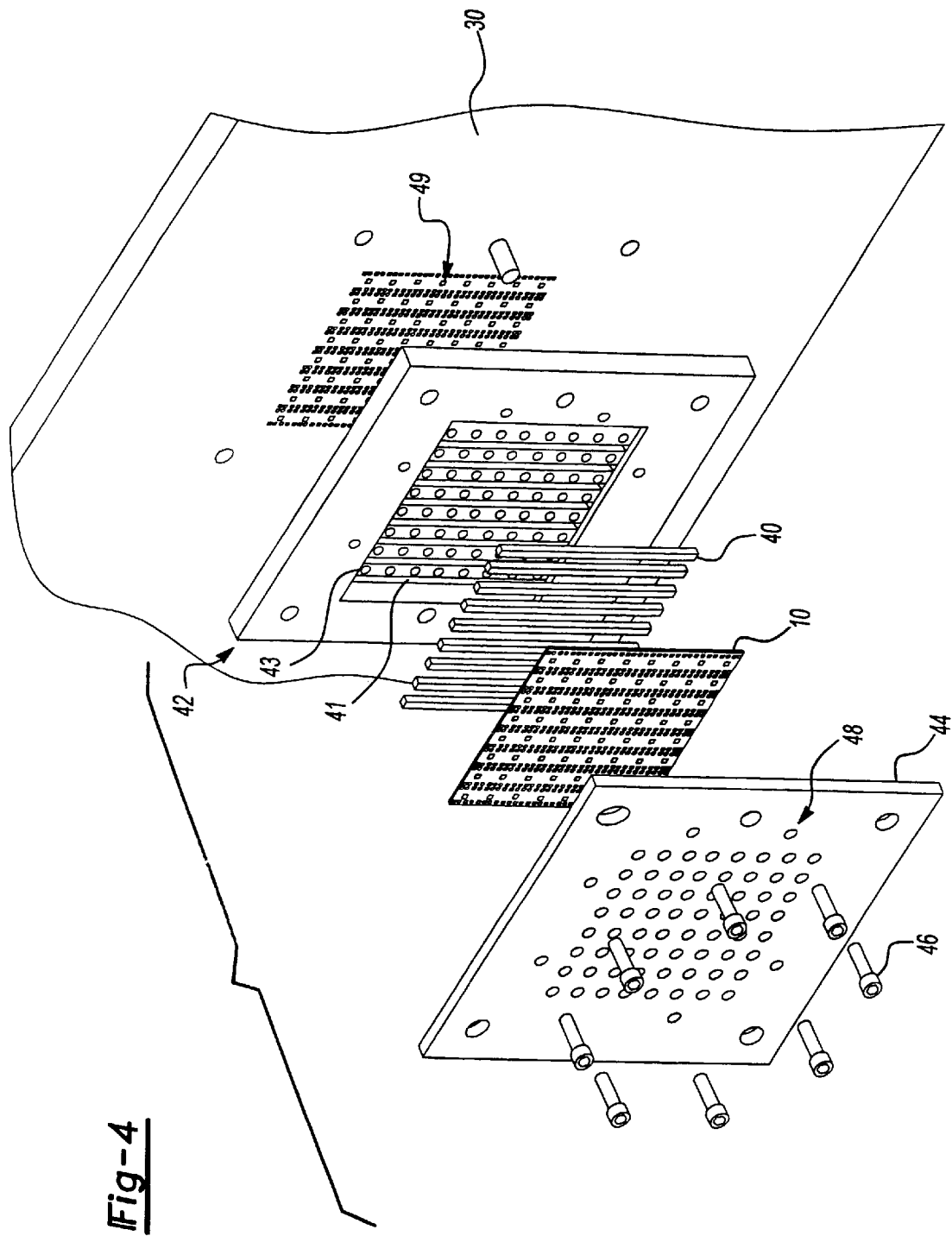

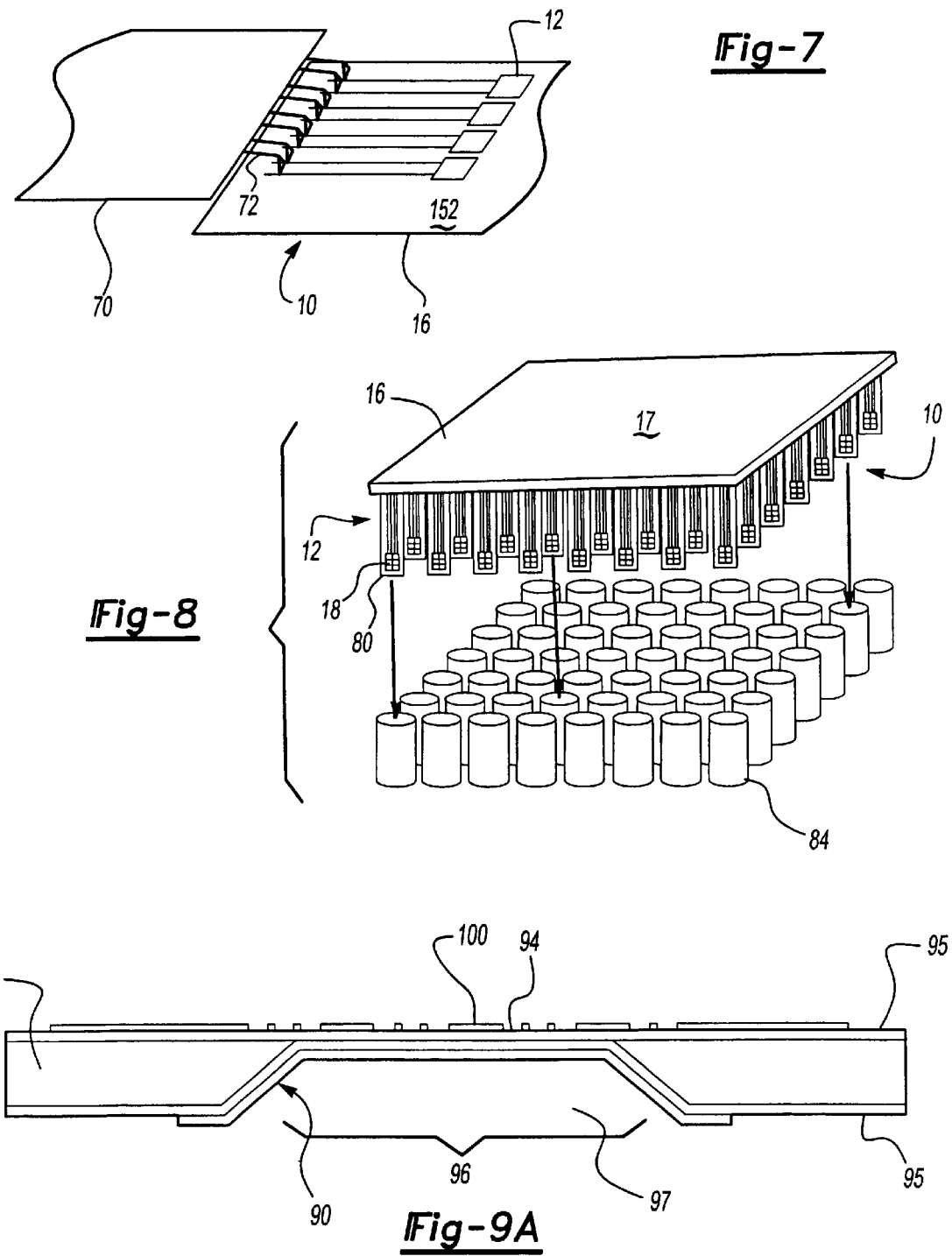

$I(t)=I_0(t)+I_{AC}\sin(\omega t)$  $V_0,\ V(\omega,2\omega,3\omega)$

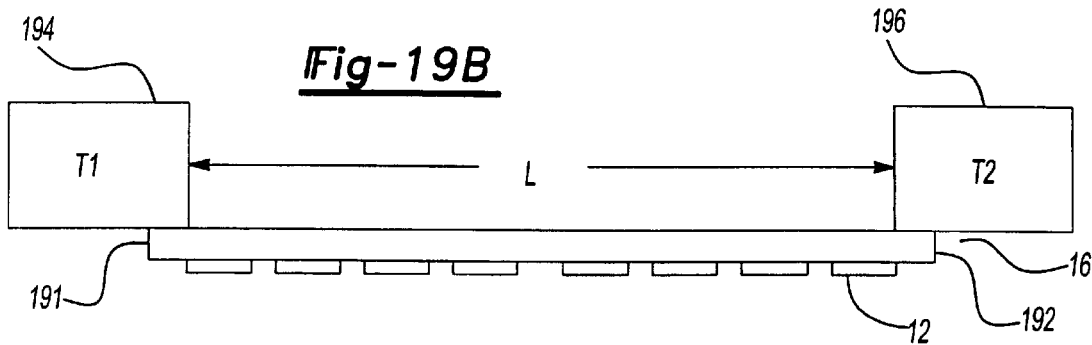
*Fig-19B*
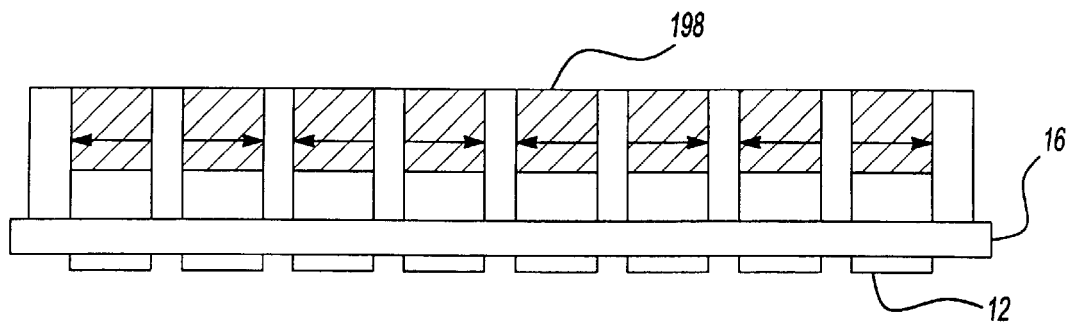
*Fig-19C*
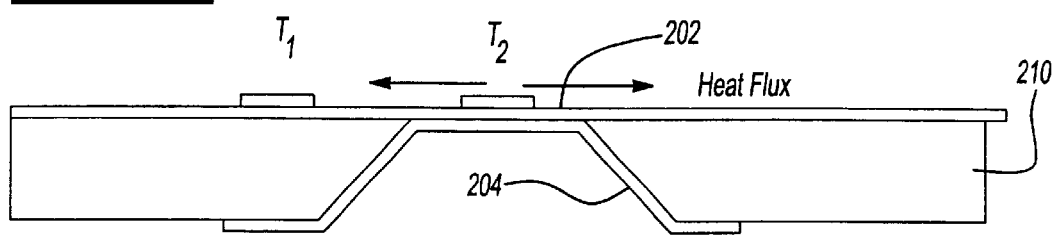
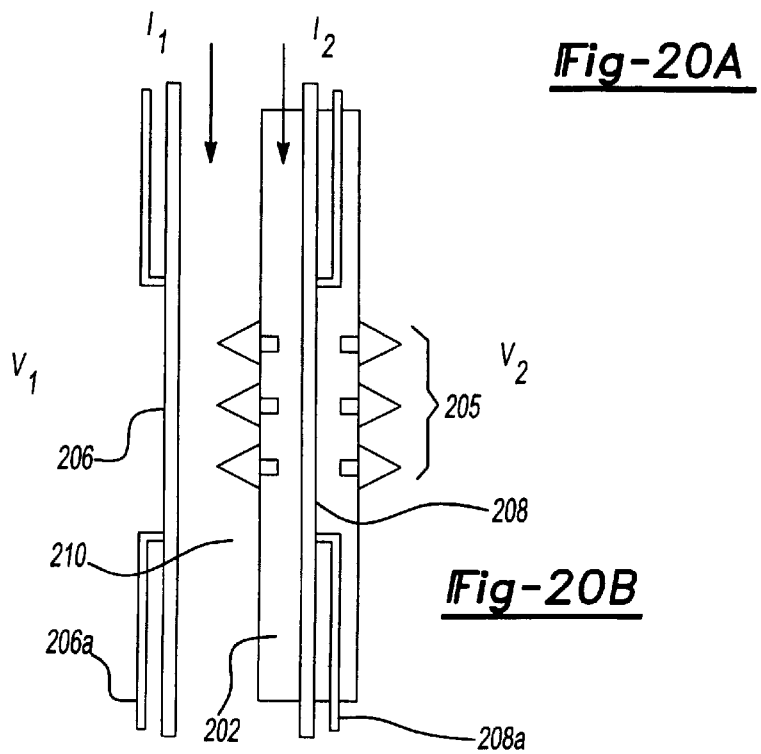
*Fig-20A*
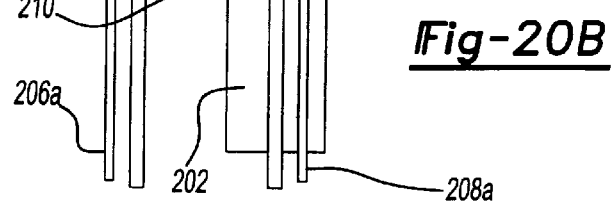
*Fig-20B*

SENSOR ARRAY FOR RAPID MATERIALS CHARACTERIZATION

RELATED CASES

This application is a continuation of copending application: application Ser. No. 09/210,428 filed on Dec. 11, 1998.

The present application is related to U.S. patent application Ser. No. 09/210,485 and U.S. patent application Ser. No. 09/210,086 now U.S. Pat. No. 6,438,497, all filed on Dec. 10, 1998 and incorporated herein by reference.

TECHNICAL FIELD

The present invention is directed to an apparatus and method for characterizing a plurality of organic or inorganic materials, and more particularly to a modular, electrically-driven sensor array that can be coupled to a selected standardized integrated electronic platform to characterize a plurality of materials simultaneously and rapidly.

BACKGROUND

Companies are turning to combinatorial materials science techniques for developing new compounds or materials (including formulations, materials having different processing histories, or mixtures of compounds) having novel physical and chemical properties. Combinatorial materials science refers generally to methods and apparatuses for creating a collection of chemically diverse compounds or materials and to methods and apparatuses for rapidly testing or screening such compounds or materials for desired performance characteristics and/or properties. The collections of chemical compounds or materials are commonly called "libraries". See U.S. Pat. No. 5,776,359, herein incorporated by reference, for a general discussion of combinatorial methodologies.

A virtually infinite number of useful materials or compounds can be prepared by combining different elements of the Periodic Table of Elements in varying ratios, by creating compounds with different arrangements of elements, and by creating materials comprising mixtures of compounds or formulations with differing processing histories. Discovery of useful materials for a particular application may require preparation or characterization of many candidate materials or compounds. Preparing and screening a large number of candidates increases the probability of useful discoveries. Thus, any system that can analyze and characterize the properties of combinatorially prepared library members quickly and accurately is highly desirable.

Many conventional measurement systems comprise a distinct specialized machine for characterizing a particular material property, so that testing of a candidate material can use many machines and be cumbersome and time-consuming. Also, most known materials characterization devices measure only one material sample at a time, severely limiting the number of samples that can be characterized per unit time.

Optical screening methods and devices have been preferred for many combinatorial chemistry and combinatorial materials science applications because they are non-contact and non-destructive. See for example WO 98/15805, incorporated herein by reference. For example, luminescence may be screened optically. When monitoring chemical reactions, for example, thermal imaging with an infrared camera can detect heat released during relatively fast exothermic reactions. See WO 98/15813, incorporated herein by reference. Although optical methods are particularly useful for characterizing materials or properties in certain circumstances, many materials characterization techniques are difficult or impossible to perform using optical methods. Therefore, there is still a need for a more direct materials characterization method that involves more intimate contact between the material samples and the sensing apparatus.

Conventional sensors that generate electrical data corresponding to material properties are typically designed as individual, discrete units, each sensor having its own packaging and wiring connections. Many materials characterization sensors are designed to be used individually in or with a machine that characterizes one sample at a time. Linking a plurality of these individual sensors in an array format, assuming that it is physically possible, would be expensive and often creates overly complicated wiring schemes with minimal gains in operating efficiency for the overall sensing system.

One structure using multiple material samples is a microfabricated array containing "microhotplates". The microhotplates act as miniature heating plates for supporting and selectively heating material samples placed thereon. U.S. Patent No. 5,356,756 to Cavicchi et al and U.S. Pat. No. 5,345,213 to Semancik et al. as well the article entitled "Kinetically Controlled Chemical Sensing Using Micromachined Structures," by Semancik and Cavicchi, (*Accounts of Chemical Research*, Vol. 31, No. 5, 1998), all illustrate the microhotplate concept and are incorporated herein by reference. Although arrays containing microhotplates are known, they have been used primarily to create varied processing conditions for preparing materials. A need still exists for an array-based sensor system that can actually characterize material properties.

It is therefore an object of the invention to provide a materials characterization system that can measure properties of many material samples quickly, and in some embodiments simultaneously.

It is also an object of the invention to construct a materials characterization system having a modular structure that can be connected to a flexible electronic platform to allow many different material properties to be measured with minimal modification of the apparatus.

SUMMARY OF THE INVENTION

This invention provides an apparatus (or system) and method for testing materials in an array format using sensors that contact the materials being tested. Accordingly, the present invention is directed to an electronically-driven sensor array system for rapid characterization of multiple materials. A plurality of sensors are disposed on a substrate to form a sensor array. The embodiment of the invention herein is directed to a system having an integrated substrate including the sensors and either signal selection and routing circuitry (or multiplexers) or circuitry to generate or read signals or both.

Properties that can be measured include thermal, electrical and mechanical properties of samples. Regardless of the property being measured or the specific apparatus, the materials characterization system of the invention includes a multiple sensors carrying multiple material samples, means for routing signals to and from the sensors, electronic test circuitry, and a computer or processor to receive and interpret data from the sensors. In a preferred embodiment, a modular system is constructed including a single sensor array format, and signal routing equipment compatible with this format which can be used with multiple sensor types and multiple electronic test equipment types, permitting maximum flexibility of the system while preserving the general advantages of sensor array-based characterization. Alternatively, some or all of the different parts of the system may be integrated together into a single physical component of the system.

The sensors can be operated in serial or parallel fashion. A wide range of electronically driven sensors may be employed, which those of skill in the art will appreciate provide the opportunity to design an apparatus or method for specific applications or property measurements. The environment in which the measurement is made by the sensor can be controlled.

This invention allows for rapid screening of combinatorial libraries or large numbers of samples prepared by other means. This invention allows for property measurements that cannot be done optically. However, optical measurements may be made in conjunction with the sensor based electronic measurements of this invention. One potentially important feature is the speed of the property measurements made with this invention. Two independent reasons for this speed are that one can measure samples in parallel or with smaller sample sizes than with conventional measurement techniques. Moreover, automated sample handling, array preparation and/or sensor operation allows or a completely automated rapid property measurement system in accord with this invention.

BRIEF DESCRIPTION OF THE DRAWINGS

FIG. 4 is one embodiment of a sensor array/circuit board assembly in the invention;

FIG. 7 illustrates one alternative contact structure for the sensor array;

FIG. 8 illustrates another embodiment of the invention;

FIGS. 9A through 9C are examples of a sensor structure for thermal analysis in the present invention;

FIGS. 19A through 19C illustrate thermoelectric property characterization conducted according to the present invention;

FIGS. 20A and 20B illustrate thermal conductivity characterization conducted according to the present invention.

DETAILED DESCRIPTION

Figure 1A:
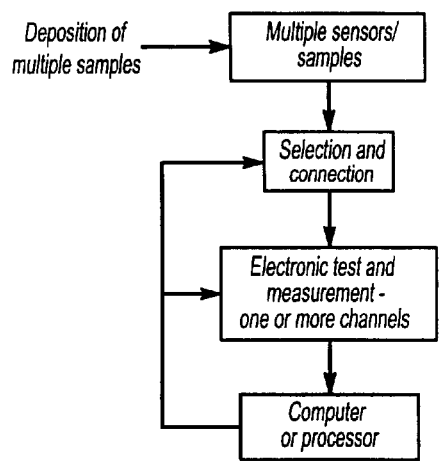
FIGS. 1A through 1E are diagrams illustrating the overall system of the present invention.
Figure 1B:
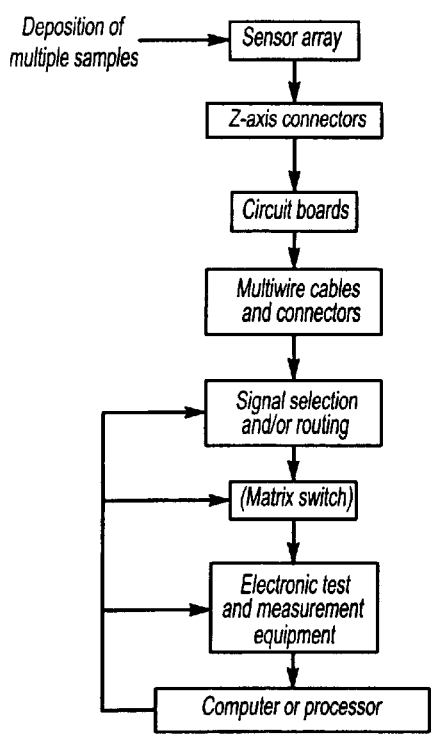
Figure 1C:
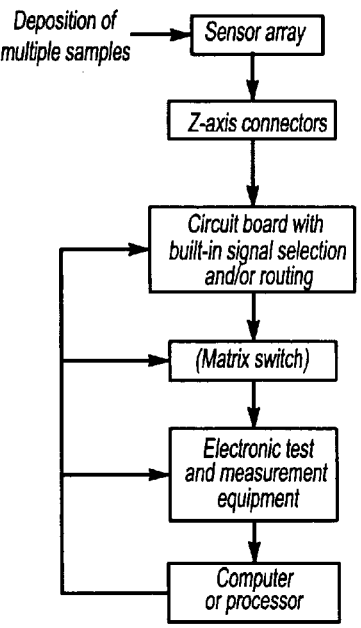
Figure 1D:
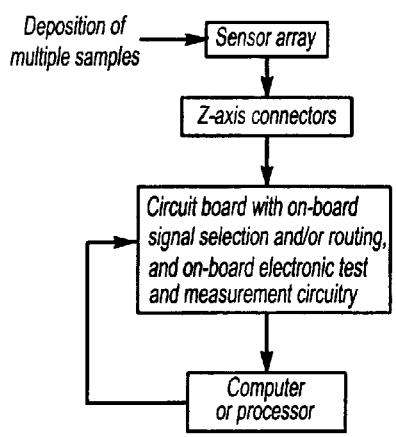
Figure 1E:
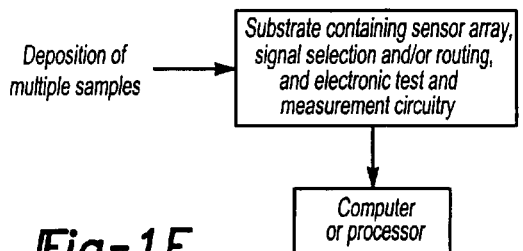

FIG. 1A illustrates the generic apparatus or system concept of the materials characterization system of the present invention, and FIGS. 1B through 1E illustrates possible variations of the system. Regardless of the property being measured or the specific hardware in the apparatus, the materials characterization system of the invention includes multiple sensors in contact with multiple samples, means for routing signals to and from the sensors, electronic test circuitry, and a computer or processor to receive and interpret data from the sensors or the electronic test circuitry. FIG. 1B is a representative diagram of an apparatus where each component is separate and interchangeable, allowing maximum flexibility and interchangeability of parts. FIGS. 1C through 1E illustrate variations where portions of the apparatus, such as the sensor array and electronic test circuitry, are integrated into one part, allowing for a more compact design, but with a greater degree of customization of the apparatus for a particular application or property measurement. Regardless of the degree to which components in the apparatus are integrated into one unit, the overall operation of the sensor-array based apparatus remains the same, as will be explained in further detail below.

In one embodiment that those of skill in the art will appreciate provides a great deal of flexibility, each sensor has adjacent to it a plurality of associated sensor contact pads. Alternatively, the contact pads can be arranged near the edges of the sensor array, with leads on the substrate connecting the sensors to the contact pads, to prevent the contact pads from being contaminated with the materials being tested. The system in this embodiment also includes a printed circuit board having a plurality of board contact pads arranged in the same configuration as the sensor contact pads in the sensor array. Connectors, such as conducting elastomers, stick probes, cantilever probes, conducting adhesives, wafer-to-board bonding techniques, or other contact devices, couple the sensor array with the printed circuit board by creating contacts between the sensor contact pads and the board contact pads, preferably the contacts are reversible and non-permanent. Thus, sensor arrays incorporating different sensor functionalities can be created using the same array and contact pad format and contacted using the same circuit board and connections.

The printed circuit board in the inventive system also includes traces that connect the individual contact pads to standard multi-pin connectors placed near the edges of the board. This construction allows easy connection between the printed circuit board assembly and the rest of the system using standard multi-wire ribbon cable assemblies compatible with the chosen multi-pin connectors. In the system according to a preferred embodiment, the multiwire cables and connectors couple the printed circuit board assembly to a multiplexer or other signal routing means for selecting one or more sensors to be activated, depending on the specific software instructions to the signal routing means. The multiplexer or signal routing means is, in turn, coupled to a flexible electronic platform, which can include electronic test and measurement circuitry, a computer, or both. The electronic platform can also include a switch matrix, preferably under control of the computer, for connecting the multiplexer outputs to a variety of different electronics test instruments without manually reconnecting cables. Thus, when a sensor array incorporating a different sensor functionality is needed, to test for a different material property, only minimal reconfiguration of the electronic platform is needed. In this manner, the same system can be used to test for a wide variety of material properties.

In other cases, it may be desirable to collect information from many sensors simultaneously, rather than in a rapid serial fashion. In the preferred embodiment of the invention for such cases, the multi-wire cables and connectors themselves serve as the signal routing means and are directly attached to an electronics module having a multiplicity of independent electronics channels for driving and reading the sensors. The outputs of these independent channels are then collected by the computer.

The sensor array itself may contain different types of sensors designed to measure different material properties in the different operation modes as well. Further, standardizing the sensor array configuration, the contact format, and the connections from the board to the multiplexer and/or the electronic platform allows easy "plug-and-play" interconnection as well as simplification of the sensor structures themselves. In one embodiment of the invention, no active circuitry is included in the sensor array, reducing the manufacturing cost of the sensor array enough to make the sensor array disposable, if desired.

In a preferred embodiment, the sensor array has the same format as a standardized format used in combinatorial chemistry applications (e.g., an 8×12 grid with 9 mm spacing in between each sensor). By using a standardized format, substances to be tested by the sensors in combinatorial applications can be placed on multiple sensors simultaneously rather than one sensor at a time, e.g., via simultaneous transfer from a standard microtiter plate, further increasing testing and processing speed in the apparatus. The sensors in a single array can be constructed so that they all measure the same material property, or alternatively a single array can contain several different types of sensors that measure different material properties. The modular format of the sensor array, the standardized interconnection means, and the flexible electronic platform allows a great deal of flexibility in determining what types of sensors to include in the array since the same general electronic platform (e.g. electronic test circuitry and computer) and array format is used, regardless of the specific property being measured.

Alternatively, the sensors can be suspended at the end of an array of rods or plates that hang vertically from a common supporting plate, preferably in a standard combinatorial chemistry format, to form a "dipstick" array structure. The sensors can then be dipped simultaneously into wells containing solutions of materials to be characterized. After removing the dipsticks from the solutions and allowing the solvent to evaporate, the sensors are coated with a film of material. The material can then be tested in the same manner as the sensors in the flat sensor array. The materials or liquids can also be tested while in the wells. Other embodiments of the invention include integrating the printed circuit board with the signal routing parts and/or the electronic test circuitry to construct a more customized characterization device or placing all components and electronic circuitry on the same substrate as the sensors.

Figure 2A:
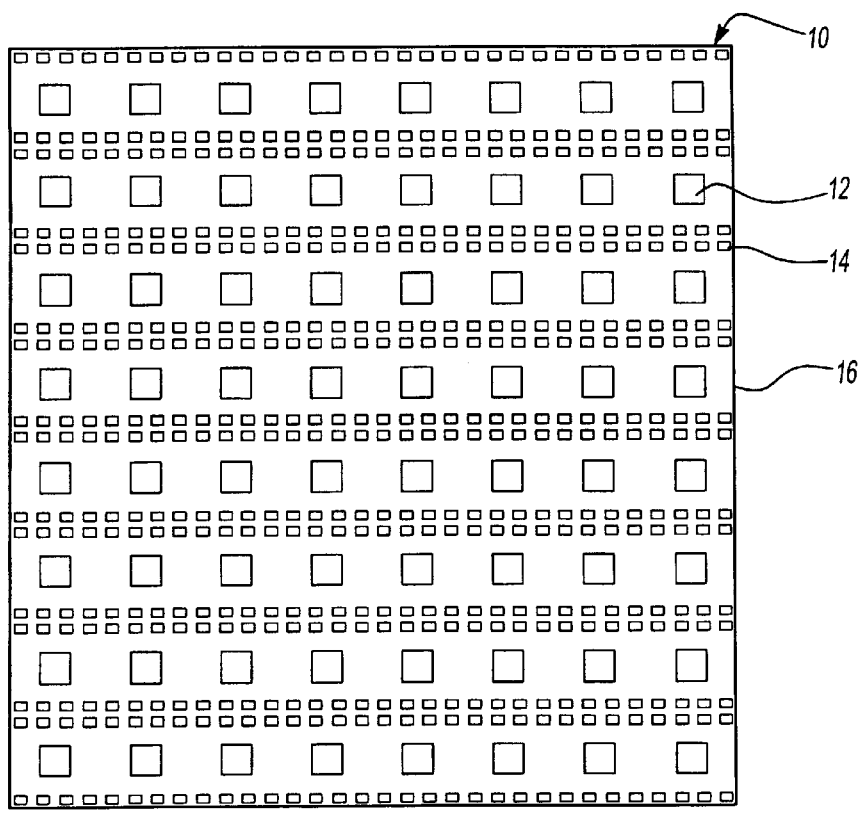
FIGS. 2A through 2D are diagrams illustrating examples of sensor array and contact configurations in the present invention.
Figure 2B:
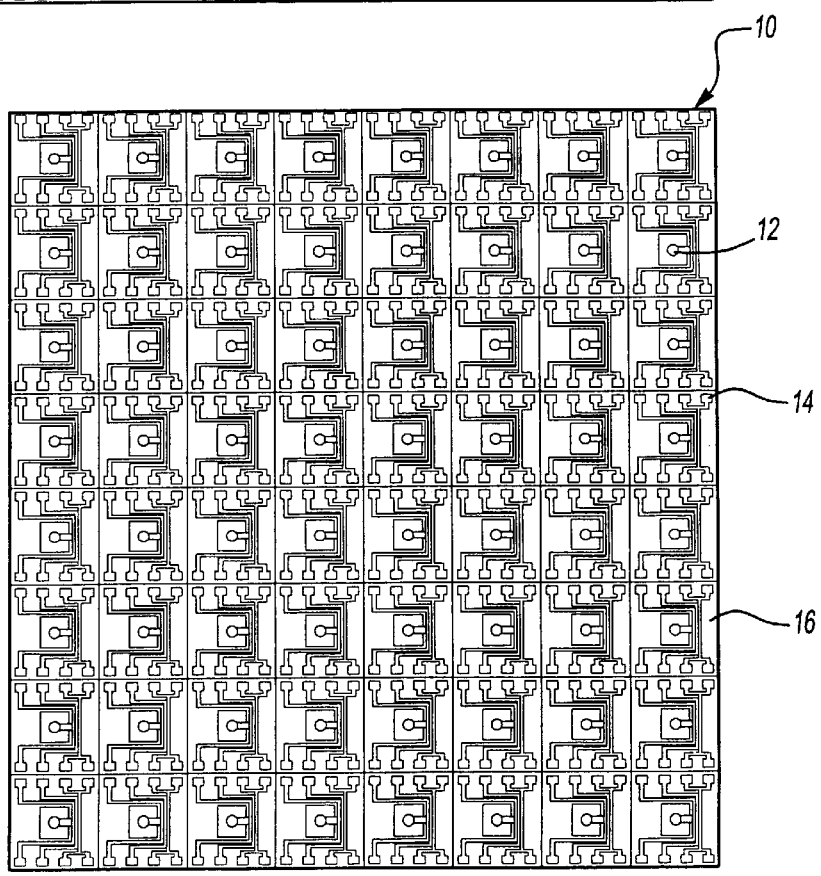
Figure 2C:
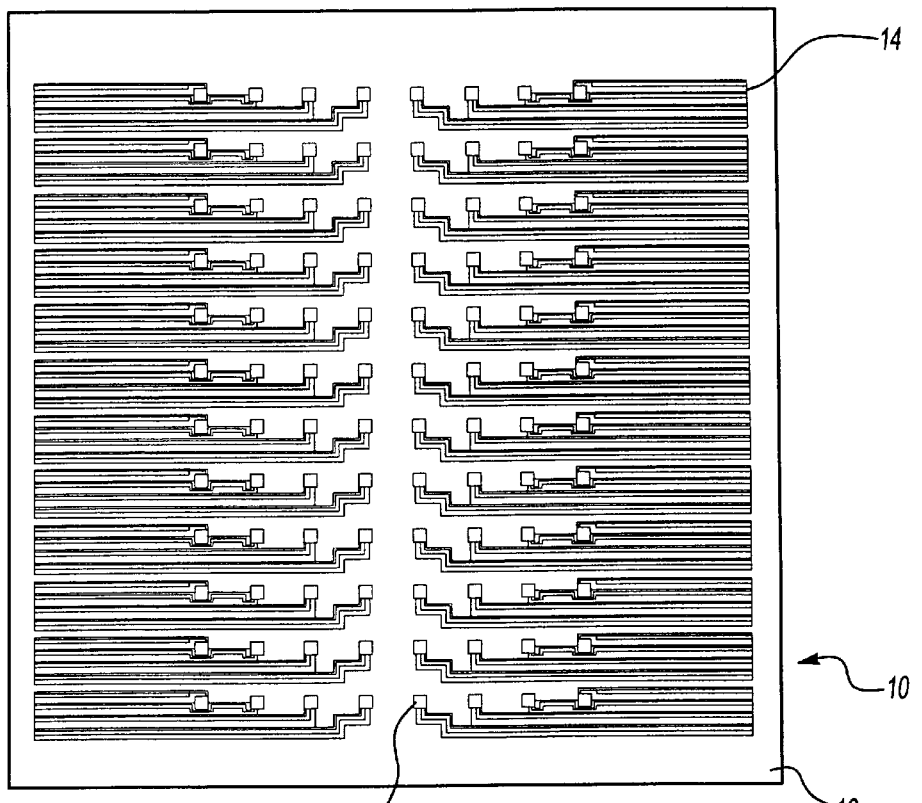
Figure 2D:
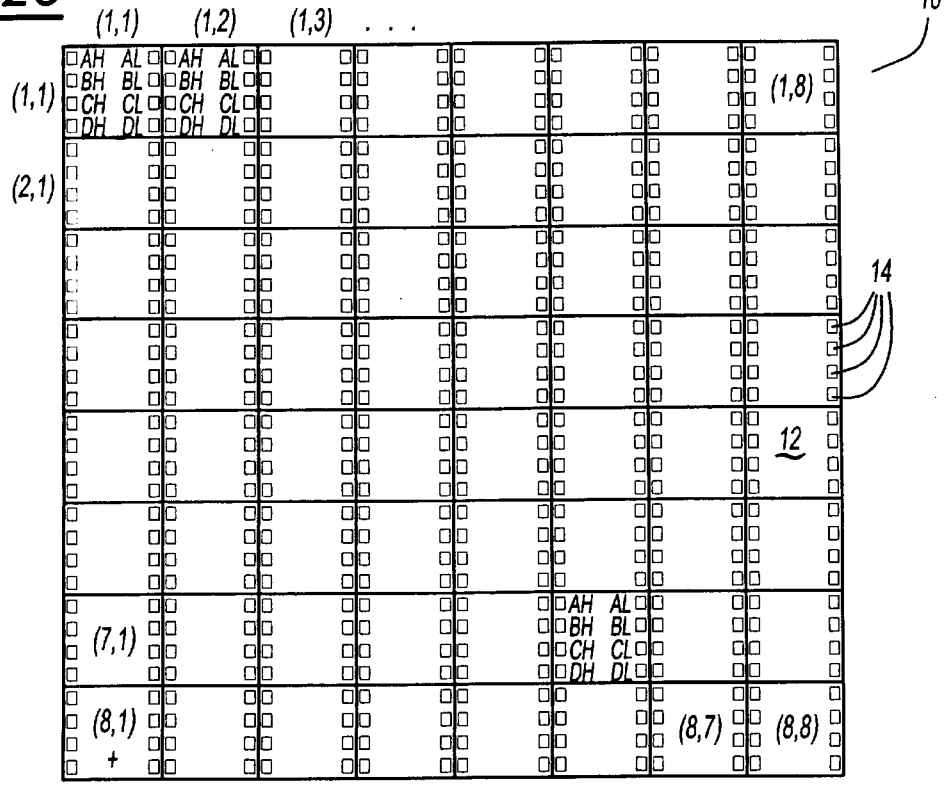

FIGS. 2A, 2B and 2D illustrate one example of a sensor array and contact pad layout pattern using an 8×8 square array with a 0.25-inch pitch (spacing between the centers of adjacent sensors in the array). This particular two-inch square sensor array is compatible with vapor deposition chamber equipment that is often used in combinatorial chemistry and combinatorial materials science applications.

Another widely used combinatorial configuration is an 8×12 rectangular array with a 9 mm pitch, shown in FIG. 2C. The specific sensor array configuration is selected to be compatible with, for example, the automated deposition equipment being used and/or the physical configuration of the material libraries being tested. A standardized sensor array configuration allows material deposition apparatus to deposit entire rows, columns or an entire library of samples on all of the sensors in the array simultaneously, which is generally more efficient than depositing materials one sensor at a time. The specific material deposition method used depends on the material properties being measured and the physical characteristics of the material itself. For example, in some thermal analyses, it is desirable to dissolve the material to be characterized in a solvent, deposit solution onto the sensor, and let the solvent evaporate to leave a film of material on the sensor's surface. For other materials, it may be more appropriate to place material that is in the form of a slurry or powder directly on the sensor. Sample thickness on the sensor may depend on the testing method, the sample itself or the method of sample deposition. Throughout this specification, the terms "thin" and "thick" may be used when referring to films, however, those terms are not meant to be limiting.

Referring to FIGS. 2A and 2B, the sensor array 10 includes a plurality of sensors 12 and a plurality of sensor contact pads 14 corresponding to the sensors 12. The specific micro-structure of the sensor 12 depends on the material property or properties that the sensor 12 is designed to measure. Sensors 12 that are designed to measure different properties have different micro-structures. More detailed descriptions of the actual sensor 12 structure are provided below in the Experimental Example sections with respect to sensors that measure specific material properties. To the naked eye, however, the sensors 12 may look like small pads or tiny wells, depending on the specific material characterization application, that are arranged on a planar substrate 16; the functional differences are within each individual sensor 12 at the microscopic level. More importantly, different sensor arrays 10, incorporating different sensors 12, will share a common array 10 and contact pad 14 format. The electronic wiring and interconnection devices for sending sensor data to and from the sensor array 10 are arranged into a configuration that is compatible with the sensor array 10 format. As a result, different sensor arrays 10 for use in the same materials characterization apparatus will have the same sensor locations and the same overall wiring patterns for electrical connections; different arrays 10 will look identical at a superficial level, even if they measure different properties. This sensor array 10 standardization allows arrays 10 that measure completely different material properties to be electrically contacted using a single interconnection device, which is in turn attached to a flexible electronic platform.

The sensors 12 and sensor contact pads 14 are formed on the substrate 16 in any selected array format that is desired. For example, they may be compatible with the material deposition machine being used. Any desired geometry can be achieved, such as lines, squares, rectangles, circles, triangles, spirals, abstract shapes, etc. Such geometric shapes can be considered to have either an open or closed shape with either straight or curved sides or both. Any number of sensors 12 can be used, including 5 sensors, 48, 96 or 128 sensors, and preferably from 5 to 400 sensors may be in one array 10. The material selected for the substrate 16 can vary depending on the application in which the sensor array 10 will be used, as will be explained by examples below. Possible substrate materials include, but are not limited to, silicon, silicon nitride, glass, amorphous carbon, quartz, sapphire, silicon oxide or a polymer sheet. For example, the polymer substrate may be a polyimide such as Kapton® from DuPont. Other polymer substrates may be used, including those selected from the group consisting of aramids (such as Kevlar®), polyester (such as poly (ethyleneterephthalate), oriented films such as Mylar®, or poly(ethylenenaphthalate)), epoxy resins, phenol-formaldehyde resins, polytetrafluoroethylene (such as Teflon®), polyacetal (such as Delrin(®), polyamide (such as Nylon®), polycarbonates, polyolefins, polyurethanes, silicones, polysiloxanes and the like. Other materials can also be used for the substrate 16. Substrates 16 used for thermal characterization and other tests requiring thermal isolation of small amounts of sample material should have the ability to be formed into a thin film or sheet that can withstand the temperatures at which the materials will be tested. In a thermal analysis application in which the sample is a thin film, for example, the portion of the substrate 16 that supports the sample is ideally between 0.1 and 25 micrometers thick or the same order of magnitude as the thickness of a material sample, to minimize the effects of the heat capacity and thermal conductivity of the substrate 16 in the test results without making the substrate 16 too fragile to work with easily. In short, the optimum dimensions of the substrate 16 will depend on the characteristics of the specific material chosen for the substrate 16 and the specific property or properties to be characterized by the sensor array 10.

The sensors 12 and sensor contact pads 14 are preferably formed on the substrate 16 via lithography. The specific number and design of the lithographic layers will depend on the characteristics to be measured and the particular sensor application. If possible, the number of layers is preferably as few as possible, for example less than four or five layers, to minimize the number of fabrication steps and reduce the overall cost of the sensor array. The number of lithographic layers can be kept to a minimum by creating sensors 12 that characterize only one or two material properties and also by eliminating on-board control circuitry within the sensor 12 itself, if desired. More specific sensor structures are explained in further detail below with respect to the experimental examples. Keeping the sensor array 10 manufacturing cost low makes disposability of the array 10 possible, if desired or necessary (e.g. after testing inorganic materials that may not be easily removed from the sensors). Further, if there is no on-board control circuitry that could be harmed under extreme conditions on the sensor array 10, the sensor array 10 can be cleaned after use by dipping the entire array structure into a solvent or acid or heating the sensor array 10 at a very high temperature to remove sample material residue. The cleaned sensor array 10 can then be reused. Of course, placing on-board electronics on the sensor array 10 or integrating the array with a circuit board having electronic components is also an option, if deemed appropriate for the application in which the array 10 will be used.

In one embodiment, eight sensor contact pads 14 are provided for each sensor, as shown in FIGS. 2A, 2B and 2D. For identification purposes, the eight pads can be divided into four pairs labelled A through D, with each pair having a H (high) contact pad and a L (low) contact pad. Using this labelling scheme, each sensor contact pad in the sensor array can be identified by an array position, a letter, and a H or L designation (e.g., (1,1)AH). Of course, other sensor 12 and sensor contact pad 14 configurations are possible as well as alternative sensor contact pad identification systems. Also, in this example, the sensor contact pads 14 are preferably spaced at a $\frac{1}{16}$ inch pitch with a 1 mm spacing in between adjacent columns of pads 14. This physical arrangement is particularly suited for coupling the sensor contact pads 14 to a printed circuit board 30 via elastomeric connectors, which will be explained in greater detail below. Other sensor contact pad 14 arrangements can also be used, depending on the specific manner in which the sensor array 10 will be electrically contacted and the specific application in which the sensor array 10 will be used, without departing from the scope of the invention.

Figure 3A:
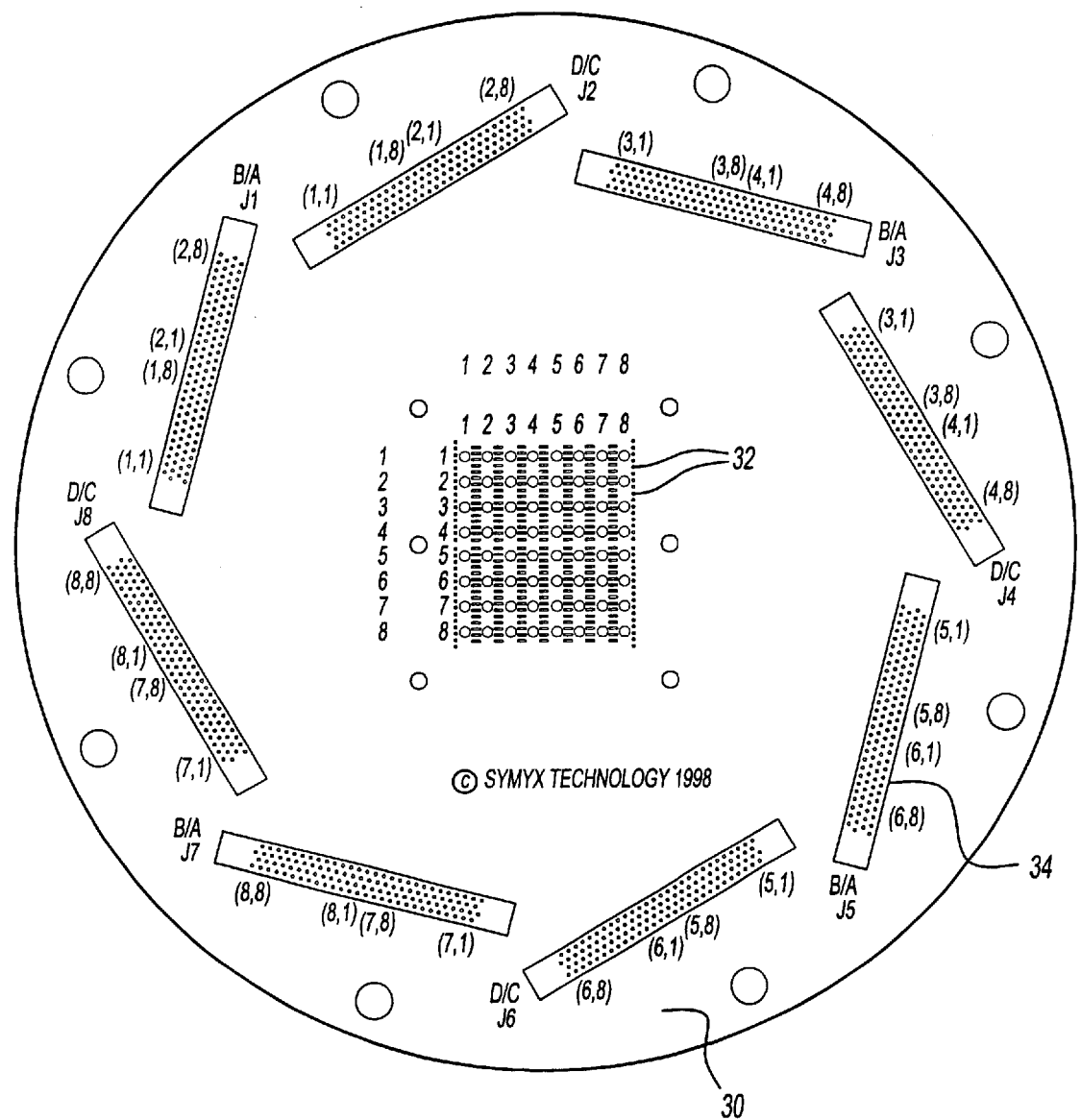
FIGS. 3A and 3B are examples of a printed circuit board in the invention.
Figure 3B:
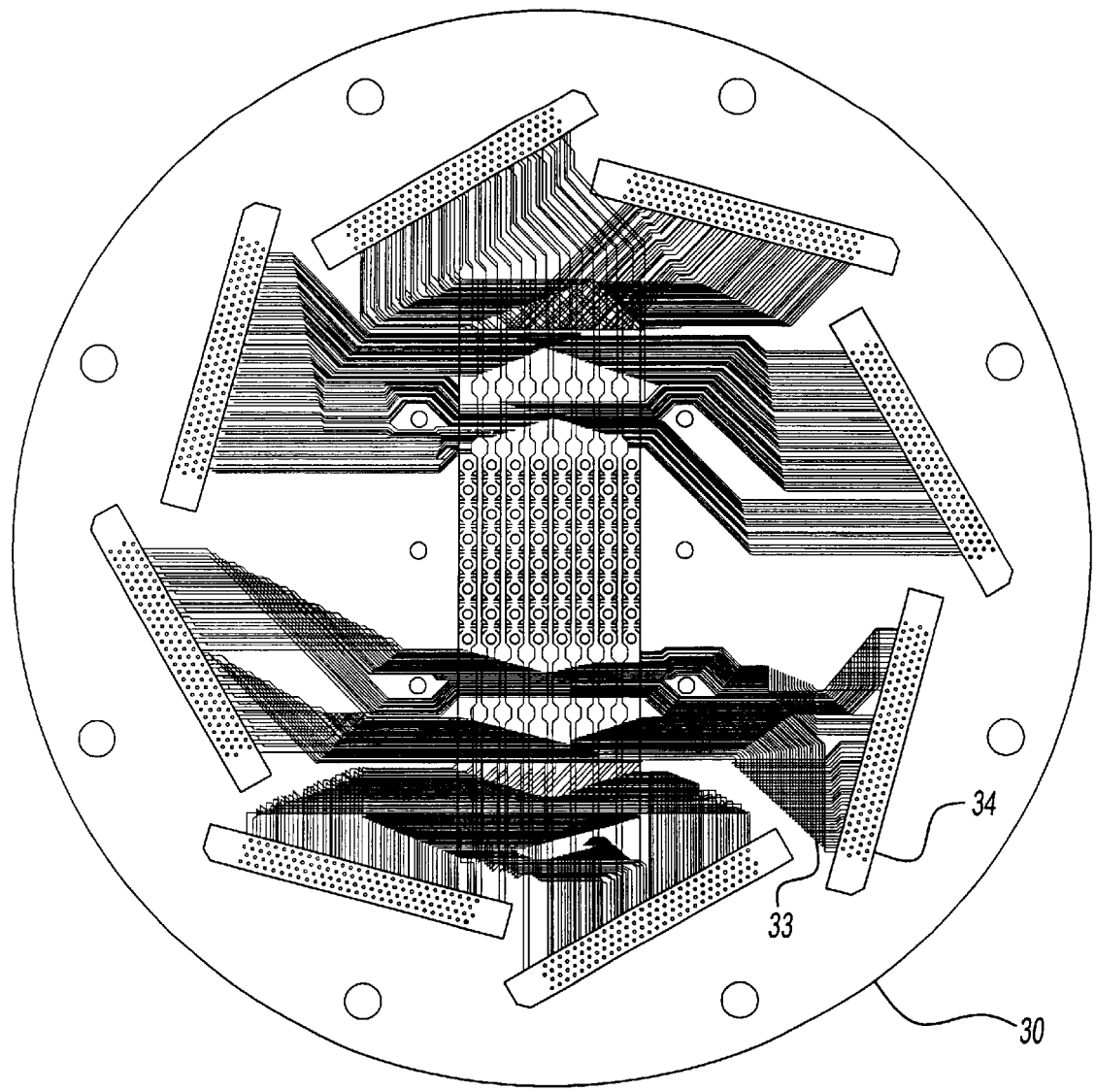

FIGS. 3A and 3B are top views of a specific embodiments of printed circuit board to be coupled with the sensor array 10 shown in FIG. 2A and 2B, and FIG. 4 shows an exploded view of one portion of an apparatus that connects the sensor array to the circuit board in the inventive materials characterization device. The circuit board used in the examples (except for the dielectric example) measures 11 inches in diameter and includes 8 layers of metallization. Gold was used for the top layer of metallization to for good electrical contact with elastomeric connectors. All eight layers are superimposed in FIG. 3B. Of course, this specific design can be modified by those of skill in the art without departing from the invention. Generally, the printed circuit board 30 preferably includes a plurality of board contact pads 32 having an arrangement which is a mirror image of the arrangement of the sensor array contact pads 14, such that when the sensor array 10 is connected to the printed circuit board 30, there is a one-to-one correspondence between the board contact pads 32 and the sensor contact pads 14. Tolerances in the positioning of the pads and trails of 0.001-inches can be easily attained with modem manufacturing techniques, permitting precise matching of the sensor and board contact pad patterns. The sensor contact pads 14 and the board contact pads 32, via leads 33 and connectors 34 that are disposed on the board 30, are the primary contact points through which the sensor array 10 connects with a flexible electronic platform, such as a computer and/or electronic test circuitry.

To connect the sensor array 10 to the printed circuit board contact pads 32, a plurality of Z-axis connectors 40 can be used, as shown in FIG. 4. The Z-axis connectors 40 create the electrical connection between the sensor contact pads 14 and the board contact pads 32. In the embodiment shown in FIG. 4, the Z-axis connectors are formed from rubber or other elastomeric strips containing conductive metal particles or wires for carrying current. These elastomeric conductors are preferably designed to conduct electricity in only one direction to prevent cross-talk between closely spaced contacts. Other possible connectors that can be used to couple the sensor contact pads with the board contact pads include cantilever or stick probes or other types of spring-loaded contacts, conducting adhesives, glues or epoxies, wire bonding, soldering, or direct contact between the sensor array and board contact pads 14, 32. Regardless of the specific type of structure, the Z-axis connectors 40 must create a reliable connection between the sensor contact pads 14 and the board contact pads 32, even when very closely spaced together, to ensure reliable coupling between the sensor array electronic platform without cross-talk between adjacent contact pads.

The Z-axis connectors 20 can be placed in a frame or positioning fixture 42 that may be attached to the circuit board 30, as shown in FIG. 4. This allows the sensor and board contact pads 14, 32 to be lined up with each other precisely and coupled through the Z-axis connectors 40 in a one-to-one relationship. The positioning fixture used with elastomeric connectors in the example experiments discussed below had a square cavity, 2.002-inch+/−0.001" tolerance, for precisely positioning of the sensor array 10, slots 41 to hold the connectors 40, and holes 43 for optical/atmospheric access. The connectors 40 in the example experiments discussed below were elastomeric connectors, such as Fujipoly "Zebra Silver" connectors, having dimensions of 1 mm wide, 2" long, and 5 mm high. A compression plate 44 can be used to provide additional security in the connection between the sensor and board contact pads 14,32, especially if the sensor array 10 and the printed circuit board 30 are not bonded together. The compression plate 44 is simply placed on top of the sensor array 10, secured in place with screws or other fasteners 46 and tightened until the sensor array 10, the Z-axis connectors 40 and the printed circuit board 30 are pressed firmly together. The compression plate 44 may have a plurality of holes 48 having the same configuration as the sensors 12 in the sensor array 10 to allow optical testing of the sensor array 10, either alone or in conjunction with the electrical characterization according to the present invention, if desired, and permit gas exchange or evacuation. Holes 49 may also be provided in the printed circuit board 30 for the same purposes.

The printed circuit board 30 may provide the primary electronic link between the sensors 12 and any peripheral devices used to control and monitor the sensor array, such as the components in the flexible electronic platform. The printed circuit board 30 also can, in many cases, be considered part of the signal routing equipment (as opposed to being considered a part of the sensor array 10). In the embodiment shown in FIG. 3A and 3B, as noted above, the printed circuit board 30 has a plurality of connectors 34 arranged around the board's 30 periphery, leaving enough space in the center area of the printed circuit board 30 for positioning the sensor array 10. The connectors 34 on the printed circuit board 30 are preferably standard multiple-pin connectors so that a commercially available ribbon cable wire assembly can route signals to and from the sensor array 10 or couple the printed circuit board 30 with peripheral devices, such as a multiplexer and flexible electronic platform. The illustrated structure, which was used in the examples discussed below, is a Robinson-Nugent P50E-100STG 100-pin connector that is compatible with the inputs of the multiplexer, but any other multiple-pin connector can be used without departing from the spirit and scope of the invention. Each board contact pad 32 has an associated lead 33 that extends from the board contact pad 32 to a pin on the connector 34. It should be noted that the connection between the printed circuit board 30 and the electronic platform need not be a physical connection, such as a ribbon cable, but can also be any type of wireless connection as well as long as signals can be transmitted between the sensor array 10 and the electronic platform.

Figure 6A:
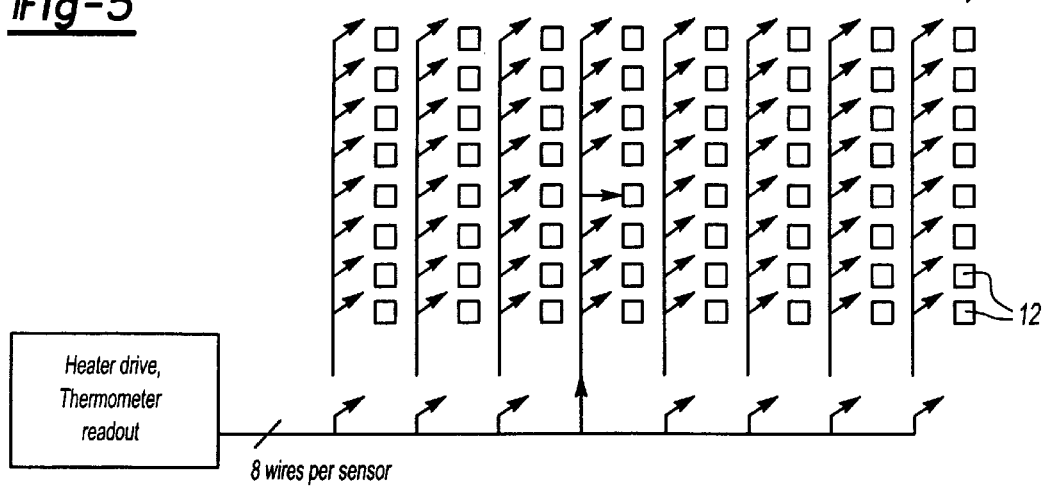
FIGS. 6A and 6B are representative diagrams illustrating two contemplated sensor addressing schemes in the invention.

A multiplexer may be included in the apparatus as signal routing equipment linking the sensor array 10 and the electric platform or test equipment being used, which is schematically represented in FIG. 6A. The multiplexer used in the experimental examples discussed below was an Ascor model 4005 VXI multiplexer module, containing four custom Ascor switch modules (model 4517). Each switch module contains 64 2-wire relays, in eight groups of eight relays per group, for a total of 128 input connections per module (512 connections total, corresponding to the number of contact pads on the sensor array). This design was chosen because it was easy to integrate with the embodiment having an 8×8 array with 8 contact pads per sensor. Thus, obviously, different designs may be used without departing from the invention. Each switch module also has four output connections, which can be connected to different input connections by closing selected relays under computer control. The signal routing equipment shown in FIG. 6A emphasizes simultaneous contact and connection of all of the sensors 12 to multiplexer inputs, with sensor selection being conducted by closing selected switches in the multiplexer.

A preferred embodiment facilitates attachment of standard electronic test and measurement equipment to the outputs of the signal routing equipment. For the experimental examples discussed below, there were eight terminals, one for each contact pad 14 on the sensor 12. The outputs were routed to a panel containing standard panel-mounted BNC coaxial connectors. However, again this design can be modified by those of skill in the art without departing from the invention. Generally, a given pair of signals (e.g. AH and AL) can either be connected to a center conductor and shield a single BNC terminal, which is electrically isolated from the mounting panel, or be connected to the center conductors of two separate BNC terminals whose outer shields are connected to the system ground. This permits either single-ended or true differential connections to the sensors, with the connection mode chosen manually for each pair of leads (e.g. A, B, C, and D) by means of a toggle switch. Thus, when a single sensor 12 is selected, the eight contact pads 14 of the selected sensor 12 can be easily accessed from the panel of BNC connectors, using virtually any desired piece of electronic test and measurement equipment. Other types of terminals can of course be used.

For the apparatus used in the examples, thirty-two analog backplane connections were provided between multiple 4517 switch modules in the common 4005 multiplexer module, permitting highly flexible configuration of the multiplexer. In addition to permitting selection of one sensor at a time, the backplane connections permit selection of one sensor from each row at a time, with the outputs being made available on one or more 32-terminal output modules, which are also housed in the 4005 multiplexer module and are connected to the analog backplane. The flexible multiplexer design also permits the multiplexer to be used with arrays larger than 8×8 by permitting additional switch modules to be inserted into the housing and connected to the common backplane.

Again for the example experiments, the Ascor 4005 multiplexer module was housed in a Hewlett-Packard model HP E8400A 13slot VXI mainframe. Communication with a computer was through a National Instruments GPIB-VXI/C interface module, which allows control of the VXI system via the computer's GPIB interface. The multiplexer was controlled from the computer by sending appropriate commands to the GPIB-VXI/C interface module. The software for controlling the multiplexer preferably permits operation in two different modes. In both cases, a graphic representation of the sensor array 10 was shown on the computer screen in the form of an array of "buttons." In manual operation mode, the user selects one or more sensors by clicking on the corresponding buttons and then instructing the computer to close the appropriate switches. All eight connections to the selected sensor or sensors 12 are then closed, while any previously closed connections on non-selected sensors 12 are opened.

In automatic or scan operation mode, using the control software the user again selects a group of sensors by clicking on the corresponding buttons. The computer then closes the switches to the first sensor, performs a measurement procedure, and opens the switches to the first sensor. The procedure is repeated for all of the sensors selected by the user, scanning across each row from left to right and moving from the top row to the bottom. Relays are not closed and measurements are not performed on unselected sensors. This software can be changed to accommodate preferred modes of operation, including running in parallel.

Once a sensor 12 is routed to the multiplexer output, many different commercially available electronics components may be connected to the sensor array 10 to input and output signals to and from the sensor 12. For example, if the sensor array is designed to measure resistance, a resistance meter that has one input is connected to the multiplexer output and can measure the resistance of any of the sensors 12 that are connected to the multiplexer inputs. The multiplexer allows a user to select any one of the sensors 12 on the array 10 and output data related to the resistance properties of the sample material containing the selected sensor 12.

Figure 6B:
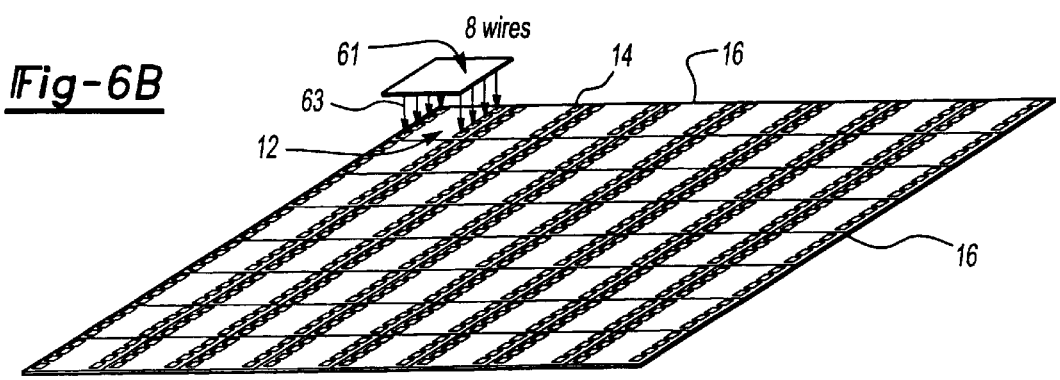

Alternative signal routing equipment is illustrated in FIG. 6B. A probe assembly 61 having probes 63 disposed thereon in an arrangement that matches the sensor contact pad arrangement 14 on one or more sensors is position over a selected sensor 12 via a three-axis translation stage. The three axis translation stage is preferably controlled by motors under computer control. The probe assembly 61 itself may be moved, or the substrate 16 may be moved to position the assembly 61 and the substrate 16 relative to each other. To select a sensor 12, the probe assembly 61 is positioned over the selected sensor 12 and moved toward the substrate 16 to make electrical contact with the selected sensor's 12 contact pads. Wiring from the probe assembly connects the selected sensor or sensors to the electronic platform. The specific technology used for positioning the probe assembly 61 can be any positioning mechanism known in the art. The advantage of the sensor selection and signal routing system shown in FIG. 6B is that it largely reduces or eliminates the need for a circuit board, multiwire cables, and multiplexer.

Figure 5:
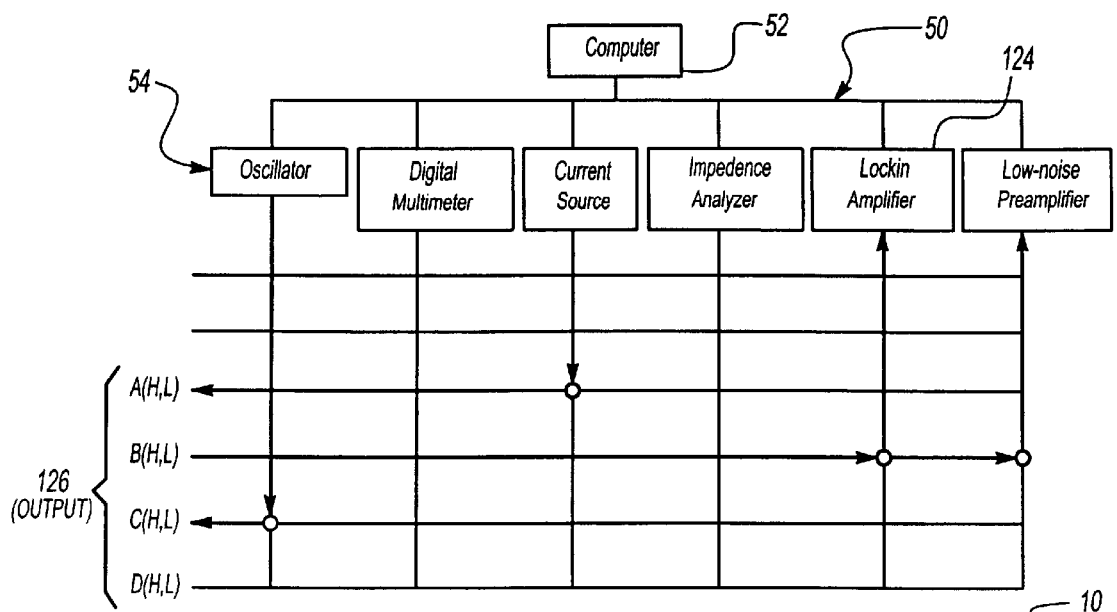
FIG. 5 is a representative diagram of a matrix switch in the invention.

FIG. 5 illustrates one possible configuration for a generic flexible electronic platform that can be used in conjunction with the sensor array of the present invention. In this example, the outputs from the signal routing means, such as the multiplexer, are connected to a matrix switch 50 that is controlled by a computer 52. The matrix switch 50 has a plurality of electronic test measurement instruments 54 that can be coupled to any or all of the multiplexer outputs. A user can select which instruments to connect to particular sensors 12 in the sensor array 10 by either inputting instructions into the computer 52 to open and/or close the matrix switch 50 connections by opening and closing the connections manually, including manually rerouting cables that attach outputs to electronic inputs. Thus, this particular type of flexible electronic platform can output and read many different signals required for measuring many different material properties with different sensors, simply by changing the connections within the matrix switch 50.

Because the sensors 12 can be accessed using off-board circuitry, the inventive structure allows great flexibility in the manner in which the sensors are addressed. If a multiplexer is not used to control sensor addressing, and if a separate electronics channel is provided for each sensor as the signal routing means, then all of the sensors 12 in the array 10 can be monitored simultaneously, allowing rapid parallel characterization of entire material libraries. If a multiplexer is used, any channel from any sensor 12 can be made available for input or output via its corresponding multiplexer terminal, and simultaneous but separate of addressing individual sensors in different rows in the array 10 is also possible. As illustrated in FIG. 6A, the computer 52 can also be programmed to conduct rapid serial measurement (addressing one sensor 12 at a time), addressing all sensors 12 in a selected group simultaneously (such as heating each row to a different temperature to study thermal processing conditions), and simultaneously addressing one sensor 12 from each row (combined serial/parallel sensor measurement). All of these sensor accessing schemes can be implemented electronically, through software instructions to the multiplexer, without physically reconfiguring or rewiring any part of the apparatus because of the apparatus' modular construction, the interconnection structure, and the flexible electronic platform. Of course, if desired, any or all of the components (e.g., the multiplexer, the printed circuit board 30, the sensor array 10, and the electronic test circuitry from the electronic platform) can also be integrated in various ways to construct a more customized materials characterization unit.

An alternative structure for the sensor array 10 is shown in FIGS. 2C and 7. In certain applications, such as characterization of liquid materials, it is not desirable to have the contacts between the sensor array 10 and the printed circuit board 30 located in the same vicinity as the sensors 12 themselves. The liquid materials would tend to contaminate the contact pads 14, 32, reducing the integrity of the interconnection between the sensor array 10 and the printed circuit board 30 and preventing reuse of the interconnection hardware, such as the Z-axis connectors 40. To overcome this problem, the sensor array 10 shown in FIGS. 2C and 7 directs the leads from all of the sensors 12 to the edge of the substrate 16, away from the actual sensor sites. Contact between the sensor array 10 and the printed circuit board 30 is made at the edge of the substrate 16, either with Z-axis connectors 40 as in the sensor array described above or with probe cards or probe arrays 70, as shown in FIG. 7. Cantilever probes 72 on the probe array 70 provide the electrical link between the sensor array 10 and, for example, the multiplexer, the flexible electronic platform, or some other peripheral device.

Because the sensors 12 in the sensor arrays 10 shown in FIGS. 2C and 7 are relatively flat and have their top surfaces physically exposed, a rubber gasket (not shown) containing holes in the same locations as the sensors can be placed on top of the sensor array 10 to hold liquids in place over the sensors 10. The gasket can be pressed or bonded to the plate while the traces connecting the sensor array 10 to the printed circuit board 30 can still be run along the substrate 16 to its edge. Further, because there is a clear optical path to the sensors 12 from an overhead vantage point, the sensor array 10 can be used in conjunction with a camera or other optical sensing device, allowing even more material properties to be measured simultaneously. For example, if the sensors 12 in the array 10 are designed to measure the progress of a curing process via measurement of material dielectric constants, using a camera in conjunction with the materials characterization device of this invention allows detection and measurement of exothermic properties and/or temperature changes at the same time as measurement of the dielectric constant, further increasing the number of characteristics that can be measured at one time. See WO 98/15805, incorporated herein by reference, for a discussion of optical screening techniques.

An alternative structure for the present invention is shown in FIG. 8. In this embodiment, the individual sensors 12 are cut apart and mounted onto individual sensor plates 80 to form "dipsticks" 82 that preferably extend vertically from the substrate 16.

The spacing and format of the dipsticks 82 may follow a conventional combinatorial chemistry format, such as an 8×12 array with 9 mm spacing, so that all of the dipsticks 82 in the array 10 can be dipped into standard combinatorial chemistry wells 84 simultaneously, as shown in FIG. 8. In a preferred embodiment, the wells 84 contain solutions comprising the materials to be characterized dissolved in a solvent. Once the dipsticks 82 are dipped into the wells 84 and removed, the solvent is allowed to evaporate and coat the sensors 12 with the sample material. Input and output signals are then sent to and from the sensors 12 in the same way as described above to characterize the material properties. The liquids in the wells can also be directly characterized as the while the sensors are immersed in the wells.

Because the materials characterization system of the present invention has a modular, flexible structure, many different material properties can be monitored simply by changing the sensor structures in the sensor array 10 and attaching different electronic components to the array outputs or signal router outputs as needed, depending on the specific material property to be measured. Thus, the same interconnection method and signal routing equipment may be used for all types of measurements, where the only components that need to be changed are the sensor array 10 itself ("plug-and-play" operation) and possibly some specific electronic test circuitry in the electronic platform. This is much less expensive than purchasing a separate machine for measuring each property. Also, as can be seen below, the sensor arrays 10 themselves may be reusable in certain applications, reducing expenditures for testing even further. The measurements obtained from the sensors 12 in the sensor array 10 of the present invention can be directly correlated to known testing results. In other words, the results obtained from the sensor arrays 10 correlate with results obtained from conventional materials characterization methods. This advantage of the present invention will be highlighted in greater detail with respect to the experimental examples described below.

Thermal Analysis Background

Thermal analysis is one of the most generally useful techniques of materials analysis, particularly measurements of heat capacity. In many cases for thermal analysis, it is important that the sample being analyzed is thermally isolated from its environment to a large degree. Thermal isolation insures that heat flows into and out of the sample and the associated changes in the sample temperature may be accurately determined and are not masked by much larger heat flows associated with other objects, such as the sample holder or substrate, heater and thermometer, etc. Samples produced in combinatorial materials synthesis may consist of films, created by physical vapor deposition techniques (evaporation, sputtering, etc.) or by deposition of a liquid solution or suspension and subsequent evaporation of the solvent. The samples preferably have small lateral dimensions (e.g. 1 mm or less), to allow more samples to be deposited on a given area. A sensor designed for thermal analysis of combinatorial libraries must therefore allow accurate measurements to be made on very small samples that are packed closely together on a substrate. Although thermal isolation of minute samples initially poses a challenge, it also offers an advantage in that the thermal time constants for internal equilibration of the sample, heater, and thermometer are greatly reduced, permitting more rapid measurements to be made.

Thermal isolation of small-area thin film samples may be most easily achieved by using a thin film of low thermal conductivity material to support the sample, where the support's thickness is comparable to or less than that of the sample. The heat capacity and thermal conductance of the support are thus comparable to that of the sample film, can be independently measured, and can be subtracted from measurements made with a sample present. Further isolation during the measurement can be achieved by use of various modulated or pulsed heat capacity measurement methods, which will be discussed below.

Figure 9B:
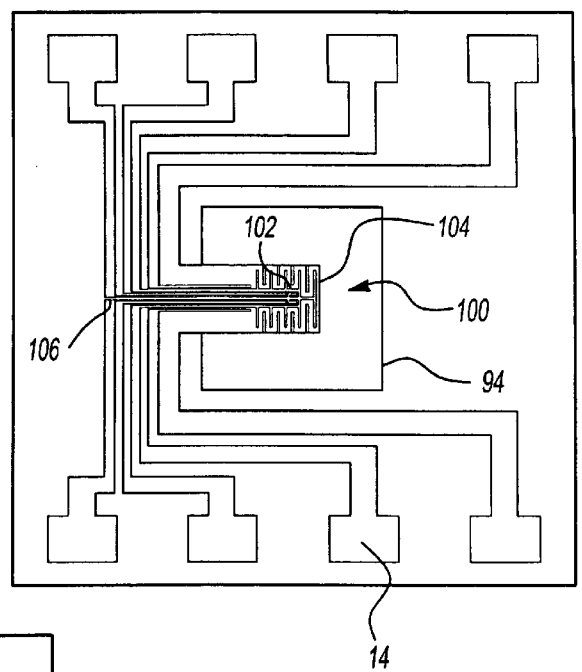
Figure 9C:
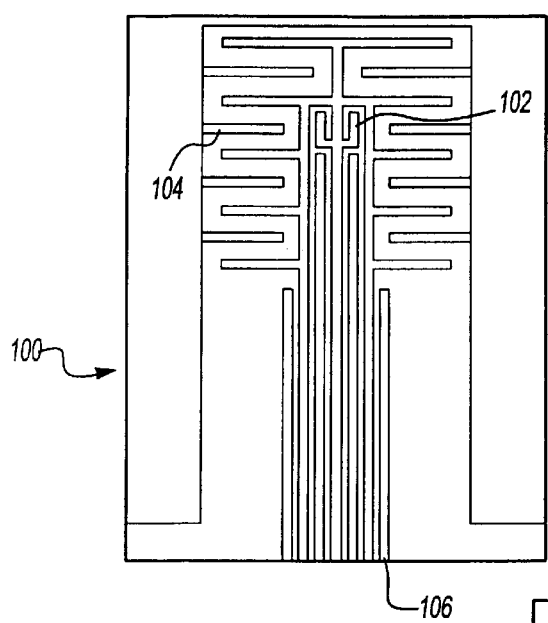

Issues affecting the design of a thin film calorimeter are the materials used for fabricating the substrate and thin support membrane, the materials used for fabricating the heater and thermometer, the geometry of the heater and thermometer, membrane, sample, and substrate as they affect the temperature profile and transport of heat, and the way in which the sensors can be connected to an interface so that useful information can be obtained from the sensors. FIGS. 9A through 9C illustrate preferred sensor structures for use in thermal analysis applications with thin film samples. Although the figures illustrate the structure of one individual sensor, it is understood that all or part of the sensors in the sensor array can be manufactured on the substrate 16 simultaneously.

FIG. 9A is a preferred thin-film structure for conducting thermal analysis of a thin-film sample 90. A micro-thin membrane 94, which supports the sample material 90, is preferably made of silicon nitride ($Si_3N_4$) on a silicon wafer substrate 92. The substrate 92 preferably has a plurality of membranes 94 that are formed thereon in the desired sensor array arrangement. To form the membranes 94, a thin film of silicon nitride 95 is deposited on the top and the bottom surfaces of the silicon wafer 92. The thickness of the silicon nitride film 95 is preferably between 500 angstroms and 2 microns, as this thickness can be easily produced by chemical vapor deposition and other techniques; it also corresponds to typical thickness' of the thin film samples 90 to be studied. The desired membrane pattern is then created on the bottom surface of the silicon wafer 92 to open up "windows" 96 in the silicon nitride film 95, exposing the silicon 92 at selected locations. The entire wafer structure is dipped into an etching solution, such as potassium hydroxide, to erode or etch away the silicon 92 exposed through the windows and form the structure shown in FIG. 9A. Regardless of the specific etchant used, it should etch silicon but not etch silicon nitride. Because of silicon's crystal structure, the etching process forms a well 97 with sloping walls through the silicon layer 92 and which stops at the top silicon nitride layer 95. The resulting structure is a suspended, micro-thin silicon nitride membrane 94 supported by silicon 92. The well 97 makes the sensor array structure particularly suited for depositing films from solids dissolved in a solvent, as a drop of the solvent can be held in the well 97 during drying. The well 97 can also contain liquids which are being tested.

FIGS. 9B and 9C illustrate one possible heater/thermometer pattern 100 that can be printed on the membrane 94 to form a complete thermal analysis sensor. As can be seen in the figure, the preferred heater/thermometer pattern 100 is designed so that the thermometer portion 102 is much smaller than the heater portion 104 and so that the thermometer 102 is located in the center of and surrounded by the heater 104. The heater 104 is still sufficiently small so that the edges of the heater/thermometer pattern 100 are isolated from the edges of the membrane 94. These design features give the sensor 12 several desirable properties that make it useful for conducting rapid heat capacity measurements on thin film samples. The time constant for equilibration of the heater 104 with the thick part of the substrate 92 (beyond the edge of the "window") is much longer (slower) than the time constant for internal equilibration of the portion of sample 90 adjacent to the heater 104 and thermometer 102, since the time constant is proportional to the square of the distance over which the heat must diffuse. The temperature profile across the heater 104 may to some extent have a non-uniform dome-shaped profile due to heat flow from the center of the heater 104 outwards; placing a small thermometer 102 in the center of the heater 104 allows measurement of the temperature in a region whose temperature is much more uniform than the temperature of the entire heater 104.

The heater/thermometer 100 is preferably printed on the flat side of the membrane 94 via lithography so that the sample 90 can be deposited on the membrane 94 within the "well" portion 97 and be characterized without actually touching the heater/thermometer pattern 100. The membrane 94 prevents direct physical contact between the heater/thermometer 100 and the sample, yet is still thin enough to create intimate thermal contact between the heater/thermometer 100 and the sample 90 and allow heat to conduct through the membrane 95 to warm the sample 90 and measure its thermal characteristics. This feature is particularly useful when characterizing metals, where direct physical contact between the heater/thermometer 100 and the sample 90 would create a short circuit in the heater 104. Heater/thermometer leads 106 are connected to the sensor contact pads 14 or are otherwise configured for coupling with the flexible electrical platform so that the power input and the sample's temperature can be monitored and controlled electrically. Thus, it can be seen that in some embodiments, coatings may be used on the sensors to protect the sensors from the samples or vice versa.

The specific configuration for the micro-calorimeter array and the system architecture for coupling the sensors 12 in the array 10 to the electrical platform can be any structure desired by the user as long as electrical signals can be sent to and read from each individual sensor 12 in the array 10. The micro-calorimeter used in the example experiments was custom manufactured so that the substrate 92 was a 0.5 mm silicon wafer, with 0.5 µm of low-stress LPCVD silicon nitride deposited on both sides. The silicon nitride membranes 94 were 2 mm squares and prepared by known procedures. To produce the metallization patterns, a liftoff procedure was used. Photoresist is spun on to the front side of the wafer, and is patterned by photolithography using a stepper. 50 Å of Ti was then deposited on the photoresist and the exposed portions of the substrate, followed by 2000 µ of Pt. The Ti layer was added for adhesion purposes. The photoresist was then dissolved, leaving metal in the desired pattern on the substrate. In the embodiment of the heat capacity sensor used in the examples, the heater 104 consists of a serpentine pattern, with 60 µm lines separated by 20 µm spaces. The thermometer 102 is a smaller area serpentine pattern, with 20 µm lines and 20 µm spaces. Following liftoff, the wafer was cut into the form of a square measuring 2.000"+/−0.001" precision, using a dicing saw. Accurate dicing of the wafer is needed for accurate positioning of the wafer relative to the circuit board, using the positioning frame. A dimension of 2" was chosen to allow the substrates to be inserted into combinatorial vapor deposition equipment.

An alternate material for the substrate is a polymer sheet. A particularly suitable polymer is a material called Kapton®, which is manufactured by DuPont. Kapton is thermally stable and can withstand temperatures up to 350–400 degrees C. without deterioration. Kapton is often sold in sheets ranging from 6 microns thick to 100 microns thick, and the heater/thermometer design, such as that shown in FIGS. 9B and 9C, can be printed directly onto the film via lithography or other techniques. To suspend the Kapton® sheet when conducting thermal analysis, the contacts can be printed such that they are all at the edges of the sheet, as shown in FIGS. 2C and 7, and the sheet can be stretched and clamped at the edges to connect the contacts on the sheet with corresponding contacts associated with the flexible electronic platform. If the samples are not electrically conducting, then the entire side of the sheet opposite the side containing the sensors can be covered with a layer of metal, which can be used as a blanket heater for heating all of the samples simultaneously, either via a DC signal or a modulated signal. As noted above, the inventive structure provides enough flexibility so that selected samples can be heated individually, simultaneously, or in any grouped combination simply by changing the electronic signals sent by the electronic platform.

Figure 10:
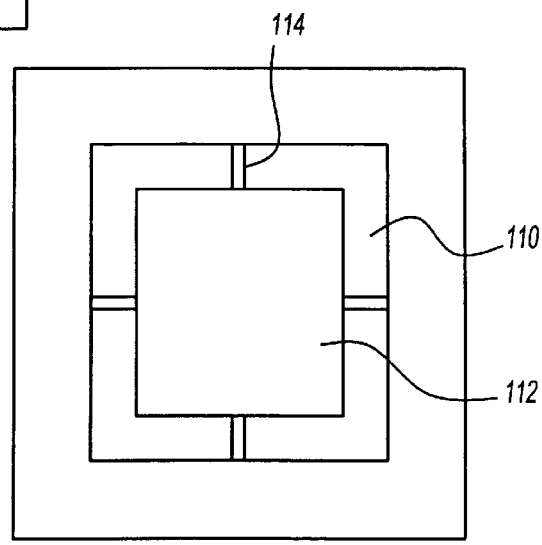
FIG. 10 illustrates an alternative thermal analysis sensor substrate structure.

In applications where larger amounts of material are available for analysis, e.g. samples which may be 10's to 100's of micrometers thick, it may be possible to use thicker substrates. In these cases, thermal isolation can be improved by using substrates with low thermal conductivity, such as glass, or by micromachining a gap or "moat" 110 around a sample support 112, which is spanned only by microbridges 114 of material, as illustrated in FIG. 10. The heater/thermometer pattern may be printed on the sample support 112. The microbridges 114 hold the sample support 112 in place on the substrate while minimizing heat leakage, and also act as supports for wires which must pass into and out of the sensor for coupling with the electronic platform.

EXPERIMENTAL EXAMPLE
Thermal Analysis of Polymers and Metal Alloys

The modular sensor array structure described above is particularly useful for rapidly measuring thermal properties of combinatorially synthesized libraries of polymers. The predominant use of heat capacity measurements with polymers is for the determination of the temperatures at which phase transitions occur and the identification of the types of phase transitions occurring (generally either glass transitions or melting points). This information can then be used in two general ways.

In some specific cases, it is desirable to have a phase transition occur at a particular temperature, and the goal of combinatorial synthesis might in part be to tune the polymer's physical properties until that value is achieved. For example, the glass transition temperature is an important parameter for the polymer particles used in latex paints, as it strongly affects how the latex particles will coalesce and form a film under given environmental conditions. A latex for a given coating application may have to fulfill many other conditions as well, related to properties such as adhesion and weatherability.

It is a common practice to try to achieve several desirable properties simultaneously by making random copolymers, containing an essentially random sequence made from two or more different monomers. The types and numbers of monomers used and their relative proportions can be varied in many different combinations, to attempt creating a polymer that simultaneously fulfills all of the desired criteria. However, adding a monomer that improves adhesion may reduce the glass transition to an unacceptable value, for example. Thus, being able to rapidly measure the glass transition temperature (in addition to other properties) for many hundreds of random copolymers allows the balancing of different physical properties to be done much more rapidly.

Figure 11A:
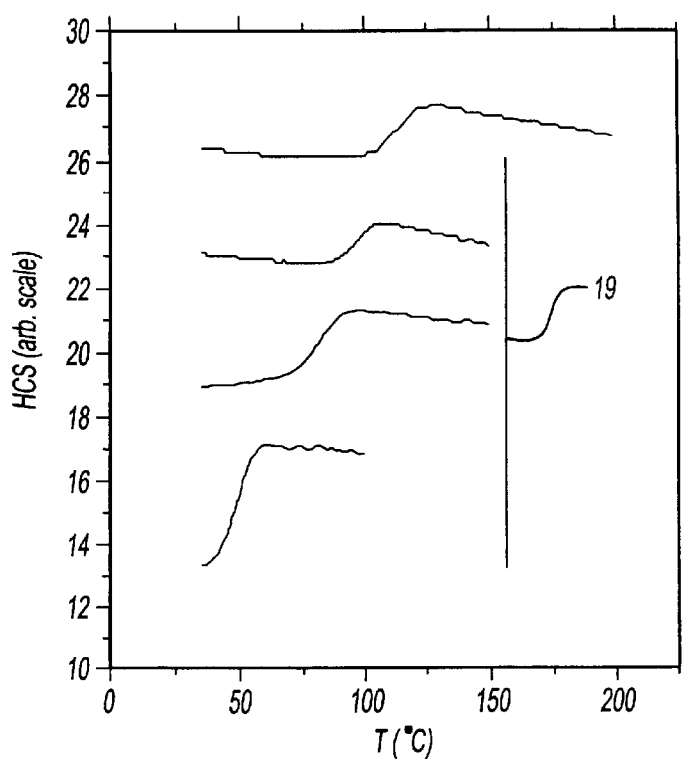
FIGS. 11A through 11F are sample traces of thermal analysis scans conducted according to the present invention.

An example is shown in FIG. 11A, where the glass transitions have been determined for a series of styrene-co-butyl acrylate random copolymers with different styrene contents, using the specific details discussed above. The random copolymers were synthesized by Atom Transfer Radical Polymerization (ATRP) at 140 C. for 15 hours, using CuCl with two equivalence of 4,4'-dinonyl-2,2'-bipyridine (dNbpy) as the control agent and (1-chloro)ethyl benzene (PhEtCl) as the initiator. The monomers styrene (S) and n-butyl acrylate (BA) were combined to make 11 solutions ranging from 100% S to 100% BA in steps of 10 volume %. A catalyst stock solutions was made in toluene by combining 1 part PhEtCl with 1 part CuCl and 2 parts dNbpy. For each of the 11 monomer stock solutions were set up five polymerizations with varying ratios of monomer to initiator, by varying the amount of catalyst stock solution added. This led to a 55 element array of random co-polymerizations that varied in the x-axis by the composition of monomers, and in the y-axis by the theoretical molecular weight (ranging from 10,000 to 50,000).

The samples in the example were chosen from the styrene-rich portion of the library, in order to produce Tg's above room temperature. The example of the inventive apparatus and method described here does not contain a means for cooling samples below room temperature; however, as is obvious to anyone skilled in the art, this can be accomplished easily in many different ways. The molecular weight of the polymers used was approximately 30,000 gm/mol. The polymers were dissolved in toluene at room temperature to a concentration of approximately 2%. Small drops (approximately 5 $\mu$l) of the solutions were manually pipetted onto the sensors, and allowed to dry in air until a film was formed. The heat capacity data shown in FIG. 11A were obtained using the inventive apparatus and method, following the "3$\omega$" measurement procedure, which is discussed below.

The glass transitions of the polymers can clearly be observed as a "step" in the heat capacity vs. temperature data. This is identical to the type of behavior observed using traditional differential scanning calorimetry to measure the heat capacity, and the data are of entirely comparable quality with respect to the sharp definition of the feature associated with the glass transition. The glass transition of polystyrene occurs near 100° C., in fair agreement with known results. It should be noted that these data were taken using an approximate calibration for the temperature sensor; improved calibration procedures will naturally yield more quantitatively precise values for Tg.

In addition, the glass transition temperature Tg can be seen to clearly decrease to lower temperatures with increasing butyl acrylate incorporation. This is entirely in accord with the known behavior of random copolymers, which typically show a glass transition temperature at a value intermediate between that of the pure component polymers (a 100% butyl acrylate polymer would have a glass transition temperature Tg of approximately −75° C.). However, the total time required to acquire this data using the inventive method is less than 2 minutes. Similar measurements using a conventional differential scanning calorimeter would take several hours or more.

Another example in which the precise value of a phase transition temperature is important is in the area of thermally responsive polymers, including polymers with crystalline side chains, liquid crystallinity, etc. Thermally responsive polymers are important to a wide variety of applications. Thermal measurements on polymers are also important in determination of a polymer's performance under different environments, including solvent, vapors, humidity, radiation, oxidation and the like. For example, the sample polymers may be tested after exposure to a certain environment or may be tested while being exposed to the environment.

Even more generally, however, information about phase transitions can give a great deal of insight into the chemical and physical structure of the polymer being studied, which in turn can be related either to the success or failure of a particular synthetic strategy, or to the suitability of the material for applications involving properties other than the melting or glass transition temperatures. Thus, thermal analysis is extremely useful within a combinatorial polymer synthesis program, as it allows a scientist to rapidly assess variations in polymer physical properties due to different catalysts, process conditions, etc, as well as to assess whether or not a polymer with a desired chemical composition or architecture has in fact been synthesized. The following examples will illustrate these points.

Even in the case of polymers made from a single monomer (e.g. ethylene), the physical properties of the polymer will vary tremendously depending on the architecture of the polymer, e.g. the molecular weight, and the degree and type of branching. For example, high density polyethylene (HDPE) and paraffin (wax) are chemically similar, but differ in their molecular weights and the amount of bridging between crystallites. The greater number of chain ends in paraffin severely disrupts the crystalline packing of the chains, in comparison to HDPE, leading to vastly inferior mechanical properties. The difference in physical properties is also directly manifested in a lower melting point for paraffin in comparison to HDPE.

Other factors which result in a reduced melting point are branching, and comonomer incorporation. Branching not only reduces the value of the melting point, but also reduces the total degree of crystallinity. Crystalline polymers in fact consist of both crystalline domains, or crystallites, and amorphous regions between the crystallites due to chain folding and chain ends. Generally, the greater degree of branching, the larger the amorphous fraction of the polymer. The amorphous regions display a glass transition, and by measuring the heat capacity signals associated with both the glass transition and the melting point, one can obtain information on the degree of crystallinity of the polymer, which in turn strongly affects the mechanical properties of the polymer. Similar considerations apply for polymers which incorporate comonomers.

Thus, in evaluating combinatorial libraries of ethylene catalysts, a rapid determination of the melting point and degree of crystallinity can give a good qualitative picture of what type of polyethylene is being produced by the catalyst. This adds a great deal of information to lower level screens such as the degree of catalyst activity and the polymer molecular weight, information which is more closely related to the end uses of the polymer produced by a given catalyst.

Figure 11B:
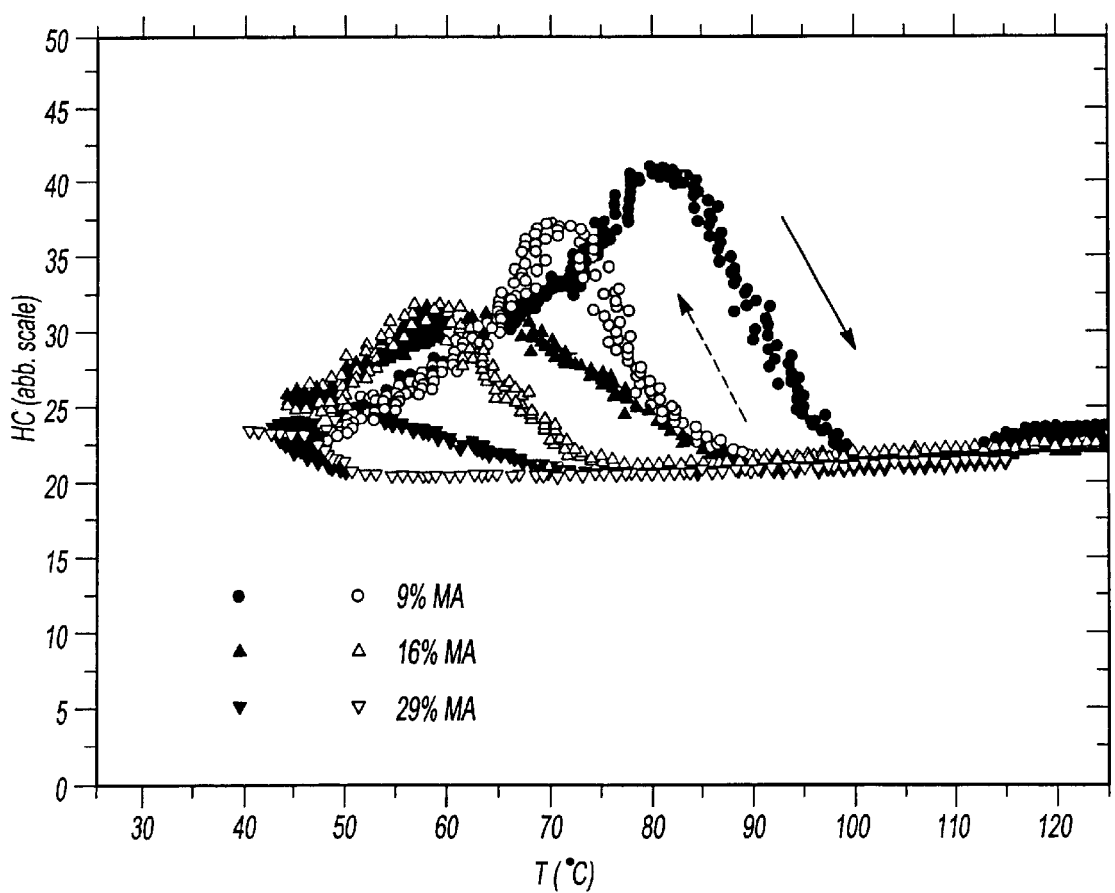

FIG. 11B shows heat capacity curves created with the apparatus of this invention for a series of ethylene-co-methyl acrylate random copolymers. The polyethylene-co-methyl acrylate copolymers were purchased from Aldrich, and the Aldrich catalog numbers, the percentages of methyl acylate incorporation, and melting points according to the manufacturer were: #43076-5, 9% MA, MP=93° C.; #43264-4, 16% MA, MP=85° C.; and #43075-7, 29% MA, MP=48° C.

The ethylene co-polymers were dissolved at a concentration of approximately 5 wt % in trichlorobenzene, a high boiling point solvent, at 150 degrees C. Approximately 5 to 10 ml were dispensed onto each sensor 12 and were kept in place by the naturally occurring wells beneath the silicon nitride membranes 94. The solvent was allowed to air dry, leaving a polymer film 90 deposited on each membrane 94. The heat capacity data was obtained using the $2\omega$ method, as described below. A broad peak in the heat capacity is observed, marking the melting point. This peak is due to the latent heat associated with melting of crystalline portions of the polymer and the data are comparable to the results that may be obtained by traditional DSC. The reduction of the value of the melting point and the degree of crystallinity with increasing methyl acrylate incorporation can be easily seen in FIG. 11B.

Heat capacity measurements can also be used to gain information on the architecture and microstructure of glassy (entirely non-crystalline) polymers. For example, a "random" copolymer of a given composition may be either random or "blocky",depending on whether or not the comonomers alternate in a random way or tend to occur in longer "runs" of a given monomer type. The degree of randomness or blockiness can affect the end properties of the material. The degree of blockiness can be assessed through heat capacity measurements: a random copolymer tends to have a single broad glass transition, at a temperature intermediate between the Tg's of the constituent monomers. If the random copolymer is actually blocky, however, two distinct Tg's may be observed, corresponding to domains which form almost entirely from long runs of one or the other monomer.

In a similar manner, heat capacity measurements can distinguish between immiscible and miscible polymer blends or between phase-separated or phase-mixed block copolymers. Phase-mixed systems show a single Tg, while phase separated systems show two distinct Tg's. Even in the case of a phase separated blend, small amounts of miscibility will occur, i.e., the two phases are not "pure".This can also be assessed using Tg measurements, as the two Tg's will be somewhat shifted from the values for the pure polymers.

The above examples illustrate the many ways in which thermal analysis data can be used to gain important information on the structure and physical properties of polymers. This information can be used to evaluate the success or failure of a particular synthetic route in making a polymer with a given chemical composition and physical structure/architecture; or to judge the suitability of a particular polymer for a given application. Within the context of a combinatorial materials science approach to developing new polymer synthetic strategies or new polymeric materials, in which many catalysts, process conditions, chain compositions and architectures, etc, will be attempted, it is highly desirable to be able to obtain thermal analysis information in a rapid fashion.

The sensor array method and apparatus of the present invention has a significant advantage over other thermal analysis methods and apparatuses because it can characterize many different materials simultaneously and quickly. Instead of obtaining only one heat capacity scan per unit time, the inventive method and structure can obtain tens or even hundreds of heat capacity plots in the same amount of time. Further, the sensor for this particular application obtains data that can be readily correlated with known data, e.g., from a conventional differential scanning calorimeter (DSC), in that the heat capacity of the sample can be directly measured and plotted. Thus, the sensor output needs only minimal processing to generate data that can be easily interpreted.

The method for utilizing the present invention is also simple, and further facilitates the rapid analysis of numerous samples. Once a library of, for example, 100 polymers is created via combinatorial methods, each polymer may be deposited on the microcalorimeter sensor array of the present invention to measure each polymer's thermal properties. To form a sample 90, a small amount of solution containing the polymer sample is placed on each sensor 12 and allowed to dry, leaving a film of the polymer behind. This can be done one sample at a time or multiple samples at a time manually or automatically, such as by using a liquid dispensing robot with a single or multiple syringe tip. In a preferred embodiment, the sensor array 10 has a standardized combinatorial chemistry format so that the polymers may be deposited simultaneously on multiple sensors 12 in the sensor array 10, using known combinatorial tools such as multiple syringe/multiple tip pipettes, containing 4, 8, 12, or even 96 pipette tips possibly with the standard 9 mm spacing.

Once the solvent has evaporated, leaving a polymer film sample 90 on each sensor 12, the sensor array 10 is simply connected to the electronic platform. This will be done, for example as shown in FIG. 4, by inserting the sensor array 10 in a positioning fixture 42 attached to the printed circuit board 30 and applying pressure to the sensor array substrate 16 by tightening screws 46 or other fasteners (such as clips or clamps) on a compression fixture 44, insuring good contact between the sensor array 10 and the printed circuit board 30. Preferably, the printed circuit board 30 is housed in a chamber that can be evacuated. This eliminates heat losses to the atmosphere, and noise in the temperature measurements due to convection. A heat capacity scan is then generated for each sensor 12 (typically in less than a minute), obtaining each material sample's crystallinity/amorphous properties, melting point, glass transition point, and other material characteristic information. The entire measurement procedure may be controlled and executed by a computer program in the electronic platform. Using the software, the user initially specifies which samples in the array 10 are to be analyzed and provides other measurement information, such as the temperature sweep rate and modulation frequency.

As a result, in this example, the heat capacity plots can be obtained for 100 samples in about 90 minutes or less, compared to around one or two samples in 90 minutes for known materials characterization devices, such as standard differential scanning calorimeters. By comparing and analyzing the heat capacity plots of each material in the library quickly, a user can select which polymers in the library have the most desirable physical properties for a selected application or determine whether or not a given synthetic strategy and set of starting ingredients has in fact produced a polymer of a desired architecture and associated physical properties.

Of course, thermal analysis is not limited to polymers. The same type of analysis can also be used to characterize inorganic solid state materials, such as glasses, metal alloys, and compounds.

Figure 11C:
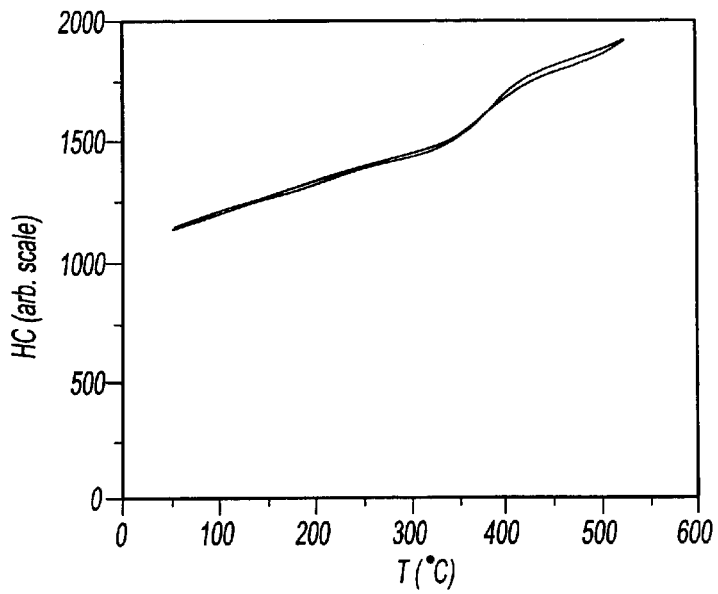

FIG. 11C shows an example using this invention of a glass transition (Tg) measurement in a low-Tg (400° C.) silica glass manufactured by Ferro corporation, type 7578 crystallizing solder glass. Such "solder glasses" are widely used as sealing or fusing materials in a variety of specialized electronics and other applications, and the ability to rapidly measure Tg of different combinatorially synthesized silica glass formulations would be highly desirable in the development of new specialty glasses. The glass used in this example has a glass transition temperature at approximately 395° C. according to the manufacturer. The glass is normally obtained in powder form, and the powder was formed into a disk for this experiment by placing the powder in a mold and sintering at 450 degrees C. for four hours. A 1 μm thick film was then deposited onto the sensor array using laser ablation. The measurements were made using the 3ω method, described below.

The present invention is also useful in the context of a search for new bulk amorphous metallic alloys, metals which do not have a regular crystal structure, and which display a reversible glass transition much in the same manner as silica glasses. Such materials are highly desirable for their unique high strength and resiliency in comparison to conventional alloys. Amorphous alloys typically consist of three or more different metal atoms, and achieving desirable physical properties such as strong glass forming ability and a low Tg requires synthesizing many different alloys with slight variations in composition. Thermal analysis is a widely used technique for analyzing the glass transition and other phase transitions in candidate amorphous alloy materials. Thus, the combination of combinatorial synthesis and rapid thermal analysis is a powerful technique which can be used in the search for new amorphous alloys.

Figure 11D:
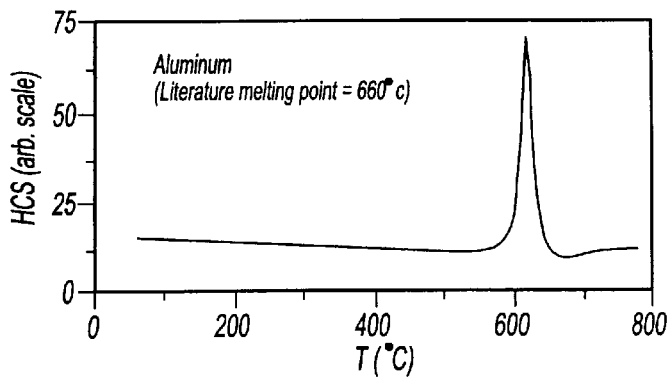
Figure 11E:
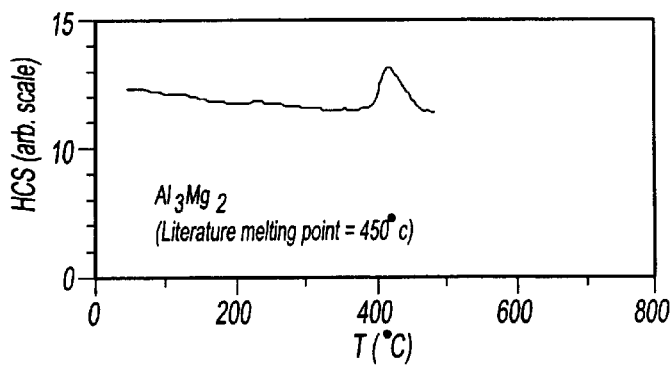
Figure 11F:
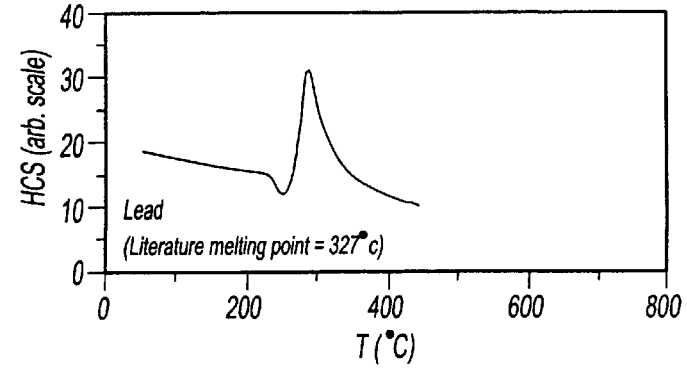

FIGS. 11D and 11F show examples of the determination of melting points of several pure metals, and FIG. 11E shows a thermal analysis scan for a compound using the apparatus and method of this invention. The aluminum and lead films, each about 0.5 μm thick, shown in FIGS. 11D and 11F, respectively, were deposited on the sensors by RF sputtering, using single element sputtering targets. The $Al_3Mg_2$ film was deposited as a multilayer film, using a combinatorial sputtering chamber. The film as deposited contained alternating layers of 24 Å of AL and 26 Å of Mg. This layering was repeated 65 times, for a total film thickness of 3250 Å. The layers mix to form the desired compound during the initial heating stage, which is below the melting point. The results shown in FIGS. 11D through 11F were obtained using the 3ω method, as described in this application. Thus, the present invention, when combined with combinatorial synthesis of thin solid films, can be used to map out the outlines of entire binary, ternary, and higher order phase diagrams. This can be extremely useful in the search for new solid state compounds, alloys, and other materials.

The method, which will be described in greater detail below, and the apparatus of the present invention, which has been described, can thus analyze libraries of metal alloys, glasses, and other solid state compounds and materials having varying compositions, to detect the occurrence of important phase transitions. Again, because of the sensor array 10 and library format used in the invention, a large number of materials can be generated and screened in a short period of time. In the preferred method of deposition, the library of thin film materials is directly produced on the sensor array substrate 16, using combinatorial masking and deposition techniques. See, e.g., WO 98/47613, incorporated herein by reference. Solid state films can also be produced from liquid precursors by sol-gel processes.

In short, material samples 90 are placed in intimate thermal contact with the membrane 94 using vapor deposition techniques or by dissolving the sample in a solvent, depositing the solution on a sensor 12 and allowing the solvent to dry to form a thin sample material film on the membrane 94 of the sensor 12. The thinness of the membrane 94 and the sample 90 allows the sample 90 to be heated through very quickly, making rapid scanning of the sample over a wide temperature range possible while still obtaining clear thermal characteristic plots showing phase transitions. This specific embodiment of the invention can scan over several hundred degrees and obtain heat capacity data for a given sample in 10 to 30 seconds, compared with 30 minutes to 2 hours for conventional calorimeters. This processing speed is further enhanced by the invention's array format, allowing parallel or rapid serial scanning of multiple samples which are deposited on a single substrate, and increasing the number of samples tested per unit time to as high as 64 or more samples in 15 minutes.

EXPERIMENTAL EXAMPLE

Thermal Analysis with Temperature Modulation

FIGS. 12A through 12H and FIGS. 13A through 13F illustrate thermal analysis using temperature modulation. The preferred sensor structure for conducting this type of analysis is the structure described above and shown in FIGS. 9A through 9C, but other thermal sensor structures can be used without departing from the spirit of the invention. The following discussion of non-modulated calorimetry will provide an explanation of the theory behind heat capacity measurements and will illustrate why temperature modulated calorimetry is the preferred method for making heat capacity measurements with the sensors 12.

In an ideal or simplistic heat capacity measurement, all heat input into a sample is retained by the sample, resulting in increases in the temperature or change of the physical state of the sample. The heat capacity can then be determined as the ratio between the rate of heat input and the rate of temperature increase, $C_p = \Delta Q/\Delta T$. In reality, some of the heat input to the sample is continuously lost to the environment through conduction, convection, radiation, etc. In order for the results of a heat capacity measurement to be meaningful, either some procedure must be implemented to measure or account for the heat energy lost to the environment, as is done in differential scanning calorimetry by means of an "empty cell" reference sample, or the rate at which heat is input to the sample must be much greater than the maximum rate at which heat is lost, so that losses may be neglected while maintaining a good approximation of the sample's heat capacity.

In the latter case, the entire measurement must be completed in a time shorter than the thermal relaxation time t1 of the sample, where t1 is the time that it takes for the sample to come to equilibrium at a new temperature when the heat input level is changed to a new value. If the heat input is set to zero, t1 is the time constant for the sample to return to the temperature of the environment. The relaxation time is given by $t1 = C_p/k$, where $C_p$ is the heat capacity and k is the thermal loss constant to the environment. The reason for conducting a rapid (less than t1) measurement is easy to understand: if the power is suddenly turned up to a certain level, the temperature will initially increase rapidly and the losses to the environment will be negligible, since the sample is initially at nearly the same temperature as the environment. However, after a time of approximately a few times t2, the sample's temperature saturates or plateaus to a limiting value, as the heat input and losses to the environment become exactly equal. Thus, heat losses to the environment can be neglected only if the temperature increase is conducted over a time much shorter than t1.

For small, microthin samples, such as those tested in the invention, the time constant t1 can be quite short, typically 0.1 seconds, due to the sample's very low heat capacity. The high temperature ramp rates which must be used with such samples in a "continuous sweep" calorimetry experiment, e.g. 100's to 10,000's of degrees per second, make analysis of many phase transitions difficult or impossible, particularly in more complex materials. If a much slower ramp rate is used, then an equilibrium prevails between the heat input and the losses to the environment, and generally no information can be gained about the heat capacity. Increasingly complex materials may take increasingly long times to complete structural rearrangements that occur at a phase transition, which involve collective motions and rearrangements of many atoms or molecules. Therefore, it is desirable to use a measurement method in which the heat capacity can be measured while the average temperature is varying at an arbitrary rate.

AC calorimetry, when combined with the sensor design of the invention, is a preferred way to obtain a rapid determination of heat capacity versus temperature with a minimum of off-line data analysis, but without requiring prohibitively fast scanning of the average temperature. Although this discussion focuses on modulated calorimetry, other calorimetric methods may be used in conjunction with the sensors or system of this invention, including methods based on measurements of the thermal relaxation time or methods in which the entire measurement is performed in a time that is shorter than the thermal relaxation time, which are well known in the art.

Figure 12A:
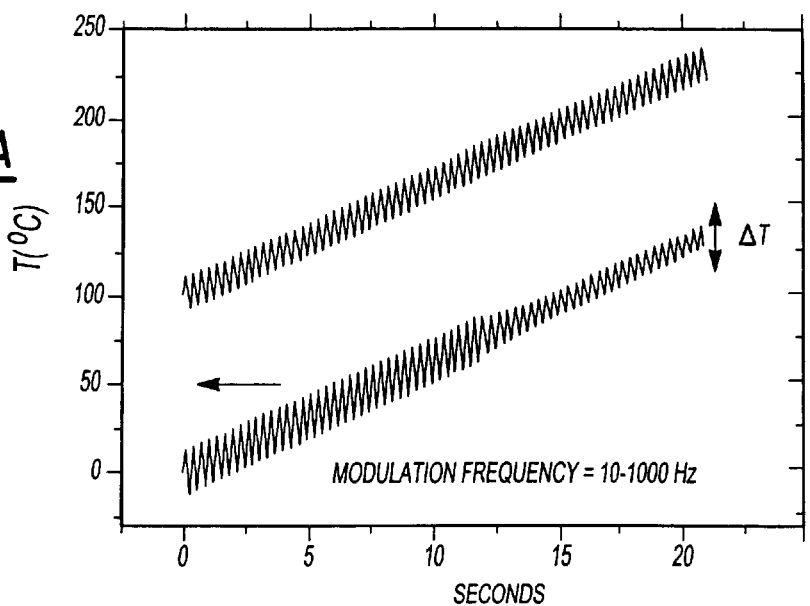
FIGS. 12A through 12I illustrate one system for conducting thermal analysis according to the present invention.
Figure 12B:
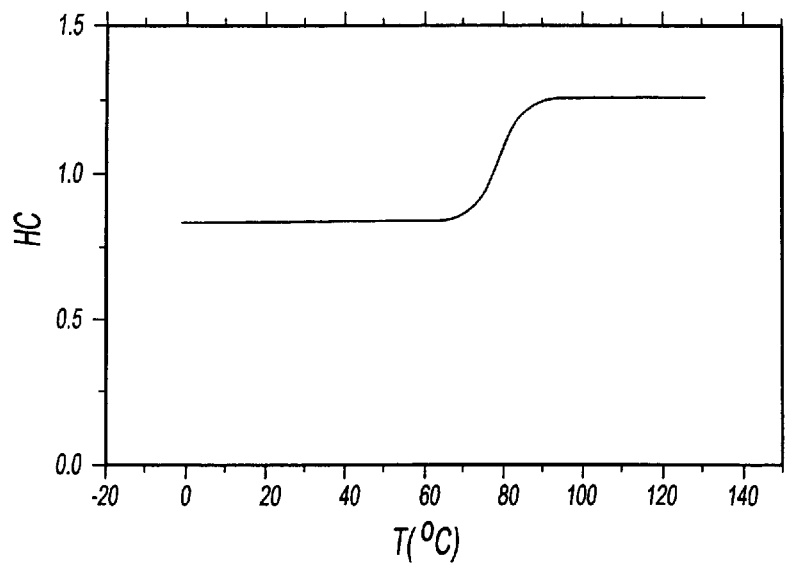

The general concepts of AC calorimetry will now be explained in conjunction with FIGS. 12A and 12B, which are general to the concepts. In AC calorimetry, the power input to the sample consists of a slowly varying average value P(t), and a modulated part ΔP. The heater power modulation frequency 2ω (corresponding to modulation of the heater voltage $V_H(t)$ at a frequency ω, since $P=V^2/R$) is chosen such that the period $\Delta t=\pi/\omega$ is much shorter than the time constant t1 for equilibration of the sample with the external environment, but much longer than the time constant t2 for internal equilibration between the sample, heater, and thermometer.

If the frequency ω is too low ($\omega<<\pi/t1$), then the total power input is always equal to the losses to the environment; in this case, the temperature modulation is in phase with the power input modulation, contains information only about the thermal losses to the environment, and contains no information about the heat capacity. If the frequency is chosen so that $\omega>>\pi/t1$, however, the sample temperature modulation lags behind the power input modulation by a phase angle of 90°, because there is insufficient time during a cycle for the sample to reach the temperatures corresponding to the maximum and minimum power inputs. The larger the heat capacity of the sample, the more slowly it responds to the power modulation, and the smaller the resulting temperature modulation will be. Under these conditions, the temperature modulation amplitude ΔT is given by $\Delta T=\Delta P/2\omega C_p$, where ΔP is the amplitude of the power modulation and $C_p$ is the heat capacity. Thus, the heat capacity is inversely proportional to the temperature modulation amplitude, for a fixed ΔP. If the frequency is too high, however, i.e. $\omega>>\pi/t2$, then the heater, thermometer, and sample are not in equilibrium with each other, and the thermometer thus does not give accurate information about the response of the sample temperature to the heater power input.

Thus, AC calorimetry generally involves measuring both the average temperature and the temperature modulation amplitude for a given sample, with an appropriately chosen frequency $2\pi/t1<<\omega<<2\pi/t2$, as the average temperature is varied. The heat capacity is given by $C_p=\Delta P/2\omega\Delta T$.

Figure 12C:
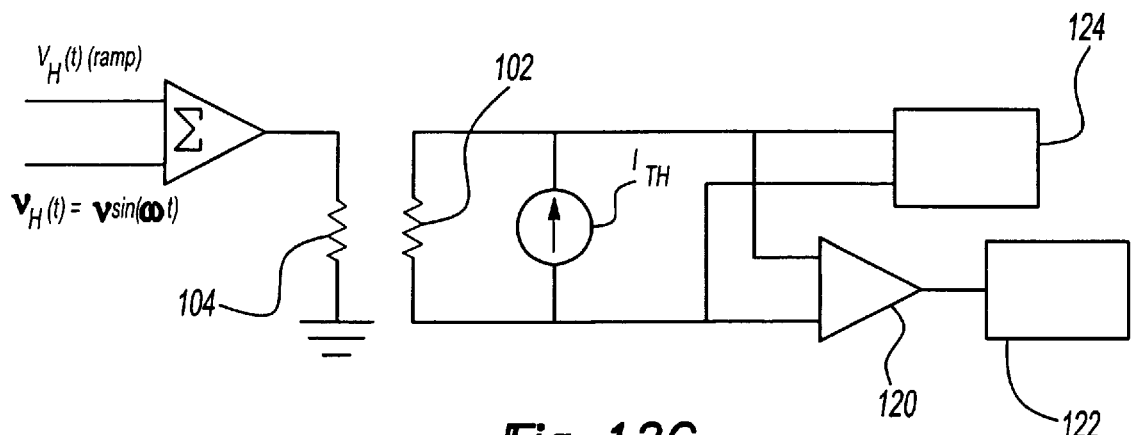
Figure 12D:
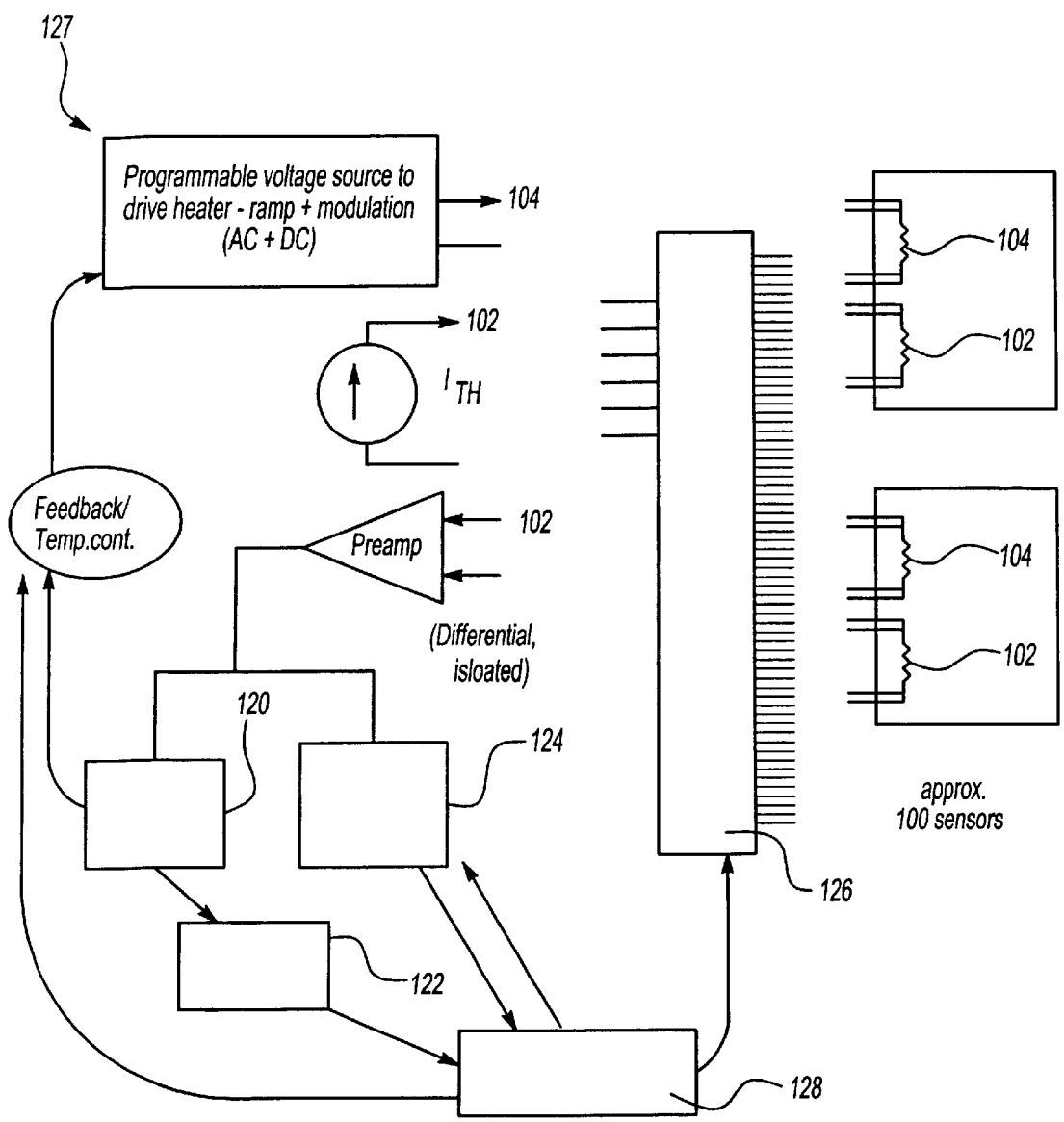
Figure 12E:
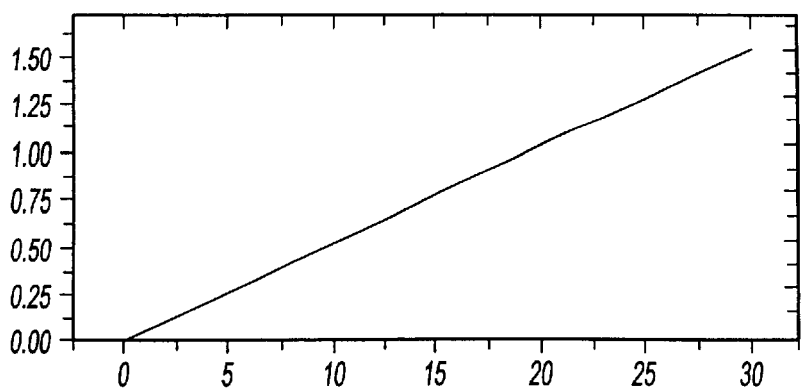
Figure 12F:
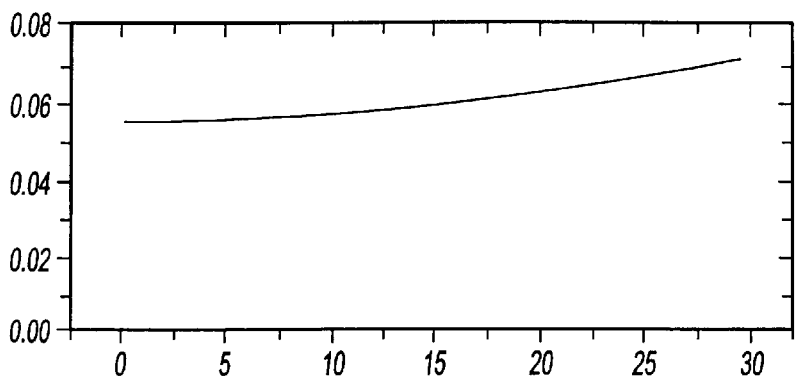
Figure 12G:
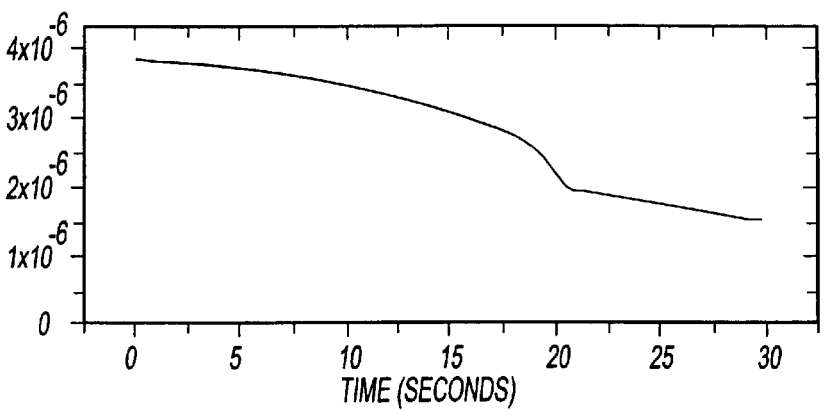
Figure 12H:
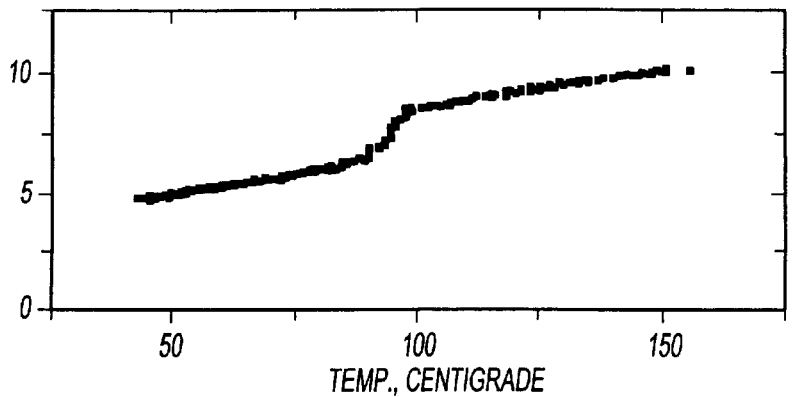
Figure 12:
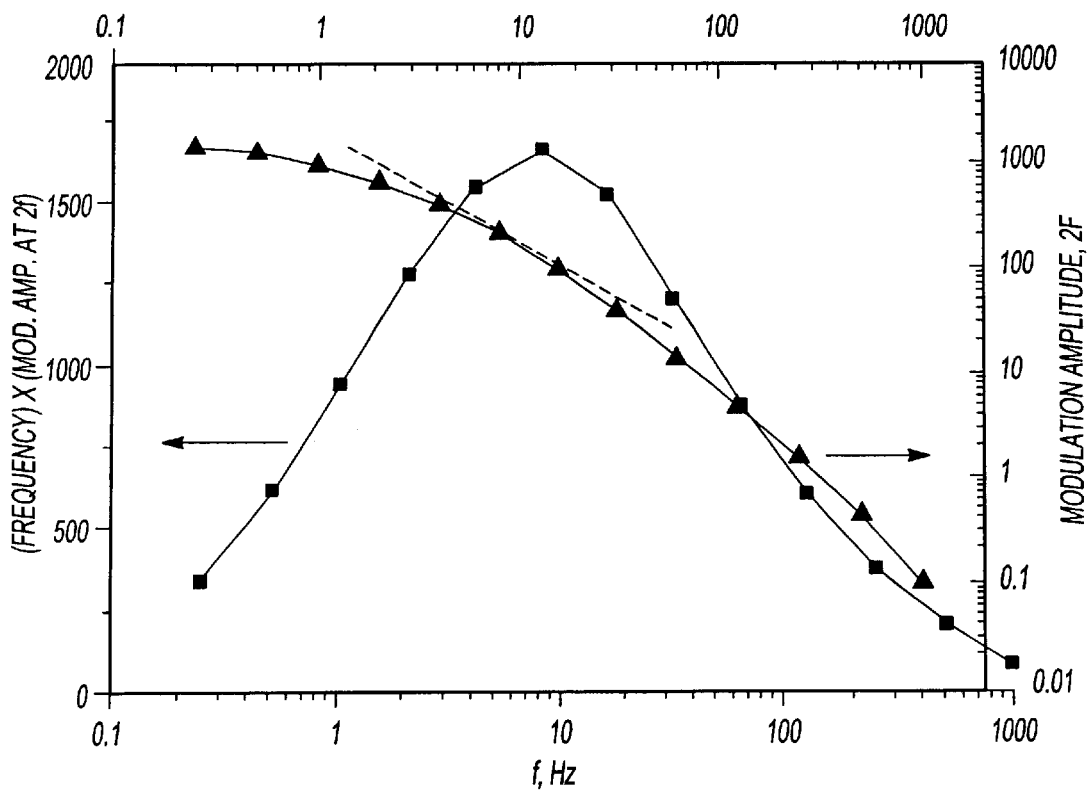

FIGS. 12C through 12H are explanatory diagrams of a particular embodiment of a heat capacity measurement system and measurement method, which uses the preferred sensor design discussed above and the AC calorimetry technique. This particular embodiment is referred to throughout this specification as the "2ω method". FIGS. 12C and 12D are representative diagrams explaining the 2ω method, while FIGS. 12E through 12H show examples of input and output signals according to this method.

The voltage signal to the heater, $V_H(t)$, is the sum of a slowly varying average value $V_{H,0}(t)$ and a modulation $v_H(t)=v_H e^{i\omega t}$ at frequency ω, i.e., $V_H(t)=V_{H,0}(t)+v_H e^{i\omega t}$. The input power is $V_H^2(t)/R_H=[V_{H,0}^2(t)+2V_{H,0}(t)v_H e^{i\omega t}+v_H^2 e^{2i\omega t}]/R_H$, and contains modulations at frequencies of both ω and 2ω. The temperature of the sample is monitored by measuring the resistance of the thermometer 102, $R_{TH}(t)$. In the 2ω method, this is done by passing a small DC current $I_{TH}$ through the thermometer 102 and measuring the voltage $V_{TH}(t)$. For many metals, the resistance varies linearly with temperature, and can be parameterized by the formula $R(T)=R(T=T_0)[1+\alpha(T-T_0)]$, where α is a constant characteristic of the metal, and $T_0$ is an arbitrary reference temperature. Thus, the temperature can be calculated directly from the thermometer voltage, using the formula $T=T_0+[(V_{TH}/V_{TH}(T_0))-1]/\alpha$, if α, $T_0$ and $V_{TH}(T_0)$ are known.

The average temperature and the temperature modulation at frequencies ω or 2ω can easily be determined over the course of an experiment by a number of means. The average temperature is most easily obtained by passing the thermometer voltage signal through a low pass filter 120 with a suitable cutoff frequency, which removes the modulation, measuring the filtered thermometer voltage with an analog-to-digital converter 122, and calculating the temperature using the formula given above. The modulation is most easily and accurately measured using a lockin amplifier 124, with the reference frequency set at ω or 2ω depending on which frequency is being monitored. Other techniques can also be used, such as an AC voltmeter with a narrow band pass filter on the input, a spectrum analyzer, or direct recording of the waveform and subsequent off-line analysis by fast Fourier transform.

It is preferred to monitor and analyze the signal at frequency 2ω. The principal reason is that the power modulation $\Delta P(2\omega)$, given by $v_H^2/R_H$, varies relatively little during the experiment, varying only due to changes in the heater resistance $R_H$ as the temperature is varied. In contrast, the power modulation $\Delta P(\omega))=2V_H(t)v_H/R_H$ is zero when the average heater voltage is zero, and varies over a much wider range during the course of an experiment due to the linear dependence on $V_H(t)$. This leads to vanishing sensitivity near the base temperature, and a large variation in the signal-to-noise ratio over the course of an experiment.

The heat capacity is given by $C_p=\Delta P/2\omega\Delta T$, as described earlier. Because $R_H$ increases with temperature, the input power modulation $\Delta P=v_H^2/R_H$ decreases with increasing temperature. This leads to a decrease in the temperature modulation amplitude, independent of any changes in the heat capacity. This must be accounted for in analyzing the data. Because ΔP is inversely proportional to $R_H$, the heat capacity is proportional to $1/R_H\Delta T$, since $v_H$ and ω are constant during a given experiment. Although $R_H$ can in principle be precisely determined by an additional measurement, e.g., by monitoring the DC current drawn by the heater in response to the DC voltage $V_H$ and an absolute value of Cp determined, it is a reasonable approximation for many purposes to assume that the heater and thermometer are at the same temperature, and substitute $R_{TH}$ (which is already being measured) for $R_H$.

Thus, if one is only interested in identifying prominent features in the heat capacity curve that are associated with phase transitions or other significant thermal events, as is often the case, and is not interested in the precise absolute value of the heat capacity, then the heat capacity can be approximated (up to a multiplicative constant or scaling factor) by $1/[<V_{TH}>\Delta V_{TH}(2\omega)]$, where the denominator is the product of the DC and modulated values of the thermometer voltage. A plot of this quantity vs. the temperature (which is derived from $V_{TH}$) captures all of the essential information in the heat capacity curve. More precise analysis methods may be used to obtain an absolute value of the heat capacity, without departing from the scope and spirit of the invention.

It is now possible to explain more clearly why AC calorimetry, as embodied by the $2\omega$ method, combined with the preferred sensor design, allows for such rapid measurements of heat capacity curves and determinations of phase transition points. A measurement of the heat capacity at a given temperature requires measuring the modulation amplitude at that temperature. An accurate measurement of the modulation amplitude typically requires averaging or Fourier transforming over at least several cycles. Five cycles, for example, is a reasonable minimum number. Thus, at a given temperature, an accurate determination of the heat capacity can be made in approximately 0.1 seconds for a typical temperature modulation frequency of $2\omega=50$ Hz. If it is desired to obtain one measurement per degree as the temperature is varied, for example, then the average temperature may be varied at a rate of approximately 10° C. per second, or 600° C. per minute, compared to typical sweep rates of 10° C. per minute for conventional DSC instruments.

In practice, the temperature is not stabilized at a set of discrete values while. measurements are made at these values; rather, the temperature increases continuously, and the modulation data can be considered a "running average" of the modulation amplitude over a finite temperature range. This temperature range is typically several degrees, and is determined by the temperature sweep rate and the averaging time for the modulation amplitude measurement.

Referring to FIG. 12C, using the $2\omega$ method in the sensor array structure according to the present invention does not require any modification of the sensor structure itself because of the modular sensor array structure, standardized interconnection method, and flexible electronic platform. As explained above, each sensor 12 in the sensor array 10 is connected to a multiplexer 126 or other signal routing means, and both the multiplexer 126 and the electronic test circuitry 127 for driving the sensors are controlled by a computer 128. The electronic test circuitry 127 and the computer 128 together can be considered a flexible electronic platform. To characterize materials on the sensors 12 one at a time, the computer 128 controls the multiplexers 126 so that it connects a given sensor 12 the electronic test circuitry. The electrical signals for a complete scan (as selected by the user) are sent to and read from the heater 104 and thermometer 102 on the selected sensor 12, and then the multiplexer 126 switches the connection to link the electronics platform with the next sensor in the sequence. Thus, the invention allows for ultimate flexibility in sensor array testing. Sample results from a test conducted according to the $2\omega$ method are shown in FIGS. 12E through 12H for illustrative purposes only. More specific details on the preferred manner in which the tests are conducted are as follows: The heater ramp voltage is obtained from an auxiliary analog output of an Stanford Research Systems SRS 830 lockin amplifier. This voltage is set via instructions to the lockin amplifier from the computer, transmitted over a GPIB interface. For the specific heater 104 design in the preferred sensor embodiment, a voltage ramp from 0 to 1.5 volts is sufficient to raise the temperature of the sensor to approximately 150° C. (in vacuum). Higher maximum voltages result in higher maximum temperatures. The ramp voltage is incremented by a small amount (approximately ten times per second) and the size of the increment can be specified by the user before beginning a scanning operation. The size of the increment is typically in the range of from about 0.005 to 0.01 volts, so the total scan time is approximately 15 to 30 second. When the maximum voltage is reached, the ramp voltage is either ramped back down to zero at the same rate while taking data; or the ramp voltage is set to zero and the scan is completed.

The heater modulation voltage is generated by the same lockin amplifier's sine wave oscillator output. Fundamental frequencies of 10–40 Hz were generally used with the $2\omega$ method, and a typical modulation amplitude is several tenths of a volt. The ramp and modulation signals are added by a summing amplifier from OpAmp Labs, which also buffers the signals and supplies adequate current to drive the heater, which has a 2-wire impedance of approximately 100Ω.

The DC current for the thermometer 102 was generated by connecting a 9V battery in series with a 10 kΩ resistor and the thermometer 102, producing a current of approximately 1 mA. The use of a battery-powered current source insures that the thermometer 102 circuit is isolated from ground and from the circuitry connected to the heater 104. The thermometer 102 resistance is measured in a 4-wire configuration, and the 4-wire resistance at room temperature is typically 50Ω. Thus, the initial thermometer voltage is approximately 50 mV.

The thermometer voltage is then analyzed to extract the average value, which gives information on the temperature, and the modulation amplitude, which gives information on the temperature oscillation amplitude and the heat capacity. To measure the average thermometer voltage, the thermometer voltage is connected to the differential inputs of an SRS 560 low-noise voltage preamplifier with variable gain and a programmable filter. The preamplifier is typically used with a voltage gain of approximately 10, and a low pass filter set at 1–3 Hz to remove the modulation. The preamplifier output is connected to an auxiliary analog-to-digital converter input of the lockin amplifier, and the voltage is read via instructions from the computer.

To measure the modulation voltage, the thermometer voltage is sent to the differential inputs of the SRS 830 lockin amplifier, which is set for signal detection at the second harmonic frequency of the sin wave being output from the oscillator. The second harmonic frequency is thus typically in the range 2f=20–80 Hz. The lockin input bandpass filter is set at 24 dB/octave, and a 0.3 second output time constant is typically used. Although phase-sensitive detection can easily be done, only the total magnitude of the modulation signal was recorded for simplicity. This is permissible if the frequency is properly chosen so that $t1>>\pi/\omega>>t2$, where t1 and t2 are the external and internal thermal relaxation times discussed above.

The correct measuring frequency is chosen by measuring the modulation voltage $V_{th}(2\omega)$ as a function of the drive frequency, and looking for a broad peak in a plot of $\omega^*V_{th}(2\omega)$ versus $f=\omega/2\pi$, as is well known to those skilled in the art of AC calorimetry. An example is shown in FIG. 12I, using the preferred sensors discussed above. At low frequencies $\omega<<\pi/t1$, the temperature modulation amplitude $\Delta T$ and $V_{th}(2\omega)$ are independent of frequency, since a balance always prevails between the modulated heat input and the losses to the environment. In this region, $\omega^*V_{th}(2\omega)$ increases linearly with Ω. In the optimal frequency range for conducting calorimetry measurements, ΔT is proportional to 1/ω, as explained previously, so $\omega^* V_{th}(2\omega)$ is approximately constant. At high frequencies $\omega >> \pi/t2$, the thermometer temperature is out of equilibrium with the heater temperature, since there is insufficient time for heat to diffuse across the width of the thermometer during a single cycle. The temperature distribution over the thermometer takes the form of a damped travelling wave, with a wavelength shorter than the size of the thermometer, and the average temperature and voltage modulation decrease as the frequency is increased above $\pi/t2$. Thus a plot of $\omega^* V_{th}(2\omega)$ has the form of a peak, with the broad maximum indicating the optimum frequency range for performing calorimetry measurements. Because of the breadth of the peak in this plot, it is not necessary to perform a frequency analysis for each sample. Once it has been done for a given type of sample (e.g. a class of materials with roughly similar film thickness and thermal conductivity), the same frequency can be used for all subsequent measurements on samples of that general type. In the example, 15 Hz is preferred, but anywhere in the range of from about 5 to about 30 Hz may be used.

Once the modulation frequency and amplitude have been set and all of the signals are properly routed, numerous measurements can be rapidly made using a simple procedure. In the preferred embodiment of the procedure, a group of sensors is first specified for measurement via manual input to the computer by the user. Once this has been done, the user instructs the computer to begin an automated measuring procedure. All operations described below are performed automatically by the computer, following parameters set by the user before the automated procedure is begun, such as setting the ramp rate, etc.

The computer closes selected switches in the multiplexer so that the first sensor in the specified set is connected to the electronics instruments (current source, lockin, oscillator, etc.). It is desirable to wait several seconds for the electronics to settle after closing the connections between a sensor and the electronic platform, to eliminate transient responses.

The heater ramp voltage is initially zero. Before beginning to increase the ramp voltage, the computer records the average thermometer voltage, which is defined as $V(T_0)$. $T_0$ is the temperature of the sensor at the beginning of the scan. This will be somewhat higher than room temperature due to the power dissipated in the heater by the modulation voltage. In a preferred procedure, the modulation voltage is also set to zero before $V(T_0)$ is recorded. It can then be assumed that $T_0$ is equal to the room temperature, provided that the heat dissipated in the thermometer 102 by the DC current causes only minimal self-heating. Various other procedures may be performed to determine more precisely the sensor temperature at the beginning of the scan.

The modulation voltage is then turned on again, and the following procedure is iterated or looped approximately ten times per second: (1) measure the average thermometer voltage $<V_{th}>$ and the modulation voltage $V_{th}(2\omega)$; (2) calculate the temperature T using the formula $T = [<V_{th}>/V_{th}(T_0) - 1]/\alpha + T_0$, where the coefficient α is characteristic of the metal which the thermometer is made out of and can be determined separately by a variety of well known means. For Pt, typically α=0.0025–0.003; (3) calculate a quantity proportional to the heat capacity, referred to as the "heat capacity signal" $C_p$, using the formula $C_p = [<V_{th}>^* V_{th}(2\omega)]^{-1}$, as discussed above; (4) store the values of the time, the heater drive voltage $V_H$, and the measured and derived quantities $<V_{th}>$, $V_{th}(2\omega)$, T, and $C_p$ in computer memory; (5) increment $V_H$ to a new value; and (6) repeat steps (1) through (5). When the scan is finished, $V_H$ is set to zero and the data stored in memory are transferred to a file on a storage device. The next sensor is then selected by the computer and multiplexer, and the entire scan procedure is repeated.

Figure 13A:
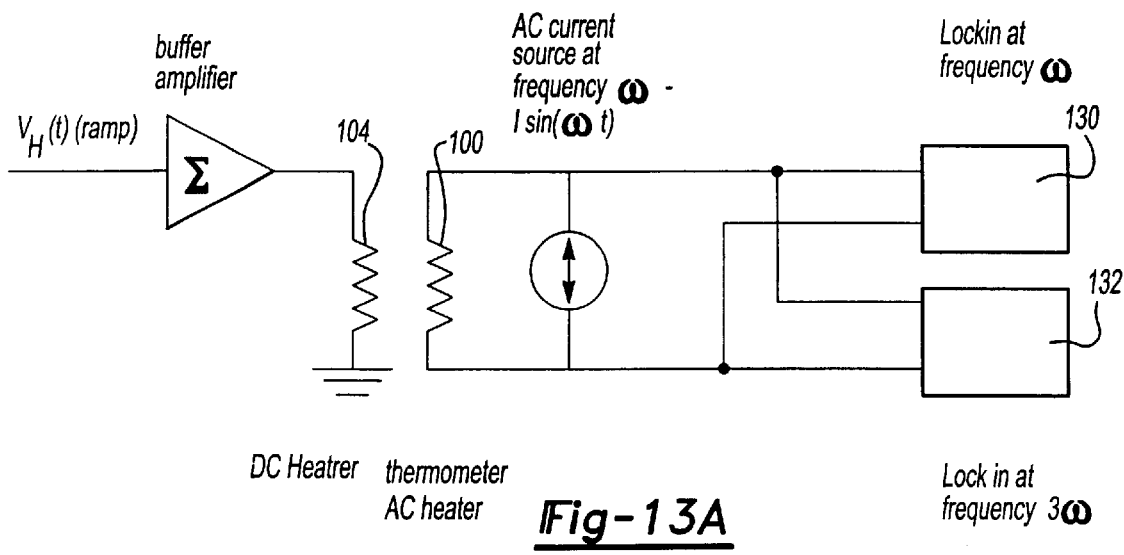
FIGS. 13A through 13G illustrate another system for conducting thermal analysis according to the present invention.
Figure 13B:
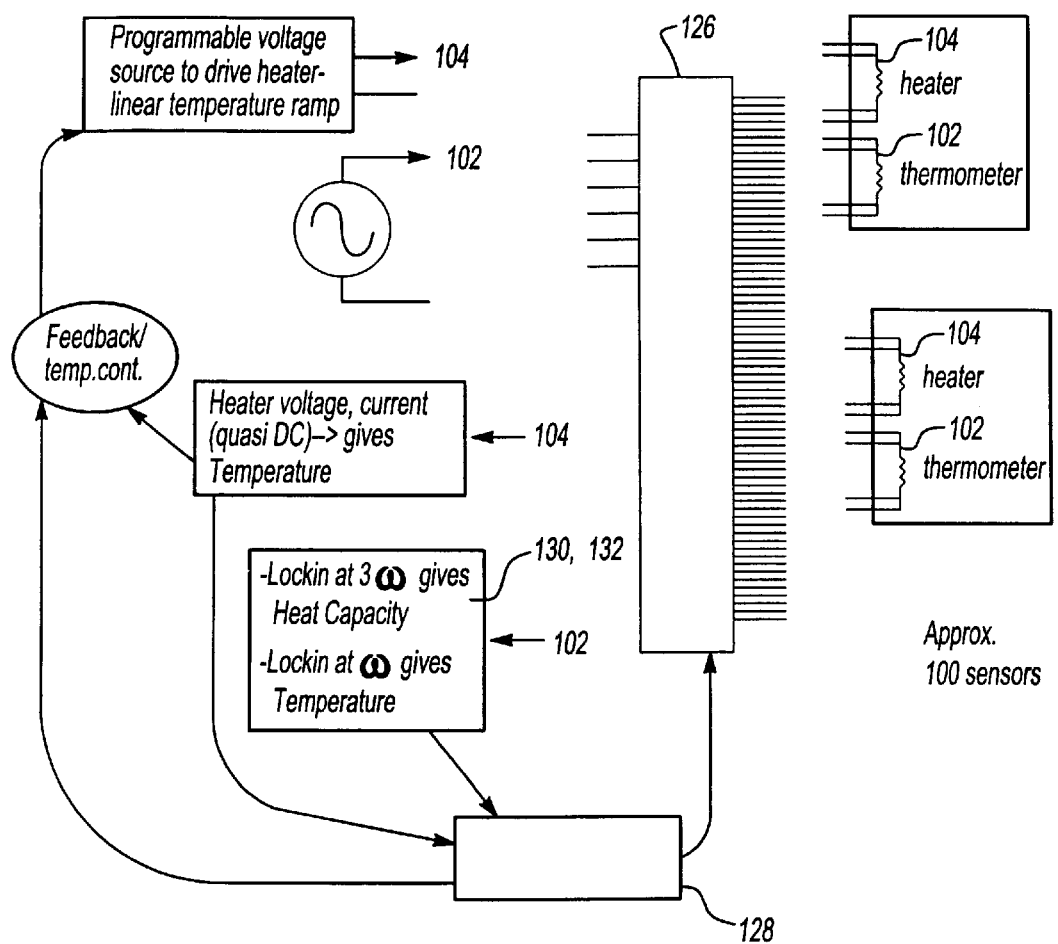
Figure 13C:
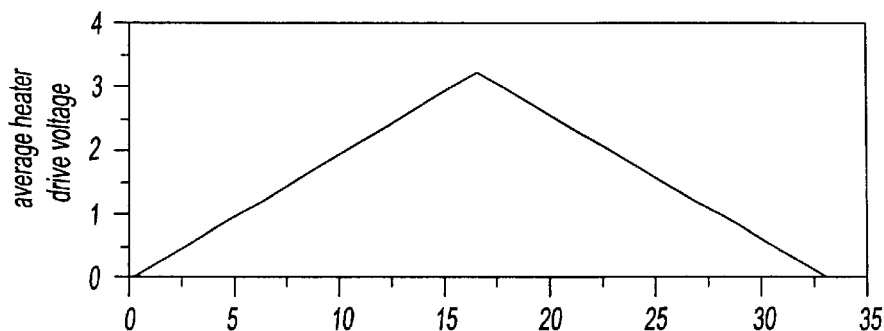
Figure 13D:
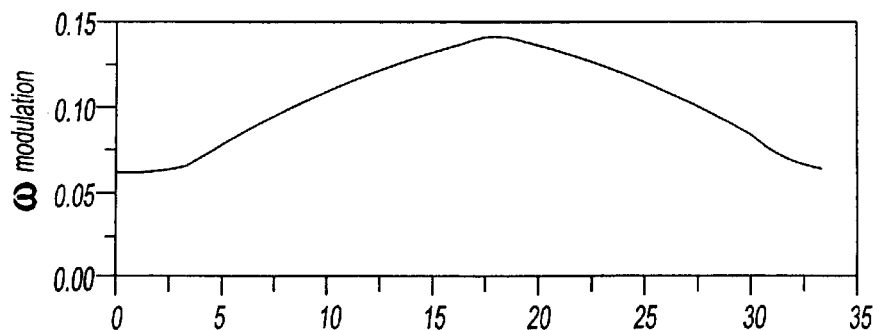
Figure 13E:
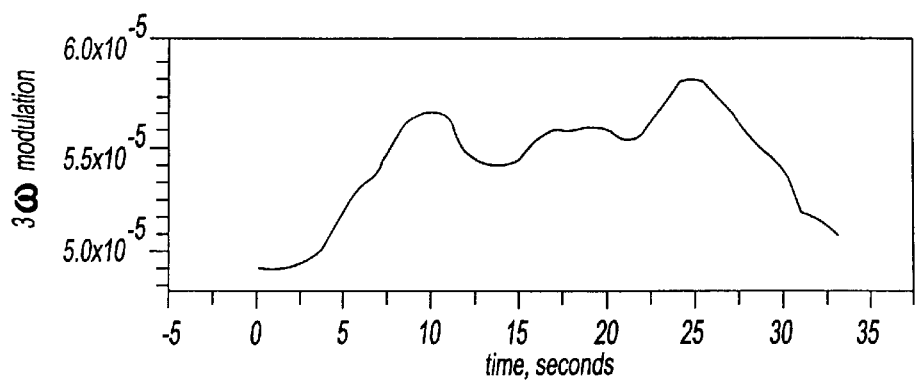
Figure 13F:
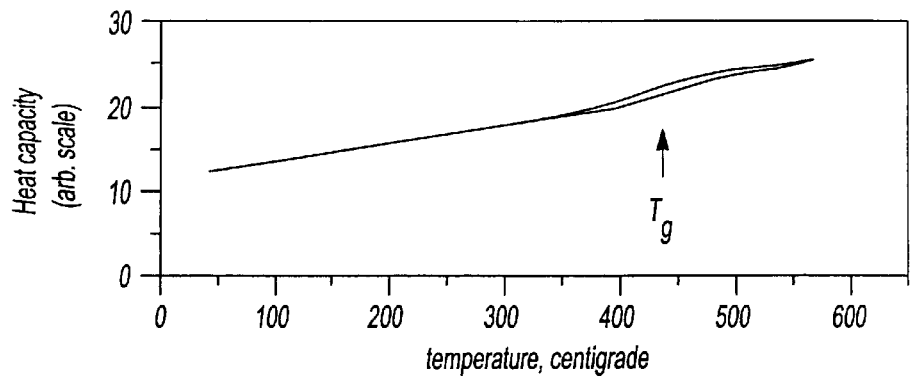

An alternative AC calorimetry method that can be used in the invention is the "3ω" method. FIGS. 13A and 13B are representative diagrams explaining the preferred materials characterization apparatus configuration using the 3ω method, while FIGS. 13C through 13F show examples of input and output signals according to this method. In this method, the heater receives only a ramped DC voltage $V_{H,0}(t)$, instead of a ramped voltage with a modulated AC voltage superimposed thereon. Also in the "3ω" method, an AC current in the form of a pure sine wave at frequency ω is sent through the thermometer instead of a DC current. The AC current through the thermometer preferably has a constant amplitude. Further, rather than measuring the 2ω modulation amplitude and the average value of the thermometer voltage to determine the sample material's heat capacity and temperature, respectively, the 3ω method measures the third harmonic in the thermometer voltage to determine the sample's heat capacity, as shown in FIG. 13E, and measures the first harmonic voltage to determine the temperature, as shown in FIG. 13D and as explained below.

If the AC current amplitude is sufficiently small, or the sample's heat capacity is sufficiently large, then the temperature of the sample does not vary in response to the AC current. The thermometer resistance is constant, and the thermometer voltage is a pure sine wave, since $V_{TH} = IR_{TH}$ and I is a pure sine wave. In this case there are no higher harmonic signals. If the AC current is sufficiently large, however, the input power modulation at frequency 2ω will cause a temperature modulation, and therefore a resistance modulation, at frequency 2ω, i.e., $R_{TH}(t) = <R_{TH}> + \Delta R e^{2i\omega t}$, where ΔR is proportional to ΔT. Since $V_{TH} = IR_{TH}$ and I is a pure sine wave, $V_{TH} = I_0 e^{i\omega t}(R_{TH}(t) = I_0 <R_{TH}> e^{i\omega t} + I_0 \Delta R e^{3i\omega t}$. The first harmonic voltage is thus proportional to the thermometer resistance, and therefore to the temperature, while the third harmonic voltage is proportional to the temperature modulation, and therefore gives information about the heat capacity, as in the 2ω method. Typically, the ω component of $V_{TH}$ is between 100 and 1000 times larger than the 3ω component, depending on the sample's particular thermal characteristics, the AC signal amplitude, and the geometry of the heater/thermometer 100. To analyze the voltage output from the heater/thermometer 100, a component in the electronic platform that receives the voltage output can lock in at frequency ω to detect the basic sine waveform and at frequency 3ω to detect the third harmonic. As explained in FIGS. 13A and 13B, two separate lockin amplifiers 130, 132 or a single lockin amplifier that can switch between the two frequencies can be used. The advantage of using two separate lockin amplifiers tuned, respectively, to the ω and 3ω frequencies 130, 132 is that both the temperature and the heat capacity measurements can be conducted simultaneously in real time, greatly increasing measurement speed and eliminating the waiting period needed for a single lockin amplifier to settle after switching its frequency. A representative block diagram illustrating the components of a preferred sensor array and electronic platform for the 3ω method is shown in FIG. 13B.

The 3ω method in its preferred embodiment requires additional signal processing equipment or methods in order to extract separately the modulation amplitudes at two separate frequencies. However, the 3ω method has a number of advantages over the 2ω method as well. In the 2ω method, the power modulation is produced by the heater 104, while the temperature modulation is sensed at the thermometer 102. The time constant t2 is the thus time required for heat to diffuse laterally across the membrane 94 from the heater 104 to the thermometer 102. While this time can be made fairly small, this still limits the frequency range to typically 5–50 Hz, and therefore places some limits on the measurement speed.

In the 3ω method, the temperature modulation is both produced and measured by the thermometer; in this case, t2 is the time required for heat to diffuse vertically across the thickness of the membrane 94 and into the thin film sample 90 rather than horizontally from the heater 104 to the thermometer 102. Because the sample 90 and the sensor 12 taken together are typically only a few microns thick, this time is much shorter than the t2 associated with the 2ω method. This in turn permits the use of measuring frequencies in the kHz range, with a corresponding increase in the possible temperature ramp rate and measurement speed. In addition, because the modulated power does not have to diffuse any distance laterally across the membrane, there are no radiative losses as the power travels from the modulation source to the modulation sensor since they are one and the same.

Sample test results obtained using the 3ω method are shown in FIGS. 13C through 13F. The samples are a film of low Tg solder glass, form Ferro, as detailed above. The configuration of the electronics platform for the 3ω method is somewhat different than for the 2ω method, but once the configuration is completed, the measurement procedure is essentially the same as described above with respect to the 2ω method. The heater ramp voltage is generated in the same way as in the 2ω method, but instead of being summed with a modulation signal, it is simply buffered and sent to the heater 104. The modulation signal contains a sinusoidal AC current and is sent to the thermometer 102 instead of the DC current used in the 2ω method. The AC current can be produced in many ways. For the example discussed here, the sinusoidal voltage output from a lockin amplifier's oscillator output is used as the input to a voltage-controlled current source, which is a simple op-amp circuit. The amplitude of the modulation current is typically several tens of mA in order to get an adequate third harmonic signal due to temperature modulation.

The thermometer 102 is connected in parallel to the differential inputs of two separate lockin amplifiers 130, 132. A ω lockin amplifier 130 is set to detect signals at the same frequency as the oscillator driving the AC current source, while a 3ω lockin amplifier 132 is set to detect signals at the third harmonic of this frequency. The oscillator output from the lockin 130 used to drive the AC current source is also connected to the reference input of the second lockin 132, insuring that both lockins 130, 132 are synchronized and tuned to the correct reference frequency and phase. As noted above, the signal at 3ω is typically 100–1000 times smaller than the signal at ω (e.g., 10 $\mu$V vs. 10 mV), so a much higher gain setting is used for the lockin which is monitoring the third harmonic. Because the 3ω lockin 132 must reject the much larger first harmonic signal, it must usually be used in "high dynamic reserve" mode, instead of "low noise" mode as is possible in the 2ω method, in order to avoid overloading the inputs.

Once the measurement has been configured, the same measurement procedure used in the 2ω method can be used in the 3ω method. In this case, $V_{th}(\omega)$ corresponds to the resistance of the thermometer 102 and the average temperature; and $V_{th}(3\omega)$ corresponds to the temperature modulation and heat capacity, as explained earlier. The temperature is calculated from $V_{th}(\omega)$ in the same way as described above for the 2ω method using $<V_{th}>$. However, the heat capacity is approximated as $Cp=V_{th}(\omega)/V_{th}(3\omega)$, which differs in form from the formula $Cp=[<V_{th}>*V_{th}(2\omega)]$ used with the 2ω method.

The reason is again related to the formula $Cp=\Delta P/2\omega\Delta T$, discussed earlier. In the 3ω method as described here, the modulation is driven by a sinusoidal current of fixed magnitude $I_{th}$, and the power modulation in the thermometer $\Delta P$ is given by $I_{th}^2 R_{th}$, which is proportional to $R_{th}$ and therefore to $V_{th}(\omega)$. In the embodiment of the 2ω method described earlier, the modulation power to the heater was due to a modulation voltage of fixed amplitude $v_H$. The modulation power is then $v_H^2/R_H$, and is inversely proportional to the heater resistance.

Figure 13G:
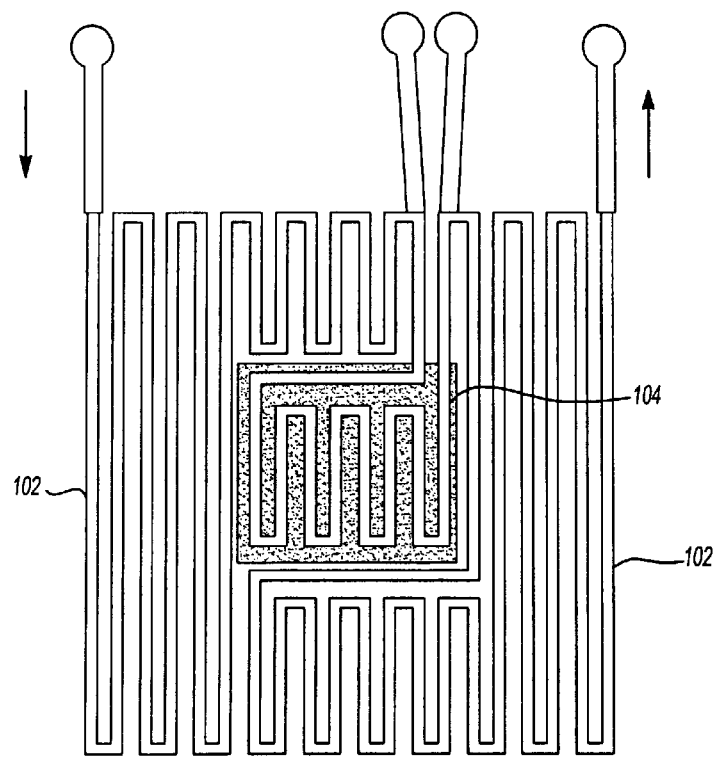

It should be noted that both AC and DC power can be coupled into the heater 104 and/or thermometer 102 in either the 2ω or 3ω methods, and the temperature and temperature modulation may be determined by monitoring either the voltages on the sensors caused by known currents, or the currents caused to flow by known voltages. It should also be noted that other implementations of AC calorimetry in a sensor array format are possible, without departing from the spirit of the invention. For example, two separate heaters and one thermometer can be used, wherein one heater provides a DC power input and the other heater provides an AC power input. Also, a single resistive element can be used as both a heater and thermometer if the 3ω method is used and the resistive element is properly designed so that the temperature is substantially uniform over the area of the thermometer. An example of such a sensor design is shown in FIG. 13G. Although the sensor consists of a single wire, with uniform current passing along its entire length, the voltage is only measured from a portion of the wire, which is in the center of the area being heated. A combined DC and AC current is used, and the voltage may have frequency components at all harmonics up to the third. As in the previous description above, the temperature and heat capacity may be obtained from the first and third harmonics, respectively. This sensor design has the advantage that both AC and DC power are created uniformly across the entire sensor.

Further, the temperature of the sensor can be varied via an external heating method, such as contact with a heated block or illumination by infrared radiation, while the temperature and temperature modulation are measured electronically by the temperature sensor 102. Although the preferred substrate for thermal analysis is a film having a thickness comparable to the thickness of the sample, the use of modulation techniques, such as the 3ω method, also permits thermal analysis of films on substrates that are much thicker than the sample. In such a case, the modulation frequency must be sufficiently high so that the distance over which heat diffuses into the substrate during one modulation cycle is comparable to or less than the sample thickness. This distance defines the effective sampling depth of the modulated calorimetry measurement, and so the heat capacity contributions from the sample and substrate will be comparable, even though the total heat capacity of the substrate is much larger. The 3ω method is particularly useful in this case because it can access much higher measuring frequencies than the 2ω method.

EXPERIMENTAL EXAMPLE
Thermal Stability Analysis

The thermal analysis array structure explained above can also be used to measure the thermal stability of a material.

Thermal stability measurements indicate how hot a material can get before it decomposes or vaporizes and how quickly decomposition takes place as its temperature increases. Thermal stability is particularly important when determining whether a particular material can withstand high temperatures without breaking down or otherwise exhibiting volatile properties.

Figure 14:
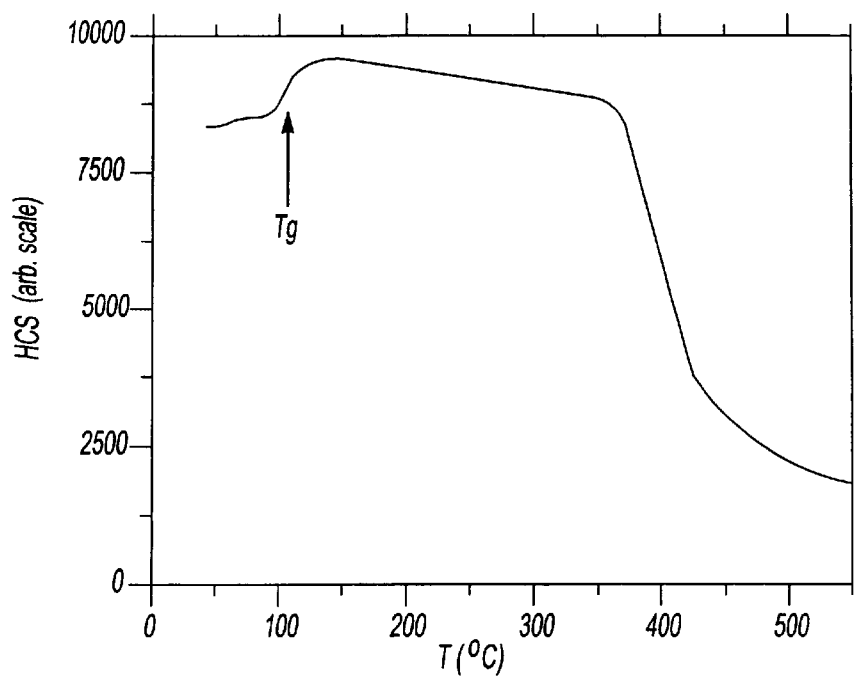
FIG. 14 illustrates a thermal decomposition measurement according to the invention.

Thermal stability can be measured in several ways. FIG. 14 shows sample results of a glass transition and thermal decomposition of a polystyrene film using the sensor array of the present invention. The polystyrene was obtained from Aldrich and used as obtained, which was catalog no. 43,010-2 having a listed melt index of 8.5 and a molecular weight of 230,000. The polymer sample was dissolved in toluene to create a 3% solution, which was manually pipetted onto the sensor. The sample was allowed to air dry on the sensor and then placed in a chamber that was evacuated for a measurement using the 3ω method, described above. Thermal stability measurements can be conducted via any of the signal modulation methods described above. The measurement is conducted in an identical manner as the heat capacity measurement, but the temperature is increased until the material decomposes or otherwise gives up mass. When this occurs, the heat capacity drops sharply and the modulation amplitude increases sharply. This occurs because the same amount of modulated power is going into the heater/thermometer 100 and the membrane 94, but the sample has partially or largely disappeared, so the modulation becomes larger. Further, because the change in the material is not reversible, the modulation will remain large even if the temperature is lowered because of the material's irreversibly changed state.

Heat capacity and thermal stability measurements conducted in this manner are most appropriate for materials that do not liquefy excessively when exposed to heat, such as high molecular weight polymers, because materials having extremely low molecular weights may not stay on the heater/thermometer 100 when heated and may tend to run to the edges of the sensor 12, leaving the heater/thermometer 100 exposed. As a result, the exposed heater/thermometer 100 will give a false indication of decomposition (e.g. a large increase in modulation), because much of the material is no longer on the sensor 12, when in reality the material has simply liquefied and flowed off the heater/thermometer 100. Thus, the thermal capacity measurements described above are more suitable for materials that tend to hold their shape rather than low viscosity liquids. Thermal stability can also be measured with the present invention by heating the sample material on the heater/thermometer 100 in a chamber until it burns and decomposes, then measuring the amount of gaseous fragments in the air as well as the fragments' mass and the air pressure within the chamber.

Dynamic Thermal Analysis

Dynamic thermal analysis may be a less quantitative technique for identifying phase transitions. A sample is typically placed in a cell in contact with a heater block. One thermometer monitors the temperature of the sample, while another thermometer measures the temperature in a reference cell or reference location. The difference in the temperatures of the two thermometers is measured as the temperature of the heater block is steadily raised. The sample temperature tends to lag behind the reference cell temperature, in proportion to the heat capacity of the sample. Thus, phase transitions, such as glass transitions or melting points, show up as kinks or bumps in the temperature vs. time curve.

Figure 15A:
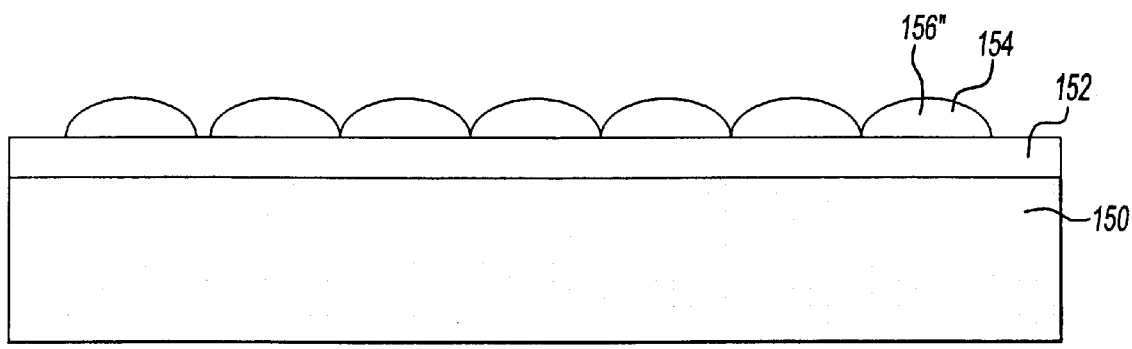
FIGS. 15A and 15B illustrate dynamic thermal analysis conducted according to he present invention.

A preferred structure for conducting dynamic thermal analysis in a sensor array according to the invention is shown in FIG. 15A. The structure has a heater block 150 constructed from a block of material having good thermal conductivity, such as copper or another metal. The high thermal conductivity of the block material causes the heater block 120 to have and maintain a uniform temperature throughout even while the heater power and temperature are varied.

The preferred structure also includes a glass plate 152 that is placed on top of the metal block. Glass is the preferred material for thicker substrates because of its relatively low cost, rigidity, and low thermal conductivity. A plurality of temperature sensors 154, are printed on the top surface of the glass plate 152 in any desired array configuration using any known method, such as lithography. Because glass has very poor thermal conductivity, there will be a relatively large difference between the top and the bottom surfaces of the glass plate 152.

For clarity, the following discussion will describe characterization of a single material, but a library of materials can be simultaneously and/or selectively characterized on the sensor array. The main principle behind dynamic thermal analysis is that the temperature drop across the thickness of the glass plate or between two predetermined points on a surface of the glass plate is proportional to the heat flow through the glass into the sample. Although this ignores the heat flow that is absorbed by the glass to raise its temperature, this heat absorption is the same at all locations on the sensor array and can effectively be disregarded. For materials characterization, as illustrated in FIG. 15A, a sample material is placed on a sensor and the temperature of the heater block T0 is increased to supply heat through the glass plate 152 to a sample 156. In this particular example, the temperature increase in the heater block 150 will create a temperature difference $\Delta Tij$ across the thickness of the glass 152, and the heat will eventually conduct through the glass to heat the sample up to a temperature Tij. Thus, the temperature difference across the glass plate $\Delta Tij=Tij-T0$. Alternatively, the temperature difference can be measured between a point on the glass plate 152 containing the sample and a reference point on the glass plate 152, which reference point may contain a sample that is known to not have any phase transitions in the temperature range of interest.

The sensors 154 on the glass plate 152 measure the temperature and temperature increase rate of each sample. If the temperature of the sample 156 is rising at 1 degree per second, for example, there must be a certain amount of heat flowing through the glass 152 to the sample 156. When the temperature of the heater block 150 is ramped upward, a certain amount of heat flow J is required to increase the sample's temperature at the same rate. If there is not enough heat supplied to the sample 156 to raise its temperature, the temperature of the sample 156 increases mores slowly than the heater block 150, increasing the temperature difference $\Delta Tij$ between the top and bottom surfaces of the glass 152. As the temperature difference increases, more heat flows through the glass 152. For each material, there is a specific value of $\Delta Tij$ at which the heat flow through the glass 152 is the correct, steady state amount for raising the temperature of the material sample. Because each material has different thermal characteristics, the heater temperatures at which this steady state condition occurs, and thus the $\Delta Tij$ value, will be different for different materials.

The temperature difference $\Delta Tij$ corresponds qualitatively to the heat capacity of the sample 156 because some materials require a greater heat input to raise its temperature a certain amount and therefore causes a higher value for $\Delta Tij$. As a result, a large $\Delta Tij$ corresponds qualitatively with a higher heat capacity material, while a lower $\Delta T_{ij}$ corresponds to a lower heat capacity material. More importantly, the large changes in the heat capacity, which occur at phase transitions, will show up as kinks or bumps in the temperature vs. time data for a given sensor. For example, the temperature difference $\Delta T_{ij}$ between the top and bottom surfaces of the glass plate 152 increases sharply at a melting point because large increases in the heat input result in little or no change in the sample material's temperature; the temperature increase in the sample material lags behind the temperature increase in the heater block 150 by a much larger amount than at a point away from the melting point of the sample 156. After melting is complete, $\Delta T_{ij}$ may return to a lower value.

The structure for dynamic thermal analysis is particularly suitable for testing materials that cannot dissolve easily in a liquid and form a thin film on the sensor when the liquid evaporates, such as highly crystalline polyethylene samples. For dynamic thermal analysis, as explained above, the sample material can be simply dabbed onto each sensor without having to form a thin film, e.g., from a slurry, gel, or powder. Further, the thermal characteristics of the glass plate 152 in the present embodiment do not adversely affect the thermal characterization procedure if the dimensions of the material sample and the glass plate's thickness are on the same order of magnitude.

Figure 15B:
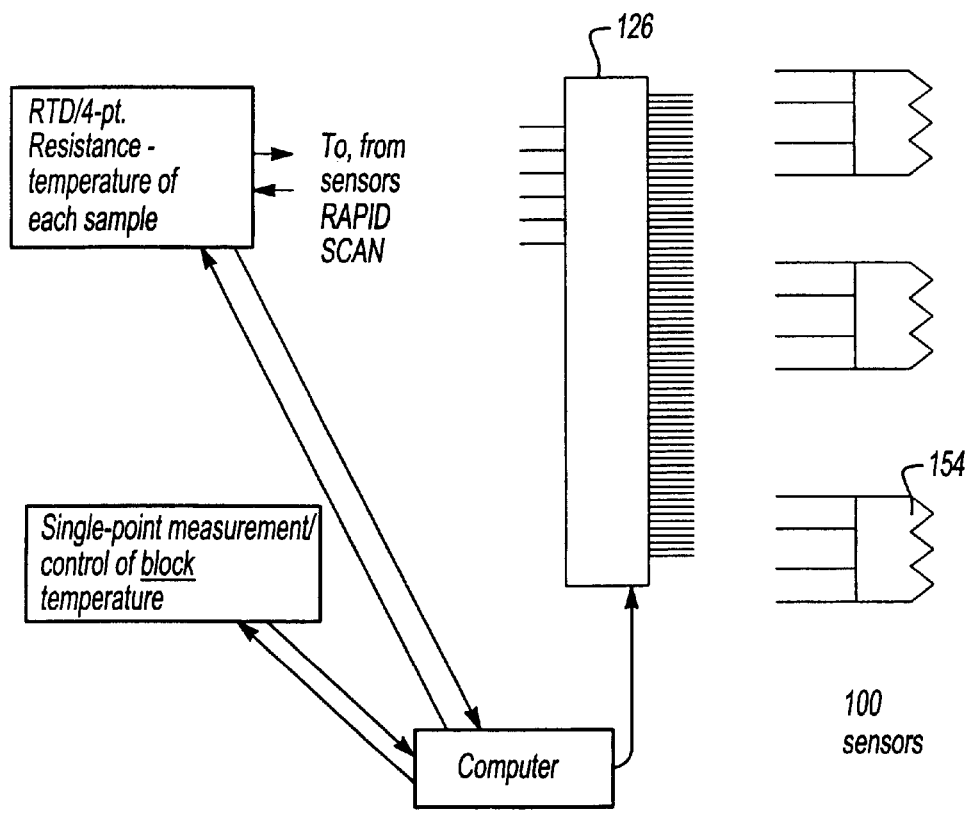

FIG. 15B is a representative block diagram of a materials characterization apparatus that is designed for dynamic thermal analysis. As explained above, an insulating substrate, such as a glass plate, has a plurality of thermometers 154 disposed on its surface and sits on top of a metal block heater. The temperature of the metal block heater is increased, and the electronic platform monitors the temperature of the block with one or more thermometers that are in contact with the block.

Because the entire sensor array structure is heated simultaneously in this particular example, all of the samples on the sensor array must be measured simultaneously or via rapid repeated scanning. Therefore, the preferred electronic link between the sensor array and the electronic platform will include multiple channels for monitoring the sensor operation, preferably one channel per sensor, for maximum speed. Alternatively, the electronic platform rapidly scans through all of the sensors via the multiplexer to measure each sample's temperature (by measuring the resistance in each thermometer). The temperature difference $\Delta T_{ij}$ can be calculated by the computer or processor, if desired, to generate the thermal characterization data and/or plot. The reference temperature can be the temperature of the heater block 120, or the temperature of a sensor that does not carry a sample or that carries a sample having no phase transitions over the temperature range being studied.

EXPERIMENTAL EXAMPLE

Dielectric Spectroscopy

The sensor array of the present invention is not limited only to conducting thermal analysis. As illustrated in FIGS. 16A through 16D, for example, the invention can also characterize electrical properties, including but not limited to the complex dielectric constants of materials.

The basic principles behind dielectric spectroscopy are now briefly discussed. To measure the dielectric constant of a material, the material is typically placed in between two metal plates that have an electric field in between them going from a positive charge to a negative charge. If the molecules of the material in between the two metal plates are more asymmetric, they usually have a greater tendency to polarize in response to the electric field, and the molecules will rotate so that they align with the electric field. The molecular realignment of the material creates its own electric field responsive to the electric field imposed on the material and tends to cancel out at least part of the imposed electric field. Materials having stronger dipole characteristics (and therefore a greater dielectric constant) will create a stronger responsive electric field and will therefore cancel out a greater portion of the imposed electric field.

The overall electric field reduction can be measured by monitoring the charge Q required to create a voltage V between the two metal plates. When the material to be tested is placed between the metal plates, an additional charge $(\in -1)Q$ may flow onto the plates to maintain the voltage V, wherein $\in$ is the dielectric constant of the material. As can be seen from the equation, a material with a larger dielectric constant will require more charge to achieve a given voltage drop across the metal plates. In short, the plates and the material together form a capacitor, and changes in the capacitance reflect changes in the dielectric constant.

The dielectric constant provides information about the physical characteristics of the material being tested at the microscopic level. Some molecules whose positive and negative charges are at the center of each atom in the molecule will exhibit dielectric properties when placed in the electric field because the electric field will slightly displace the nuclei of the atoms in the molecules, creating a positive charge at one end of molecule and a negative charge at the other end. Materials that exhibit greater dielectric properties, however, often have molecules that are asymmetrically charged to begin with. When the material is placed in the electric field, the molecules simply rotate and align themselves with the electric field.

Figure 16A:
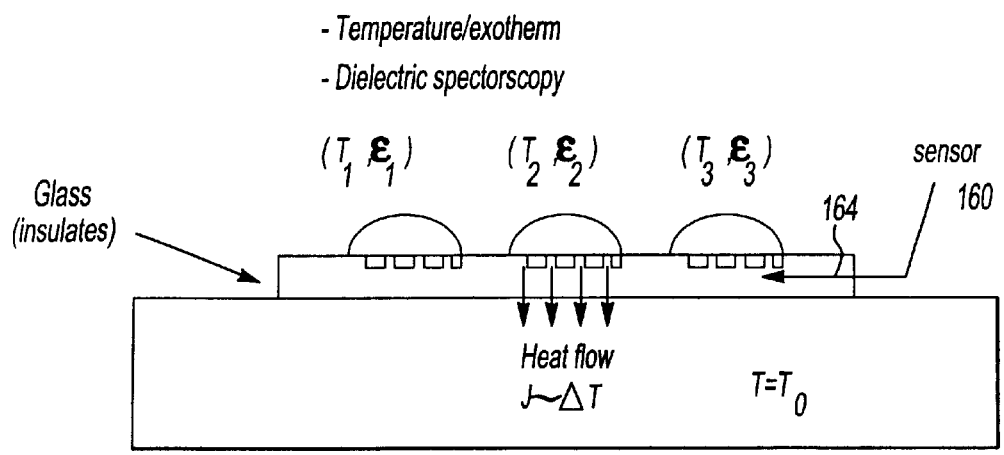
FIGS. 16A through 16E illustrate dielectric spectroscopy conducted according to the present invention.
Figure 16B:
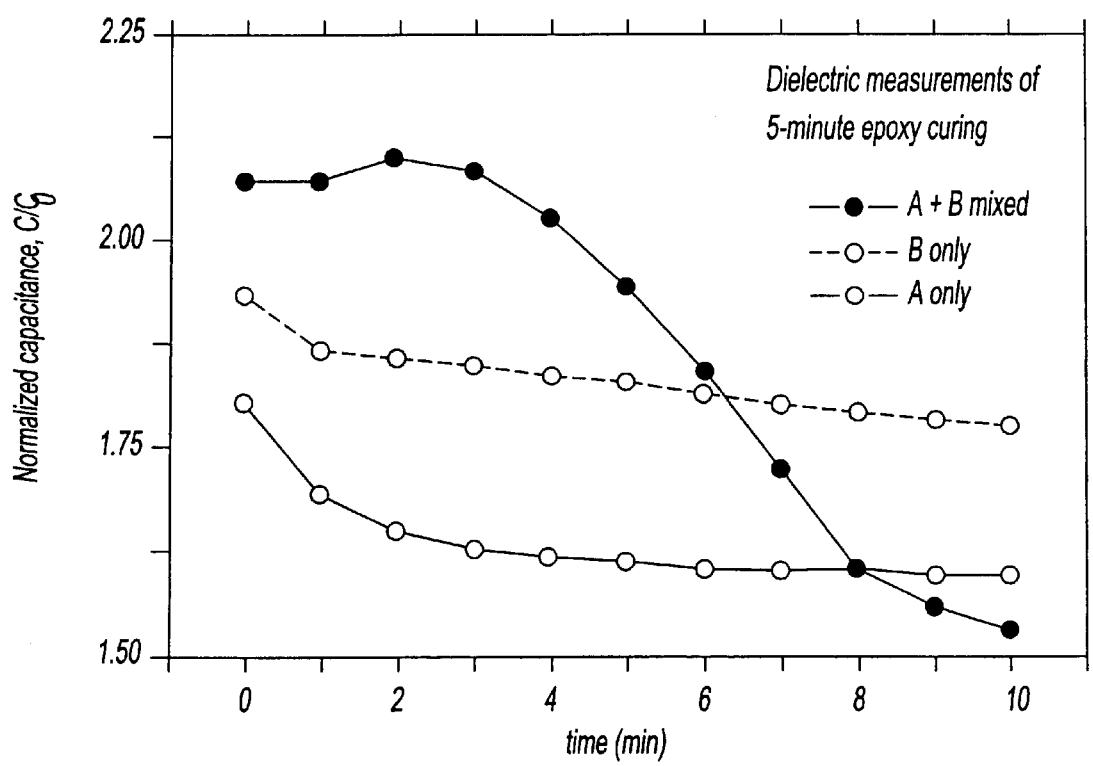

Monitoring the dielectric properties of materials over time is an effective way to detect, for example, curing or cross-linking of glues, thermosets, epoxies, and similar adhesive materials. FIG. 16B illustrates an example where the dielectric properties of a 5-minute epoxy are monitored over time using the sensors described below. In a typical epoxy curing reaction, the molecules in the liquid resin initially move and rotate relatively freely, allowing them to orient in response to an imposed electric field. As the molecules begin to cross-link (e.g., thereby hardening the epoxy or glue), they are less able to align themselves in response to the electric field, decreasing the dielectric constant of the material and thereby decreasing the sensor's capacitance. After the epoxy is completely cured, the molecules are not able to realign themselves, dropping the dielectric constant of the material, and therefore the capacitance of the sensor down even further. Thus, monitoring changes in the dielectric constant of a material over time can provide valuable information about the speed and nature of chemical reactions, such as the epoxy curing reaction described above.

Figure 16C:
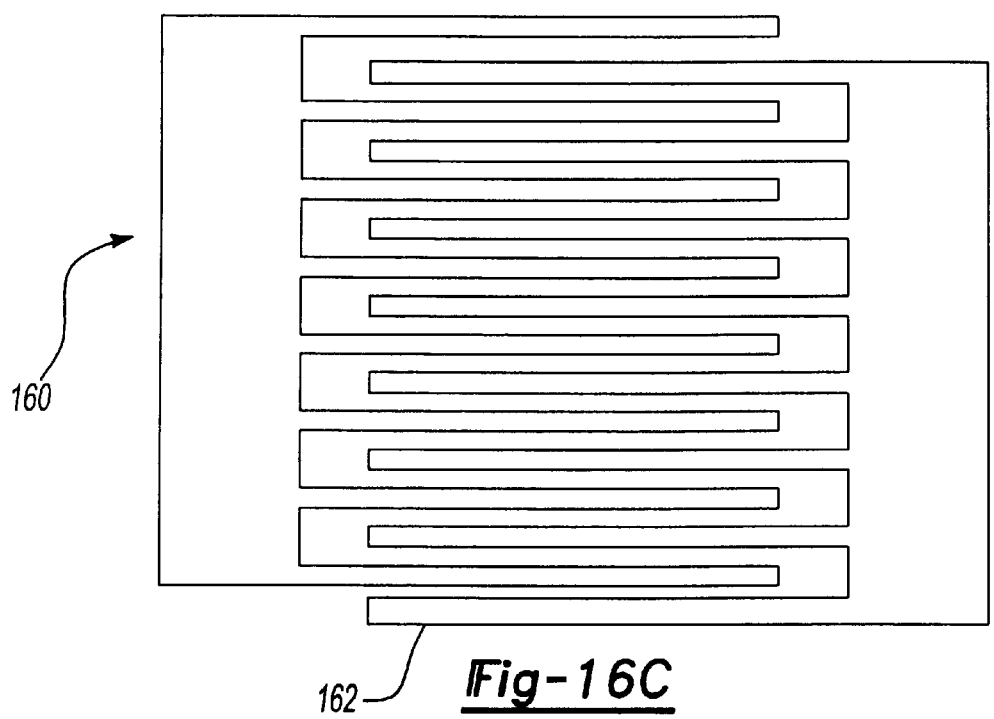
Figure 16D:
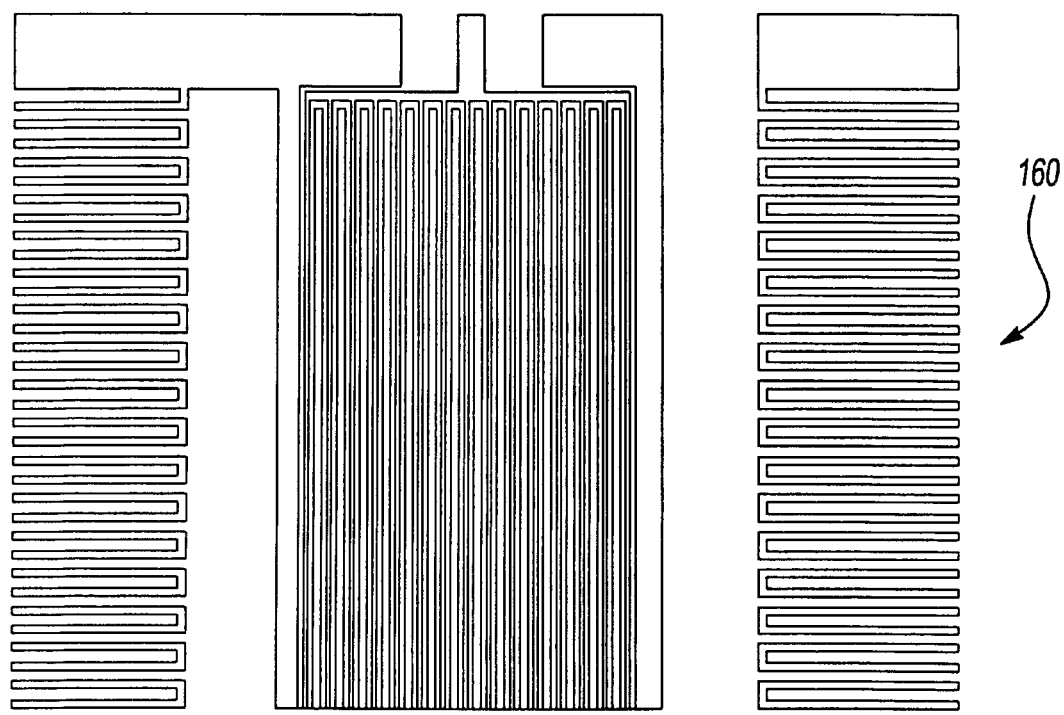
Figure 16E:
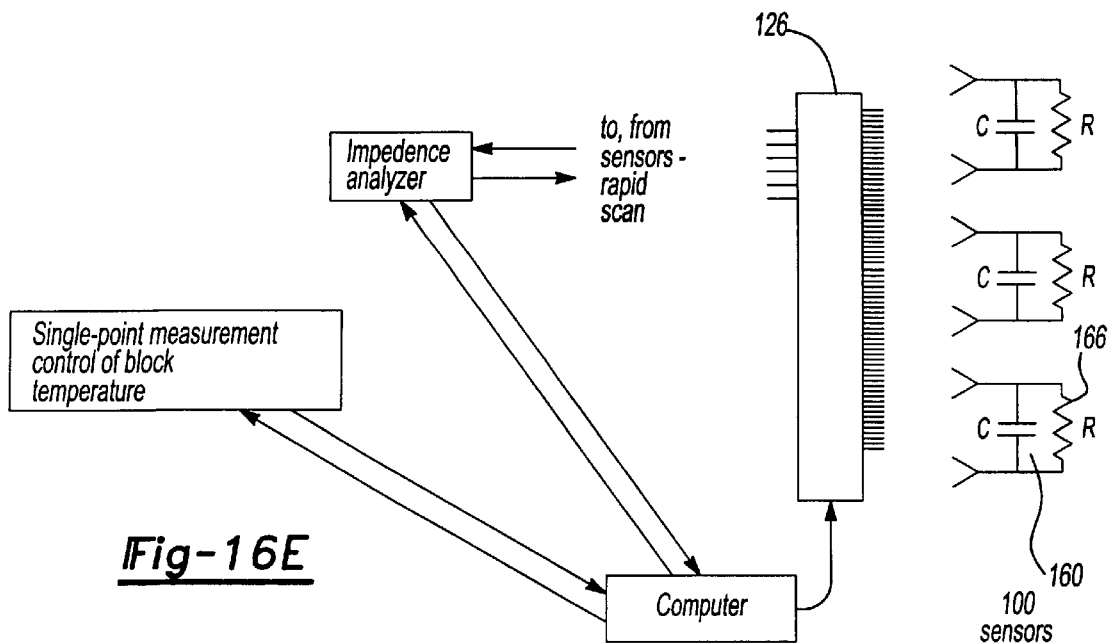

FIGS. 16A, 16C, 16D and 16E explain the preferred sensor geometry and apparatus structure that can be used for dielectric spectroscopy in the sensor array of the present invention. For simplicity, the structure and operation of only one sensor is discussed, but, like the other experimental examples, the preferred method and apparatus for conducting testing involves using a plurality of sensors disposed on a sensor array and coupled with an electronic platform, as represented in FIG. 16E. The most common technique for measuring the dielectric constant of a material is, as noted above, forming a capacitor with the material to be tested in between two plates. Forming a sandwich-type capacitor and obtaining measurements from such a capacitor, however, is often a cumbersome operation, especially when used with liquid samples. Furthermore, the geometry of the capacitor needs to be well defined; the user should know the exact thickness of the capacitor layers, position the plates, and maintain these dimensions throughout the testing.

As shown in FIGS. 16C and 16D, a preferred sensor structure for dielectric measurement according to the present invention is a planar capacitor having interdigitated electrodes 160. The interdigitated electrodes look somewhat like two interlocking combs where the "teeth" 162 do not touch each other. Note that because the thermal characteristics of the substrate 164 are not a concern when measuring electrical properties, the substrate supporting the electrodes 160 can have any thickness (i.e., it does not have to be a thin membrane). However, it is desirable that the substrate 164 should have low dielectric losses under the desired measurement conditions and not exhibit any phase transitions or other unusual behavior. Thus, the electrodes 160 themselves can be printed on glass sheet, quartz, sapphire, or any other desired inert substrate material.

The advantage of the interdigitated electrodes is that the material sample's dimensions do not affect the output of the sensor because the capacitors formed by the wires of the interdigitated electrodes 160 are so small; as long as the thickness of the material placed on the electrode 160 is a few times larger than the spacing between the electrode wires, the thickness of the material sample is no longer important because the electric field is virtually zero at a distance that is several times the spacing between the wires 162. For example, if the spacing between wires 162 in the electrodes is 5 microns, the electric field is reduced roughly by a factor of 10 for every 10 $\mu$m of distance away from the surface. The wire spacing is preferably kept as small as possible so that the capacitance can be kept large enough to measure easily. More particularly, the capacitance obtained from a given sensor will be in the range of $L^2/D$ (in picofarads pF), where L is the length of one side of a square sensor and D is the spacing between the wires, both in units of centimeters. For this example experiment the electrode 160 dimensions for use in the sensor array of the present invention was a 2 millimeter square sensor with a 5 micron wire spacing, which will give capacitance readings of around 10–15 pF. However, the electrodes 130 can any have dimensions to obtain a capacitance range meeting the user's own specifications.

For example, the sensor array used in the experiment shown in FIG. 16B was fabricated from 1000 Å Cr metal on a 5" square glass substrate using a standard photomask blank as a starting substrate. The starting substrate is preferably purchased pre-coated with the metal and a photoresist. The photoresist was patterned by contact printing from a master photomask, and the exposed Cr metal was etched away chemically. The resulting interdigitated electrodes 130 cover a 2 mm square and contain lines and spaces of 5 $\mu$m.

FIG. 16E is a simplified block diagram representing a materials characterization system having a sensor array that is designed for measuring dielectric properties. Like the other embodiments described above, the sensor array is controlled by an electronic platform via a multiplexer that directs electronic signals to and from selected sensors. The electronic platform can measure the complex impedence across each capacitor to determine the capacitance, resistance and complex dielectric constant of the materials on each sensor. For example, the capacitance of a sensor can be measured in less than 0.1 seconds using a conventional capacitance/resistance meter or impedance analyzer. The multiplexer can scan the electrodes 160 in any order and any combination rapidly, as explained in previous examples. Alternatively, a separate drive circuit can be provided for each sensor so that the sensors can be measured simultaneously. The capacitance and losses due to the various interconnect circuitry, including wires, signal routing means, etc., can be measured with the sensor array 10 removed from the apparatus. Subsequent measurements with a sensor array 10 in place can then be corrected to separate the impedance of the electrodes 160 from the impedance due to the interconnects.

Because dielectric spectroscopy does not necessarily involve measuring the thermal properties of the material, monitoring the material temperature is not necessary if measuring the dielectric constant alone. However, the interdigitated electrode structure can be combined with, for example, a resistance thermometer 166. This combined structure can monitor changes in the dielectric constant during a chemical reaction while simultaneously monitoring thermal events such as exotherms. The combined electrode/thermometer structure preferably has the thermometer placed in the center of the electrode to provide the most accurate temperature reading. By conducting the dielectric and thermal measurements simultaneously, more information is made available from a single experiment. In addition, the glass transition of the cured resin can be measured by operating the system in Dynamic Thermal Analysis modes as described above.

More specifically, the scans shown in FIG. 16B were obtained by coupling selected sensors to an SRS 560 LCR meter (inductance/capacitance resistance meter) operated at a 1 kHz frequency. Although one preferred operation mode includes repeated measuring the capacitances of multiple sensors in the array 10 during a single experiment, the data shown in FIG. 16B was acquired one sample at a time. The LCR meter was coupled to a selected sensor's contact pads 14 via two wires attached to micropositioners. Once the sensor was contacted, a fluid sample was applied directly to the sensor, and measurements were recorded manually once per minute, for a total time of ten minutes. The capacitance of the leads, before connecting them to a sensor, was approximately 1 pF. The capacitance of a bare sensor with the leads was approximately 15–20 pF. The capacitance of a sensor with one of the epoxy components placed on top of it was typically 3040 pF immediately following application of the sample.

The epoxy used in the specific example shown in FIG. 16B is Devcon 5-minute epoxy. In the experiments conducted on the individual epoxy components, denoted A and B in the figure, fresh samples of the components were removed from the storage tube immediately before being applied to the sensor. When a mixture of A and B was tested, the two components were removed from their tubes and mixed for approximately 30 seconds before being applied to the selected sensor. A large reduction of the sensor capacitance can be seen for the sample of the mixed epoxy, corresponding to setting, while the capacitance for the individual components A and B change by much smaller amounts.

Determining the dielectric properties of materials in and of themselves can also be important. For example, integrated circuits often includes dielectric layers separating multiple wires from each other to minimize or eliminate cross-talk, and it has been found that lower dielectric constant materials, which do not polarize easily, allow signals to propagate more quickly. Thus, conducting dielectric spectroscopy according to the claimed invention allows rapid screening of many materials to find materials that have the optimum dielectric properties.

EXPERIMENTAL EXAMPLE
Surface Launched Acoustic Wave Sensors

Figure 17A:
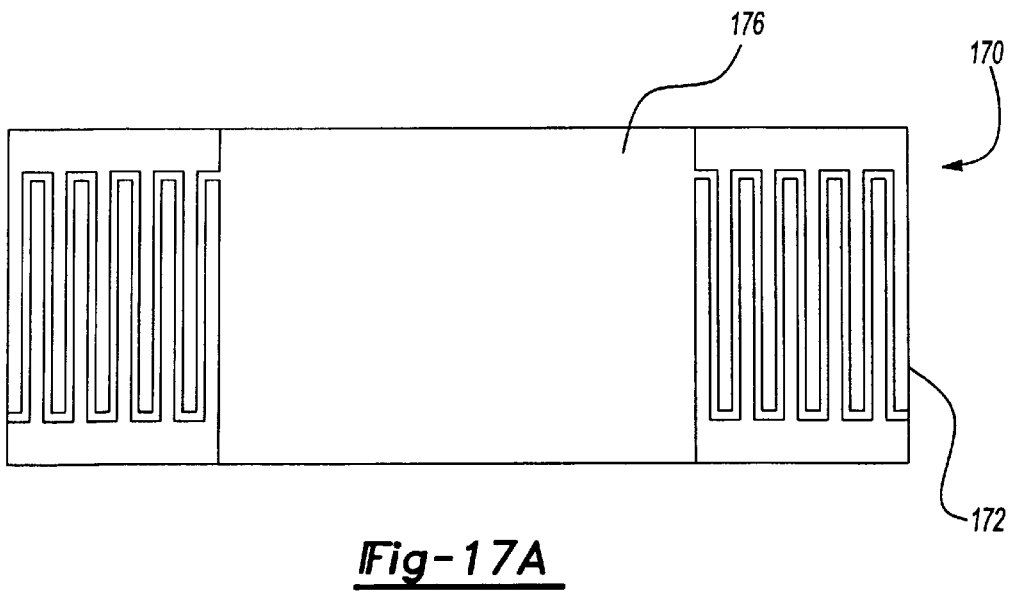
FIGS. 17A and 17B show an example of a mechanical resonator structure that can be used in the invention.
Figure 17B:
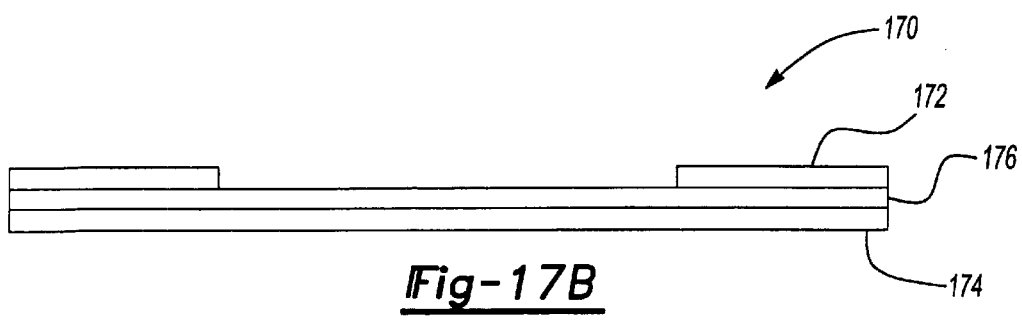

FIGS. 17A and 17B show an example of a surface launched acoustic wave sensor 170 for measuring material properties such as viscosity, density, elasticity, and capacitance. An electrode in the surface launched acoustic wave sensor may also have interdigitated fingers 172, in this case for launching and measuring transmission of acoustic energy. Further, like the examples shown in FIGS. 16C and 16D and described above, the interdigitated structure of the sensor electrodes in FIGS. 17A and 17B can measure the dielectric constant and the conductivity of the material, if desired.

In this example, surface launched acoustic wave sensors can be fabricated on thin silicon-nitride or etched silicon membranes 174 similar to those described above. A piezo-electric material 176, such as zinc oxide, is then deposited as a thin layer on top of the membrane to produce an acoustic wave sensing device. The physical dimensions of the electrode, such as its thickness, size, and configuration, can be adjusted so that the electrode operates in, for example, a surface acoustic wave (SAW) resonance mode, a thickness shear mode (TSM), a flexural plate wave (FPW) resonance mode, or other resonance mode. When the electrode acts as a resonator, its resonating response is affected by, for example, the sample's viscosity and density. U.S. application Ser. No. 09/133,171 to Matsiev et al, filed Aug. 12, 1998, describes mechanical resonators in more detail and is incorporated by reference herein.

Thus, because the surface launched acoustic wave device shown in FIGS. 17A and 17B can serve as both a mechanical resonator and as a sensor for characterizing other material properties, such as the dielectric constant, multiple devices can be arranged in a sensor array format to screen material properties. The versatility of the surface launched acoustic wave device and other mechanical resonators make it a good choice for observing multiple materials as they undergo a chemical or physical process involving changes in viscosity, density, conductivity, molecular weight, or chemical concentration.

Further, the mechanical resonator can be used to measure weight or force because of its responsiveness to mechanical loading. When surface launched acoustic wave sensors are arranged in an array format, the sensor array can be used to weigh simultaneously multiple samples of powders or liquids, each sensor acting as a separate scale. As noted above, these mass measurements can be conducted simultaneously with viscosity, conductivity, and dielectric constant measurements due to the interdigitated structure of the sensor electrode. Electroplating or solution deposition could also be measured using the arrayed mechanical resonators by correlating the resonator response to mass loading.

The mechanical resonator structure shown in FIGS. 17A and 17B can also be used for magnetic material characterization. More particularly, the mass loading effect of the resonator can be used to measure a sample material's response to an external magnetic field. In this application, the resonators in the array are coated with the test material or materials, and the sensor array is placed in a magnetic field. Any magnetic response of the material to the magnetic field would appear as a change in the mass loading experienced by the resonator. This mass loading change damps the resonance signal from the resonator, and the amount of damping can be correlated with the material's response to the applied field. Alternatively, a mechanical actuator can be used in the same manner as the mechanical resonator, and characterization would be conducted by measuring the amount of displacement in the actuator.

EXPERIMENTAL EXAMPLE
Electrical Transport Properties

Yet another set of material properties that can be measured using the materials characterization system of the present invention are the electrical transport properties of materials: electrical resistance, Hall effect resistance, magnetoresistance, and current-voltage curves showing non-linear features such as breakdown voltages and critical currents. As explained above, the "plug-and-play" format of the invention may only requires the user to change the sensor array, not the entire machine or any hardware, to measure a different material property, depending on the embodiment being practiced. The changes may occur at the sensor level; the electronic platform and multiplexer can remain generally the same regardless of the specific material characteristic to be tested. Minor variations in the electronic hardware, such as amplifiers, voltmeters, capacitance meters and the like may be needed to conduct the measurements, but these modifications can be external to the sensor array and can be conducted in the flexible electronic platform. The following discussion will focus on the specific sensor structure that is used to measure electrical transport properties; the connections between the sensor array, the multiplexer, and the electronic platform, as well as their operations, are similar to the connections and operations described above.

Figure 18A:
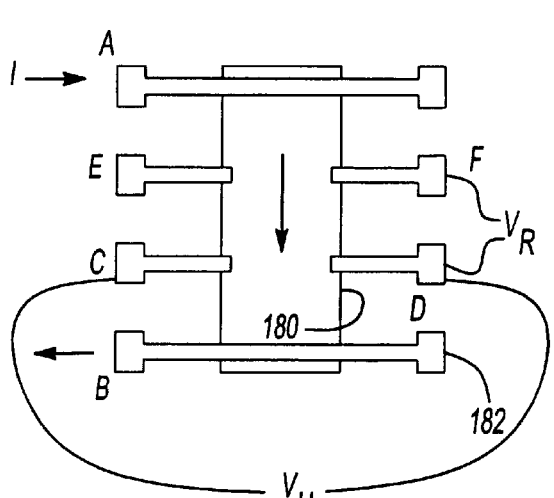
FIGS. 18A through 18C illustrate electrical transport characterization conducted according to the present invention.

FIG. 18A show a preferred sensor structure that can measure the electrical transport properties of a material. Like the above examples, a plurality of the sensors are disposed in an array format to measure these properties for a materials library quickly. As is known in the art, resistivity is an intrinsic property that does not depend on the dimensions of the material, and resistance equals the resistivity $\rho$ of the material times the length of a material sample L divided by the material sample's cross-sectional area A ($R=\rho L/A$). The Hall coefficient, as is also known in the art, indicates the number of electrons or holes in a material per unit volume and indicates the sign of the charge carriers.

Measuring these two characteristics according to the present invention is relatively simple. The materials to be tested are formed into bars 180 having known dimensions, and the sensors used to test the material are equipped with six leads 182 that preferably contact the bar of material at both ends and in the middle, as shown in FIG. 18A. The bars 180 themselves can be formed by depositing the library elements through a mask onto the leads 182, or by depositing the materials on the substrate first using a mask and then printing the leads 182 on top of the bars 180, again using a mask. In some cases, the bar 180 should be sintered or annealed after deposition, so the anticipated effects of the sintering/annealing process on the contacts should also be considered when selecting a depositing order. Like previous embodiments, the contact pads in this embodiment provide the connection between the sensor array and the electronic platform that sends and reads signals to and from the individual sensors.

Figure 18B:
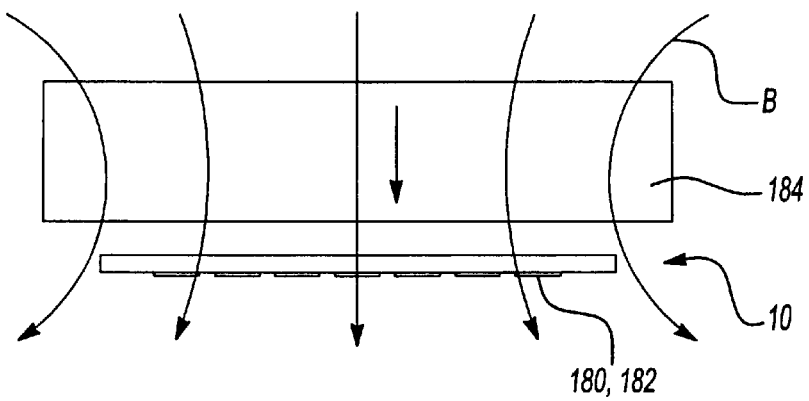
Figure 18C:
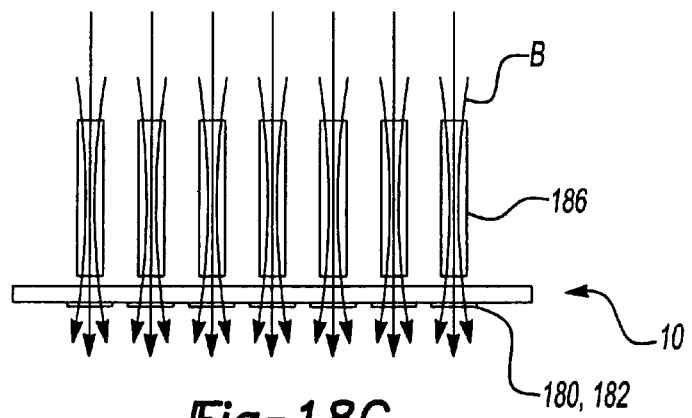

To obtain a material's resistance, an AC or DC current is simply passed through the bar 180 and the AC or DC voltage across the bar 180 is measured using leads EC or FD, without placing the sensor array in a magnetic field. To obtain a material's Hall coefficient and magnetoresistance, the sensor array should be placed in a magnetic field B that points perpendicular to the substrate. The magnetic field B can be generated in a variety of ways. For example, a large permanent magnet or electromagnet 184 can be used to generate a magnetic field that is perpendicular to the substrate over the entire sensor array, as shown in FIG. 18B. Any non-uniformity in the magnetic field B can be detected before conducting the materials characterization, by using an array of identical, calibrated Hall effect sensors, and this non-uniformity can be taken into account in any subsequent analysis of the data obtained from the sensor array with samples. Alternatively, as shown in FIG. 18C, an array of permanent magnets or electromagnets 186 having the same array format as the sensor array can be used in place of the single magnet. The pole portions of the magnet array are preferably placed close to the individual samples and sensors in the sensor array. As for the single magnet, the magnet array can be calibrated with an array of Hall effect sensors to detect any non-uniformities or variations in the field strengths produced by the individual magnets so that these variations can be taken into account in subsequent analysis of the data from the sensor array.

During testing, a current is sent through the bar 180 using contacts A and B. The material's resistance in a magnetic field, known as magnetoresistance, can be measured in the same manner as resistance except the sensor array is exposed to a magnetic field so that the sensor can measure any changes in resistance in response to the magnetic field. The Hall voltage is obtained by measuring the voltage across the width of the bar, at contacts CD or EF, and the Hall resistance is given by:

$$V_H = IR_H = I(B/nec)$$

As can be seen from the equation, the Hall voltage for a given magnetic field strength corresponds to the charge carrier density (n) and the sign of the carriers (+e or −e) for the material being tested. As is well known in the art, the Hall voltage results from the forces on moving charge carriers in a magnetic field. This force, which is perpendicular to the direction of motion as well as the field direction, causes positive and negative charges to build up on opposing edges of the sample until the resulting electrical force on the moving charge carriers exactly cancels the magnetic force. This condition can be used to derive the above equation for the Hall resistance.

EXPERIMENTAL EXAMPLE
Thermoelectric Material Properties

Yet another group of properties that can be measured using the sensor array of the present invention are two characteristics of materials that pertain to their desirability for use in thermoelectric cooling devices: thermopower and thermal conductivity. Thermopower will be discussed first.

When a temperature gradient is imposed on a material under open circuit conditions, an electric field occurs due to the diffusion of charge carriers in the temperature gradient. In equilibrium, the force on the charge carriers due to the electric field is just sufficient to counteract their tendency to diffuse in the temperature gradient. The ratio between the temperature drop and the voltage drop across a sample is known as the thermopower, $S = \Delta V / \Delta T$, and is typically measured in units of $\mu V/K$. The thermopower is a fundamental physical property of an electronic material that can provide information about a materials electronic structure and other characteristics. In addition, the thermopower is a key physical parameter for materials which are used as thermoelectric cooling devices. A large thermopower value is a desirable property for a material in cooling device applications. To search for improved thermoelectric materials using combinatorial chemistry techniques to synthesize libraries of thin films of candidate materials, it is desirable and necessary to be able to measure rapidly the thermopower of many materials.

Figure 19A:
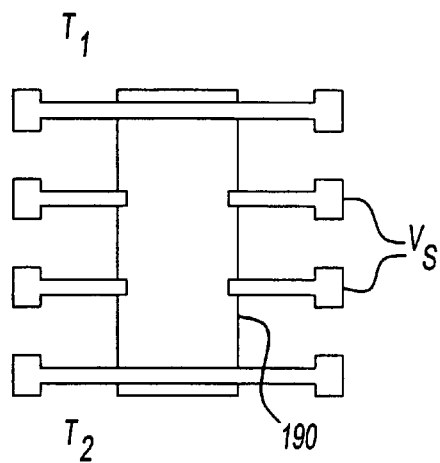

The thermopower S can be measured using the sensor design explained above and shown in FIG. 19A by measuring the voltage drop $\Delta V$ across a bar sample 190 for a known temperature difference $\Delta T$ along the sample 190. This can be conducted in a variety of ways. In one embodiment, as illustrated in FIG. 19B, a temperature gradient is imposed along the entire sensor array 10 by contacting two opposing edges 191, 192 of the array with metal blocks 194, 196 whose temperatures are controlled and measured. If the substrate has high thermal conductivity, such as silicon, then heat losses to radiation and convection will be relatively minor compared to the heat conduction along the substrate, and a fairly uniform temperature gradient will be produced. The gradient may be approximated as the total temperature drop divided by the width of the array, and the temperature drop across an individual sample will be the gradient times the length of the sample. In other words, $\Delta T_{sample} = \Delta T_{array} * (L_{sample}/L_{array})$. More precise information about the temperature drop across each sample may be obtained by including two temperature sensors next to each sample within the sensor array 10, one near each end.

The above example ignores heat losses through the electrical contacts to the sensor array, which may cause the temperature profile to deviate from the preferred linear gradient form or cause most of the temperature drop to occur over a relatively small distance near the edge of the array instead of evenly across the entire array. An alternative embodiment which is not subject to this problem is shown in FIG. 19C. In this embodiment, a chain of heating/cooling elements 198, such as thermoelectric heat pumps, is used to impose a temperature drop across each row in the sensor array, by means of blocks of metal or other thermally conductive material that contacts both the heating/cooling elements 198 and the substrate. The elements 198 preferably alternate direction so that all of the samples in the array 190 are at the same average temperature. The structures that produce the temperature gradient on the array may be integrated into the compression plate 40, shown in FIG. 4, used to apply pressure on the sensor array against the contacts to the circuit board.

In yet another embodiment, the temperature gradient can be produced by resistive heating elements that are part of the sensor array itself rather an external heating fixture. This structure is most easily accomplished if the substrate has low thermal conductance, either via a low thermal conductivity material (e.g., glass) or via a thin film substrate (e.g., silicon nitride). A large number of configurations are possible; ideally, temperature sensors are placed at both ends of each sample and a resistive heating element is placed near one end of the sample. In addition, at least two electrical connections are at the ends of the sample for measuring the thermoelectric voltage.

The sensor array structure for measuring thermal conductivity will now be discussed. Like thermopower, thermal conductivity is important for determining how efficient a given material will be for use in thermoelectric cooling devices. An ideal material in a cooling device application will have low thermal conductivity in conjunction with low electrical resistance to minimize heat leakage in the device and create a large temperature difference across the device with minimum energy consumption and heat dissipation.

FIGS. 20A and 20B show a preferred sensor structure for measuring the thermal conductivity of materials. As in the previous experimental examples explained above, the description will focus on the structure of a single sensor, but it is understood that multiple sensors are used in the present invention in an array format, and that sensors measuring different properties can be included on the same sensor array. Also, analysis of thermal conductivity may be useful in materials research contexts other than the search for new thermoelectric materials.

The preferred thermal conductivity measurement method is via vapor-deposited films, on the order of half-micron thick, on membranes, similar to the structure used for heat capacity measurements. Other methods may also be used to deposit thin film samples, such as evaporation from a solution or suspension. As in heat capacity measurements, thermal conductivity measurements preferably minimize the effects of the substrate's thermal characteristics on the overall measurement results. FIGS. 20A and 20B illustrate a preferred sensor structure 200 for measuring thermal conductivity. As can be seen in FIG. 20A, the sensor structure 200 for thermal conductivity measurements can be of similar construction and materials as the structure used in heat capacity measurements, such as a silicon-nitride membrane, so that the thermal characteristics of the material sample can be easily detected and separated from the thermal characteristics of the substrate on which the sample sits. Thus, the details of the structure will not be repeated here.

Referring to FIG. 20B, a desired sensor pattern is printed via any known method, such as lithography, on the membrane 202 surface opposite the surface on which the material sample 204 will be deposited. This prevents a short-circuit from forming when characterizing electrically conductive materials, such as metals. In this example, the sensor includes two wires 206, 208. The specific geometry of the sensor should be optimized so that the temperature is substantially uniform along the portion 205 of the sensor 200 over which the temperature will be measured on the membrane 202 (e.g., the "active" portion). To accomplish this, the membranes 202 on the sensor array should be made relatively long and narrow to insure that heat flow in the active portion is predominantly between a second (heater) wire 208 and the nearby substrate 210, which contains a first wire 206, i.e., across the width of the membrane 202 (perpendicular to the heater wire 206) and not along the length of the wire 208.

As noted above, a preferred sensor design includes two parallel wires 206, 208 having a known width and spaced a known distance apart. Branch leads 206a, 208a extend from each parallel wire 206, 208 and are spaced a known distance apart for conducting voltage measurements V1 and V2 along the parallel wires. In this embodiment, the first wire 206 is used as a thermometer and the second wire 208, which is on the membrane 202, is used as both a heater and a thermometer. As in previously described structures, the temperature is monitored by measuring the AC or DC voltage and current of the sensor and calculating the resistance, which varies linearly with respect to temperature.

In a preferred structure, the first wire 206 is disposed on the solid silicon substrate 210, near the edge of the silicon nitride membrane window 202, while the second wire 208 is disposed on the membrane portion 202 of the substrate. The silicon in the substrate 210 acts as a large heat sink to prevent the temperature detected by the second wire 208 from rising in response to the heat generated by the first wire. If the width of the membrane 202 is kept small (e.g., less than 1 mm wide and preferably less than 100 µm wide), heat losses due to radiation may be neglected in comparison to the total heat flow through the membrane and sample, and if the thermal conductivity measurements are conducted in a vacuum, heat losses to the atmosphere due to conduction and convection may be neglected. Virtually all of the heat produced by the first wire 206 conducts through the membrane 202 and the sample 204, in a direction perpendicular to the wires 206, 208.

The theory behind thermal conductivity measurements will now be described with respect to the structure shown in FIGS. 20A and 20B. As noted above, thermal conductivity is a measure of how easily heat travels through a material when a temperature difference T2−T1 is imposed on a material sample. When a temperature difference $\Delta T=T2-T1$ is imposed across a material sample, such as a bar sample, heat will flow from the warmer end of the sample to the cooler end. This heat flow J (in watts) is equal to the thermal conductance K multiplied by the temperature difference $\Delta T$. In other words, the amount of heat flow through the sample is proportional to the temperature difference across the sample. The specific proportionality constant depends on both the sample's geometry and the thermal conductivity $\kappa$ of the material, $K=\kappa(A/L)$ where A is the cross-sectional area of the bar in the direction perpendicular to the heat flow, and L is the length. In this sensor, L=the distance from wire to the edge of membrane/substrate, and A=(thickness of membrane/sample)×(distance between branch leads).

Referring back to the sensor structure shown in FIG. 20A and 20B, the second wire 208, which is used as both the heater and the thermometer, carries a relatively large current I2 to generate a known power P for heating the sample and also measure the temperature of the wire; while the first wire 206 receives a small current I1 to conduct a temperature reading. The large current I2 should be large enough to cause significant self-heating in the portion of the sample around the first wire 206, on the order of 5 to 10 degrees C. The small current I1 is preferably the smallest amount of current necessary to measure accurately the resistance of the second wire; it should not be large enough to heat the sample to any significant degree. Even though the small current I1 may cause the sample's temperature to rise a small amount, on the order of a tenth or a hundredth of a degree, this temperature change is negligible relative to the self-heating occurring on the portion of the sample on the membrane and can therefore be ignored. Further, as noted above, the silicon substrate 210 acts as a large heat sink, keeping the temperature of the sample in that area uniform and preventing the temperature of the first wire 206 from rising along with the temperature of the second wire 208.

To measure the temperature difference $\Delta T=T2-T1$, the electronic platform only has to monitor the resistance changes in the two wires 206, 208. The power $I_2 V_2$ generated by the heater, which is equal to the total heat flux, and is input into the sample via the first wire, is known from measurements of I and V. Because the geometry of the sample is also known, the thermal conductivity of the material can be obtained from the temperature difference. Note that the thermal conductivity of the membrane 202 still has to be subtracted from the thermal conductivity measurement obtained from the combined membrane and sample, to obtain the thermal conductivity of the material, but the membrane's thermal conductivity is easily determined by sending current through the sensor without any material on it, i.e., before deposition of the material sample.

EXPERIMENTAL EXAMPLE

Magnetic Material Characterization

The sensor array of the present invention can also characterize the magnetic properties of materials libraries, again by changing possibly only the sensor structure in the sensor array and making minor changes in electronics and including equipment for generating a magnetic field as discussed with reference to transport properties. As explained above, the sensor array of the present invention can measure the Hall coefficient of a material to determine the material's carrier concentration and sign. In the present example, generally, an array of unknown magnetic materials is placed on top of or in close proximity to an array of identically calibrated Hall effect sensors, which are made from a material with a known response to a magnetic field. An external magnetic field of variable strength is then imposed on the sample and sensor. The output of the Hall sensor is compared to the output of an identical sensor that does not contain a sample. The difference in the response of the two sensors is due to the magnetization of the sample. In a preferred embodiment, the sensors with and without the sample are connected in a differential arrangement, which greatly increases the sensitivity to the magnetization of the sample.

Figure 21A:
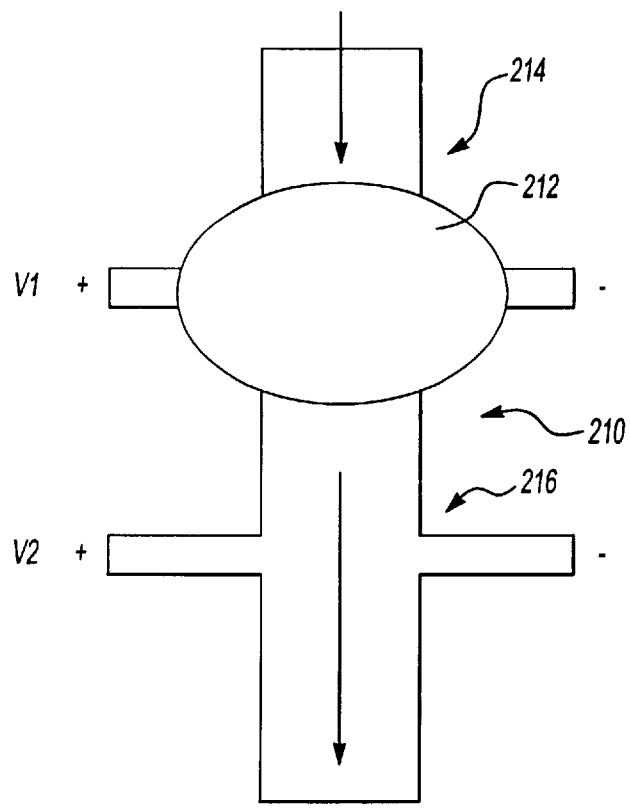
FIGS. 21A and 21B illustrate magnetic property characterization conducted according to the present invention.

The samples may be deposited directly on a Hall sensor 210, as shown in FIG. 21A. In the illustrated structure, a sample 212 can be deposited on one portion 214 of the sensor, with a second portion 216 of the sensor 210 left open to serve as a reference point. The difference between the voltages V1 and V2 when the sensor 210 is placed in a magnetic field corresponds to the magnetic properties of the sample 212. For example, the plot of the Hall voltage versus the magnetic field when there is no material on the sensor will be a straight line, but a magnetic material on the sensor 210 will cause the plot to deviate from the straight line, or will cause the straight line to have a different slope, because the sensor 210 is measuring both the external field and the field of the sample 212. In essence, the sensor 210 used in this embodiment is a magnetic field sensor. Alternatively, the Hall sensors and the samples may be contained on two separate substrates that are pressed together during the measurement. This later method allows reuse of the Hall sensor array.

Figure 21B:
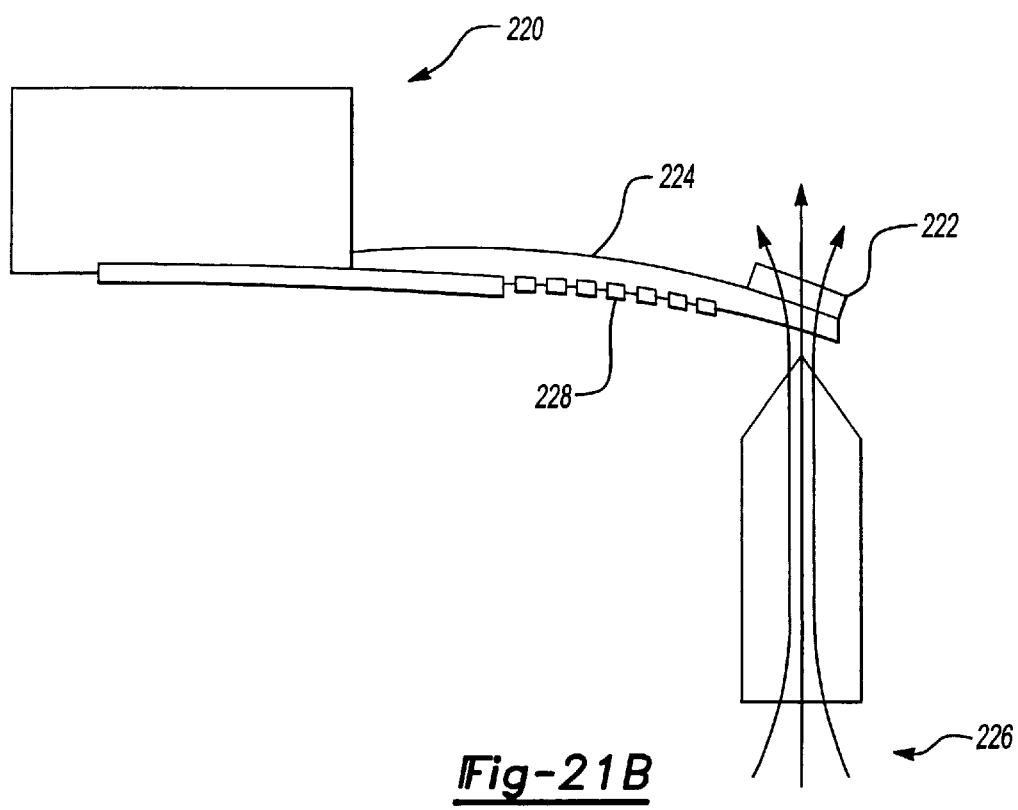

Another specific way in which the magnetic properties of a material can be measured is by forming a sensor array containing cantilever sensors 220, as shown in FIG. 21B. A material sample 222 is placed on a relatively soft, flexible cantilever 224, and then the sensor 220 is placed in a magnetic field 226 having a known field strength and field gradient. The force and/or torque due to the interaction of the field and field gradient with the permanent and/or induced magnetization of the sample will cause the cantilever 224 to deflect. The amount of the deflection will depend on the strength of the sample material's magnetic characteristics.

There are several ways in which the deflection amount can be measured precisely. For example, the cantilever 224 on which the sample material 222 is placed can be one half of a sandwich capacitor such that the cantilever deflection results in a capacitance change. An alternative is to place the cantilever 224 on a piezoresistor 228, which is shown in FIG. 21B, so that the bending of the cantilever 224 strains the resistor slightly, changing its resistance value. The electronic platform can then monitor the amount the resistance changes and correlate the change with the amount of deflection. Other methods of measuring the amount of deflection in the cantilever sensors 220 can be used without departing from the scope of the invention.

It should be understood that various alternatives to the embodiments of the invention described herein may be employed in practicing the invention. It is intended that the following claims define the scope of the invention and that the methods and apparatus within the scope of these claims and their equivalents be covered thereby.

What is claimed is:

1. An apparatus for characterizing a first material property of a first array of samples and a second material property of a second array of samples, comprising:
    a) a first array of 5 or more sensors wherein each sensor of said first array of 5 or more sensors is configured to be associated with at least one sample of said first array of samples;
    b) a second array of 5 or more sensors interchangeable with said first array of 5 or more sensors wherein each sensor in said second array of 5 or more sensors is configured to be associated with at least one sample of said second array of samples;
    c) electronic test circuitry interchangeably in electrical communication with said first array of 5 or more sensors and said second array of 5 or more sensors through at least one electrical interconnection device wherein said electronic test circuitry is configured for sending an output signal to said first array of samples and said second array of samples respectively through said first array of 5 or more sensors and said second array of 5 or more sensors and said electronic test circuitry is further configured for receiving input signals from said first array of samples and said second array of samples, wherein;
        i) said first material property of said first array of samples is determined by comparing said output signals sent to said first array of 5 or more sensors with said input signals from said first array of samples; and
        ii) said second material property of said second array of samples is determined by comparing said output signals sent to said second array of 5 or more sensors with said input signals from said second array of samples.

2. The apparatus as in claim 1, wherein said at least one electrical interconnection device includes a multiplexer.

3. The apparatus as in claim 1, wherein said first array of 5 or more sensors are located on a single substrate.

4. The apparatus as in claim 3, wherein said single substrate is at least partially formed of a polymer sheet and wherein a plurality of thermometers are disposed on said polymer sheet for monitoring temperature of said first array of samples.

5. The apparatus as in claim 4, wherein said polymer sheet is at least partially formed of a polyimide.

6. The apparatus as in claim 4 wherein said single substrate includes a heater disposed on a bottom surface of said single substrate.

7. The apparatus as in claim 1, wherein said first material property is selected from the group consisting of heat capacity, specific heat, thermal conductivity and thermal stability.

8. The apparatus as in claim 1, wherein said electronic test circuitry is configured for characterizing said first material property of said first array of samples substantially simultaneously.

9. The apparatus as in claim 1, wherein said electronic test circuitry is configured for characterizing said first material property of said first array of samples in rapid serial succession.

10. The apparatus as in claim 1, further comprising a probe that is selectively positioned over said first array of 5 or more sensors for assisting in sending an output signal to said first array of samples.

11. The apparatus as in claim 1, wherein said first array of samples includes a first 5 samples and said second array of samples includes a second 5 samples wherein said first 5 samples of said first array of samples is substantially the same as said second 5 samples of said second array of samples.

12. The apparatus as in claim 11, wherein said first material property is selected from the group consisting of heat capacity, specific heat, thermal conductivity and thermal stability.

13. The apparatus as in claim 11, wherein said electronic test circuitry is configured for characterizing said first material property of said first array of samples substantially simultaneously.

14. The apparatus as in claim 11, wherein said electronic test circuitry is configured for characterizing said first material property of said first array of samples in rapid serial succession.

15. The apparatus of claim 1 wherein said each sensor of said first array of 5 or more sensors includes interdigitated electrodes.

16. The apparatus of claim 1 wherein said each sensor of said first array of 5 or more sensors conducts a dielectric constant measurement and a thermal measurement simultaneously.

17. The apparatus of claim 1 wherein the first material property is an electrical transport property.

* * * * *

UNITED STATES PATENT AND TRADEMARK OFFICE
CERTIFICATE OF CORRECTION

PATENT NO.    : 6,535,822 B2
DATED         : March 18, 2003
INVENTOR(S)   : Paul Mansky and James Bennett It is certified that error appears in the above-identified patent and that said Letters Patent is hereby corrected as shown below:

<u>Title page,</u>
Insert item:
-- [73]   Assignee: Symyx Technologies, Inc. --.

Signed and Sealed this

Twenty-sixth Day of August, 2003

JAMES E. ROGAN
*Director of the United States Patent and Trademark Office*